US009399678B2

(12) United States Patent
Castanheira Aires da Silva et al.

(10) Patent No.: US 9,399,678 B2
(45) Date of Patent: Jul. 26, 2016

(54) ANTI-TUMOR NECROSIS FACTOR-ALPHA AGENTS AND USES THEREOF

(71) Applicant: TECHNOPHAGE, INVESTIGAÇÃO E DESENVOLVIMENTO EM BIOTECNOLOGIA, SA, Lisbon (PT)

(72) Inventors: Frederico Nuno Castanheira Aires da Silva, Lisbon (PT); Sofia Volker Corte-Real, Cruz Quebrada (PT); Rui Pedro da Silva Albuquerque e Freitas, Viseu (PT); Sara Ferreira Llorente Grancho Lourenço, Massama (PT)

(73) Assignee: Technophage, Investigacao E Desenvolvimento Em Biotecnologia, SA, Lisboa (PT)

( * ) Notice: Subject to any disclaimer, the term of this patent is extended or adjusted under 35 U.S.C. 154(b) by 43 days.

(21) Appl. No.: 14/346,151

(22) PCT Filed: Sep. 19, 2012

(86) PCT No.: PCT/PT2012/000035
§ 371 (c)(1),
(2) Date: Mar. 20, 2014

(87) PCT Pub. No.: WO2013/043070
PCT Pub. Date: Mar. 28, 2013

(65) Prior Publication Data
US 2015/0037349 A1 Feb. 5, 2015

Related U.S. Application Data

(60) Provisional application No. 61/538,548, filed on Sep. 23, 2011.

(51) Int. Cl.
*A61K 39/395* (2006.01)
*A61P 37/00* (2006.01)
*C07K 16/24* (2006.01)
*C07K 14/315* (2006.01)
*C12P 21/08* (2006.01)
*A61K 39/00* (2006.01)

(52) U.S. Cl.
CPC .......... *C07K 16/241* (2013.01); *C07K 14/315* (2013.01); *A61K 2039/505* (2013.01); *C07K 2317/35* (2013.01); *C07K 2317/515* (2013.01); *C07K 2317/56* (2013.01); *C07K 2317/567* (2013.01); *C07K 2317/569* (2013.01); *C07K 2317/76* (2013.01); *C07K 2317/92* (2013.01); *C07K 2317/94* (2013.01); *C07K 2319/00* (2013.01); *C07K 2319/21* (2013.01); *C07K 2319/31* (2013.01); *C07K 2319/42* (2013.01); *C07K 2319/43* (2013.01); *C07K 2319/70* (2013.01)

(58) Field of Classification Search
None
See application file for complete search history.

(56) References Cited

U.S. PATENT DOCUMENTS

| 6,267,964 | B1 * | 7/2001 | Nygren | A61K 47/4833 424/192.1 |
|---|---|---|---|---|
| 7,125,689 | B2 * | 10/2006 | Carr | C07K 14/3153 424/133.1 |
| 2007/0202105 | A1 | 8/2007 | Doyle et al. | |
| 2010/0137213 | A1 | 6/2010 | Fernandez et al. | |

FOREIGN PATENT DOCUMENTS

| WO | WO 2006/122786 | 11/2006 |
|---|---|---|
| WO | WO 2007/087673 | 8/2007 |
| WO | WO 2010/017595 | 2/2010 |
| WO | WO 2012/131053 | 10/2012 |

OTHER PUBLICATIONS

U.S. Appl. No. 14/346,126, filed Mar. 20, 2014.*
Allen Nguyen et al., "The Pharmacokinetics of an Albumin-Binding Fab (AB.Fab) can be Modulated as a Function of Affinity for Albumin," Protein Engineering, Design & Selection, vol. 19, No. 7, pp. 291-297, Apr. 18, 2006.
Hans Jonsson et al., "A Protein G-Related Cell Surface Protein in *Streptococcus zooepidemicus*," Infection and Immunity, vol. 63, No. 8, pp. 2968-2975, Aug. 1995.
Technophage, Investigação E Desenvolvimento Em Biotecnologia, SA, Search Report for Singapore Patent Application No. 11201400879S, 10 pages, Dec. 14, 2014.
Dennis et al., "Albumin Binding as a General Strategy for Improving the Pharmacokinetics of Proteins," Journal of Biological Chemistry, vol. 277, No. 38, pp. 35035-35043, Sep. 20, 2002.
König et al., "Use of Albumin-Binding Domain for the Selective Immobilisation of Recombinant Capture Antibody Fragments on ELISA Plates," Journal of Immunological Methods, vol. 218, No. 1-2, pp. 73-83, Sep. 1, 1998.
Kontermann, "Strategies for Extended Serum Half-Life of Protein Therapeutics," Current Opinion in Biotechnology, vol. 22, No. 6, pp. 868-876, Aug. 20, 2011.
Müller et al., "Improved Pharmacokinetics of Recombinant Bispecific Antibody Molecules by Fusion to Human Serum Albumin," Journal of Biological Chemistry, vol. 282, No. 17, pp. 12650-12660, Apr. 27, 2007.

\* cited by examiner

*Primary Examiner* — David Romeo
(74) *Attorney, Agent, or Firm* — Margaret B. Brivanlou; Nicole Fortune; King & Spalding LLP

(57) ABSTRACT

The present invention relates to polypeptides comprising one or more antibody single domains, or antigen-binding fragments thereof, directed against Tumor Necrosis Factor-alpha, in particular, two light chain variable domains in dimeric form, where the dimer has high solubility. It also relates to methods of using anti-Tumor Necrosis Factor-alpha polypeptides in treating inflammatory disorders, including rheumatoid arthritis. Compositions and methods for enhancing therapeutic potential of anti-Tumor Necrosis Factor-alpha polypeptides are provided, including linking the polypeptide to an albumin-binding domain and/or de-immunizing the polypeptide, to provide therapeutic agents with good solubility, enhanced serum half-life, and/or reduced immunogenicity, while substantially maintaining the specific binding properties of the anti-Tumor Necrosis Factor-alpha polypeptides.

24 Claims, 30 Drawing Sheets

FIG. 1

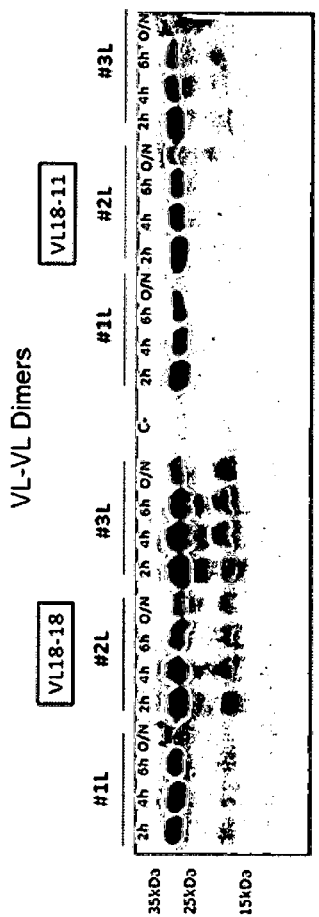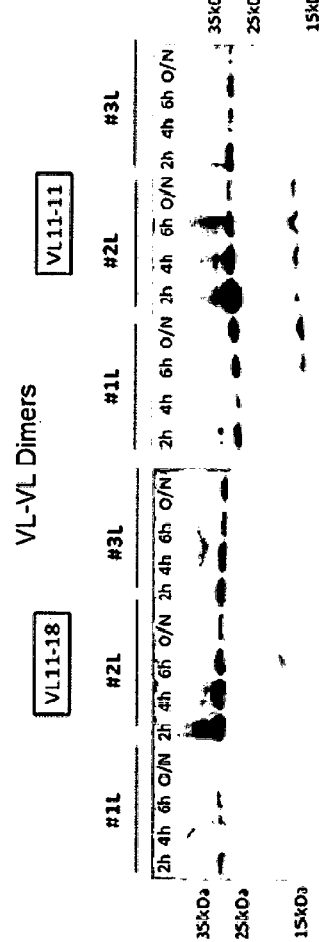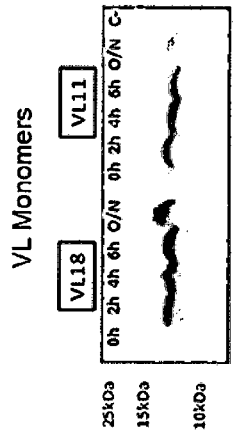
FIG. 2A
FIG. 2B
FIG. 2C

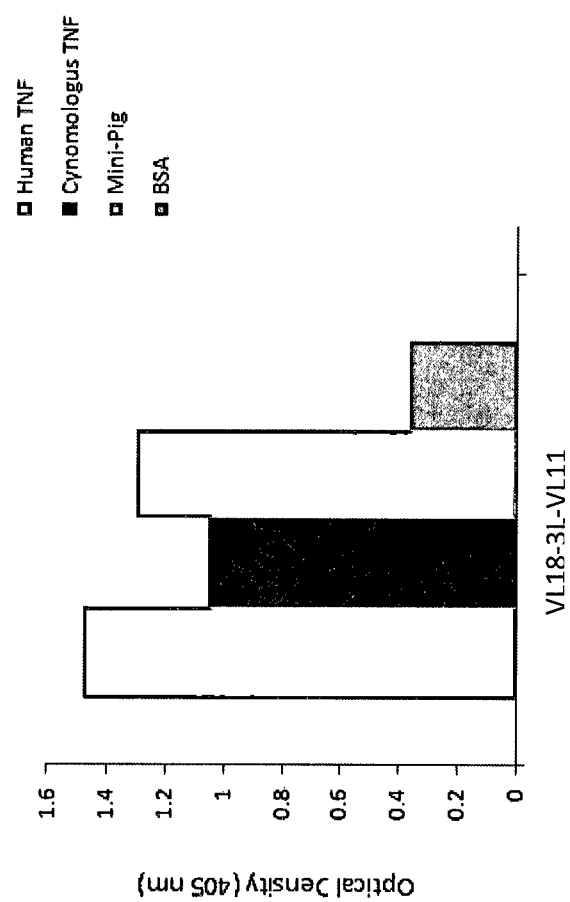

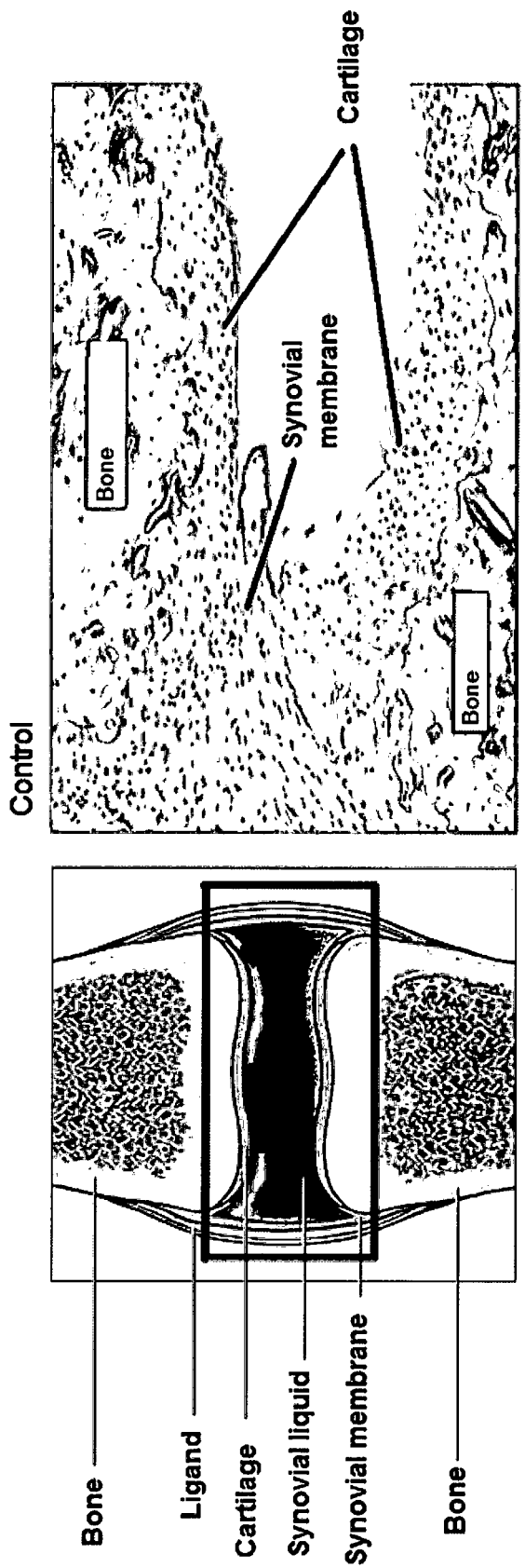

FIG. 12A

```
Ordinal    1           10          20          30          40          50          60
Kabat      1           10          20          30          40          50          60
VL18       ELVLTQTPASVEAAVGGTVTIKCQASQSISSYLAWYQQKPGHPPKLLIYKASTLASGVSS
                                         xxxxxxxxxx                  xxxxxxx Ordinal    61          70          80          90     abcd 100         110
Kabat      61          70          80          90          100
VL18       RFKGSGSGTEFTLTISDLECADAATYYCQSTYLGGTYVGGAFGGGTELEIL
                                         xxxxxxxxxxxxx
```

FIG. 12B

```
Ordinal    131         140         150         160         170         180         190
Kabat      1           10          20          30          40          50          60
VL11       ELVMTQTPPASVEAAVGGTVTIKCQASQSISRYLAWYQQRPGQPPKLLIYRASTLASGVSS
                                         xxxxxxxxxx                  xxxxxxx Ordinal    191         200         210         220         230     abc 240
Kabat      61          70          80          90          100
VL11       RFKGSGSGTEFTLTISDLECADAATYYCQSTYVNEGSVAAFGGGTEVVVK
                                         xxxxxxxxxxxxx
``` pep
Ordinal   250        260        270        280        290        300
pep       DITGAALLEAKAAINELKQYGISDYYVELINKAKTVEGVNALKAEILSALP

FIG. 12C

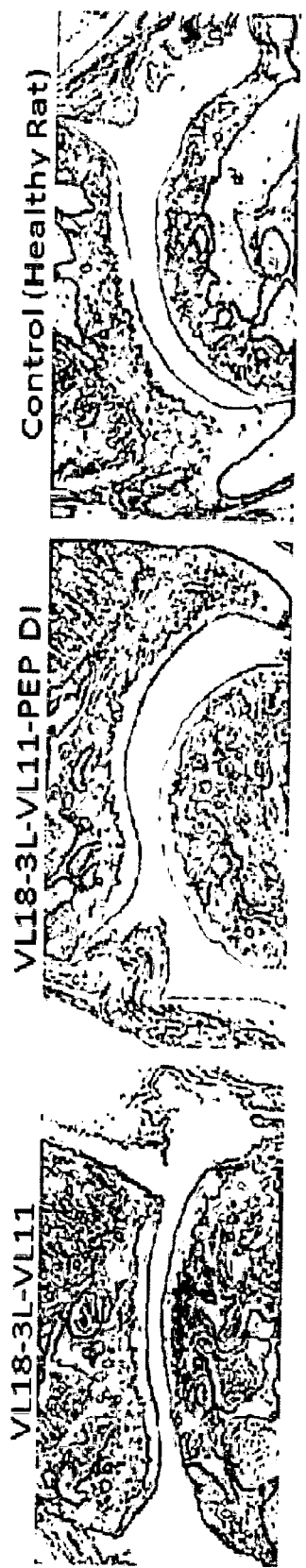
FIG. 17A
FIG. 17B
FIG. 17C
FIG. 17D
FIG. 17E
FIG. 17F

SEQUENCE LISTING

```
<160> NUMBER OF SEQ ID NOS: 62

<210> SEQ ID NO 1
<211> LENGTH: 111
<212> TYPE: PRT
<213> ORGANISM: Unknown
<220> FEATURE:
<223> OTHER INFORMATION: Description of Unknown: Rabbit polypeptide

<400> SEQUENCE: 1

Glu Leu Val Leu Thr Gln Thr Pro Ala Ser Val Glu Ala Ala Val Gly
1               5                   10                  15
```

```
Gly Thr Val Thr Ile Lys Cys Gln Ala Ser Gln Ser Ile Ser Ser Tyr
            20                  25                  30

Leu Ala Trp Tyr Gln Gln Lys Pro Gly His Pro Pro Lys Leu Leu Ile
        35                  40                  45

Tyr Lys Ala Ser Thr Leu Ala Ser Gly Val Ser Arg Phe Lys Gly
50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Ser Thr Tyr Leu Gly Gly Thr
                85                  90                  95

Tyr Val Gly Gly Ala Phe Gly Gly Gly Thr Glu Leu Glu Ile Leu
                100                 105                 110

<210> SEQ ID NO 2
<211> LENGTH: 110
<212> TYPE: PRT
<213> ORGANISM: Unknown
<220> FEATURE:
<223> OTHER INFORMATION: Description of Unknown: Rabbit polypeptide

<400> SEQUENCE: 2

Glu Leu Val Met Thr Gln Thr Pro Ala Ser Val Glu Ala Ala Val Gly
1               5                   10                  15

Gly Thr Val Thr Ile Lys Cys Gln Ala Ser Gln Ser Ile Ser Arg Tyr
            20                  25                  30

Leu Ala Trp Tyr Gln Gln Lys Pro Gly Gln Pro Pro Lys Leu Leu Ile
        35                  40                  45

Tyr Arg Ala Ser Thr Leu Ala Ser Gly Val Ser Ser Arg Phe Lys Gly
50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Ser Thr Tyr Val Asn Arg Gly
                85                  90                  95

Ser Val Ala Ala Phe Gly Gly Gly Thr Glu Val Val Val Lys
                100                 105                 110

<210> SEQ ID NO 3
<211> LENGTH: 107
<212> TYPE: PRT
<213> ORGANISM: Unknown
<220> FEATURE:
<223> OTHER INFORMATION: Description of Unknown: Rabbit polypeptide

<400> SEQUENCE: 3

Glu Leu Val Leu Thr Gln Thr Pro Ser Ser Val Ser Ala Ala Val Gly
1               5                   10                  15

Gly Thr Val Thr Ile Asn Cys Gln Ala Ser Glu Ser Ile Gly Asn Tyr
            20                  25                  30

Leu Ala Trp Tyr Gln Gln Lys Pro Gly Gln Pro Pro Lys Leu Leu Leu
        35                  40                  45

Tyr Ser Ala Ser Thr Leu Glu Ser Gly Val Pro Ser Arg Phe Arg Gly
50                  55                  60

Ser Gly Ser Gly Thr Glu Phe Thr Leu Thr Ile Ser Gly Met Lys Ala
65                  70                  75                  80

Glu Asp Ala Ala Thr Tyr Tyr Cys Gln Ser Gly Tyr Tyr Ser Ala Leu
                85                  90                  95

Thr Phe Gly Ala Gly Thr Asn Val Glu Ile Lys
```

100                 105

<210> SEQ ID NO 4
<211> LENGTH: 111
<212> TYPE: PRT
<213> ORGANISM: Unknown
<220> FEATURE:
<223> OTHER INFORMATION: Description of Unknown: Rabbit polypeptide

<400> SEQUENCE: 4

Glu Leu Asp Met Thr Gln Thr Pro Ala Ser Val Ser Ala Ala Val Gly
1               5                   10                  15

Gly Thr Val Thr Ile Asn Cys Gln Ala Ser Gln Asn Ile Tyr Ser Asn
            20                  25                  30

Leu Ala Trp Tyr Gln Gln Lys Pro Gly Gln Arg Pro Lys Leu Leu Ile
        35                  40                  45

Tyr Ala Ala Ser Asn Leu Ala Ser Gly Val Pro Ser Arg Phe Ser Gly
    50                  55                  60

Ser Gly Ser Gly Thr Asp Phe Thr Leu Thr Ile Ser Asp Leu Glu Cys
65                  70                  75                  80

Ala Asp Ala Ala Thr Tyr Tyr Cys Gln Ser Tyr Tyr Ser Ser Ser Ser
                85                  90                  95

Arg Tyr Gly Asn Gly Phe Gly Gly Gly Thr Glu Leu Glu Ile Leu
            100                 105                 110

<210> SEQ ID NO 5
<211> LENGTH: 110
<212> TYPE: PRT
<213> ORGANISM: Unknown
<220> FEATURE:
<223> OTHER INFORMATION: Description of Unknown: Rabbit polypeptide

<400> SEQUENCE: 5

Glu Leu Val Leu Thr Gln Thr Pro Ala Ser Val Ser Ala Ala Val Gly
1               5                   10                  15

Gly Thr Val Thr Ile Asn Cys Gln Ala Ser Gln Asn Ile Ser Ser Trp
            20                  25                  30

Leu Ser Trp Tyr Gln Gln Lys Pro Gly Gln Pro Pro Lys Leu Leu Ile
        35                  40                  45

Tyr Arg Ala Ser Thr Leu Ala Ser Gly Val Pro Ser Arg Phe Lys Gly
    50                  55                  60

Ser Gly Ser Gly Thr Gln Phe Thr Leu Thr Ile Ser Asp Leu Glu Cys
65                  70                  75                  80

Asp Asp Ala Ala Thr Tyr Tyr Cys Gln Gln Thr Tyr Thr Tyr Thr Asn
                85                  90                  95

Ile Glu Asn Ala Phe Gly Gly Gly Thr Glu Leu Glu Ile Leu
            100                 105                 110

<210> SEQ ID NO 6
<211> LENGTH: 108
<212> TYPE: PRT
<213> ORGANISM: Unknown
<220> FEATURE:
<223> OTHER INFORMATION: Description of Unknown: Rabbit polypeptide

<400> SEQUENCE: 6

Glu Leu Val Met Thr Gln Thr Pro Ala Ser Val Ser Glu Pro Val Gly
1               5                   10                  15

Gly Thr Val Thr Ile Lys Cys Gln Ala Ser Gln Ser Ile Ser Asn Leu
            20                  25                  30

Leu Ala Trp Tyr Gln Gln Lys Pro Gly Gln Pro Pro Lys Leu Leu Ile
        35                  40                  45

Tyr Lys Ala Ser Thr Leu Ala Ser Gly Val Ser Ser Arg Phe Lys Gly
    50                  55                  60

Ser Gly Ser Gly Thr Glu Phe Thr Leu Thr Ile Ser Gly Val Gln Cys
65                  70                  75                  80

Asp Asp Ala Ala Thr Tyr Ala Cys Gln Cys Thr Gly Tyr Gly Ser Asp
                85                  90                  95

Trp Ala Phe Gly Gly Gly Thr Glu Val Val Val Lys
            100                 105

<210> SEQ ID NO 7
<211> LENGTH: 108
<212> TYPE: PRT
<213> ORGANISM: Unknown
<220> FEATURE:
<223> OTHER INFORMATION: Description of Unknown: Rabbit polypeptide

<400> SEQUENCE: 7

Glu Leu Val Leu Thr Gln Thr Pro Ser Ser Val Ser Ala Ala Val Gly
1               5                   10                  15

Gly Thr Val Thr Ile Asn Cys Gln Ala Ser Gln Ser Val Ser Asn Leu
            20                  25                  30

Leu Ala Trp Tyr Gln Gln Lys Pro Gly Gln Pro Pro Lys Leu Leu Ile
        35                  40                  45

Tyr Gly Ala Ser Asn Leu Glu Ser Gly Val Pro Ser Arg Phe Arg Gly
    50                  55                  60

Ser Gly Ser Gly Thr Glu Phe Thr Leu Thr Ile Ser Gly Met Lys Ala
65                  70                  75                  80

Glu Asp Ala Ala Thr Tyr Tyr Cys Gln Ser Gly Tyr Tyr Ser Ala Gly
                85                  90                  95

Ala Thr Phe Gly Ala Gly Thr Asn Val Glu Ile Lys
            100                 105

<210> SEQ ID NO 8
<211> LENGTH: 107
<212> TYPE: PRT
<213> ORGANISM: Unknown
<220> FEATURE:
<223> OTHER INFORMATION: Description of Unknown: Rabbit polypeptide

<400> SEQUENCE: 8

Glu Leu Asp Leu Thr Gln Thr Pro Ser Ser Val Ser Ala Ala Val Gly
1               5                   10                  15

Gly Thr Val Thr Ile Asn Cys Gln Ala Ser Gln Ser Val Ser Asn Leu
            20                  25                  30

Leu Ala Trp Tyr Gln Gln Lys Pro Gly Gln Pro Pro Lys Leu Leu Ile
        35                  40                  45

Tyr Gly Ala Ser Asn Leu Glu Ser Gly Val Pro Ser Arg Phe Arg Gly
    50                  55                  60

Ser Gly Ser Gly Thr Glu Phe Thr Leu Thr Ile Ser Gly Met Lys Ala
65                  70                  75                  80

Glu Asp Ala Ala Thr Tyr Tyr Cys Gln Ser Gly Tyr Tyr Ser Ala Leu
                85                  90                  95

Thr Phe Gly Ala Gly Thr Asn Val Glu Ile Lys
            100                 105

```
<210> SEQ ID NO 9
<211> LENGTH: 111
<212> TYPE: PRT
<213> ORGANISM: Unknown
<220> FEATURE:
<223> OTHER INFORMATION: Description of Unknown: Rabbit polypeptide

<400> SEQUENCE: 9

Glu Leu Val Met Thr Gln Thr Pro Ser Ser Val Ser Ala Ala Val Gly
1               5                   10                  15

Gly Thr Val Thr Ile Asn Cys Gln Ala Ser Pro Ser Val Tyr Lys Asn
            20                  25                  30

Tyr Leu Ala Trp Phe Gln Gln Lys Pro Gly Gln Pro Pro Lys Leu Leu
        35                  40                  45

Ile Tyr Leu Thr Ser Thr Leu Ala Ser Gly Val Pro Ser Arg Phe Lys
    50                  55                  60

Gly Ser Gly Ser Gly Thr Glu Phe Thr Leu Thr Ile Ser Asp Val Gln
65                  70                  75                  80

Cys Asp Asp Ala Ala Thr Tyr Tyr Cys Leu Gly Gly Tyr Gly Asp Ile
                85                  90                  95

Asp Asp Thr His Thr Phe Gly Gly Gly Thr Glu Leu Glu Ile Leu
            100                 105                 110

<210> SEQ ID NO 10
<211> LENGTH: 106
<212> TYPE: PRT
<213> ORGANISM: Unknown
<220> FEATURE:
<223> OTHER INFORMATION: Description of Unknown: Rabbit polypeptide

<400> SEQUENCE: 10

Glu Leu Val Met Thr Gln Thr Pro Ser Ser Val Ser Ala Ala Val Gly
1               5                   10                  15

Gly Thr Val Thr Ile Lys Cys Gln Ala Ser Gln Ser Val Asn Asn Tyr
            20                  25                  30

Leu Ala Trp Tyr Arg His Lys Pro Arg Gln Pro Pro Gln Leu Leu Ile
        35                  40                  45

Gly Ala Ser Asn Leu Glu Ser Gly Val Ala Ser Trp Phe Arg Gly Arg
    50                  55                  60

Gly Ser Gly Thr Gly Ile Asn Leu Thr Ile Thr Gly Met Lys Ala Glu
65                  70                  75                  80

Asp Val Ala Ala Tyr Tyr Cys Tyr Arg His Ser Asn Cys Tyr Leu Thr
                85                  90                  95

Phe Gly Ala Gly Thr Asn Val Glu Ile Lys
            100                 105

<210> SEQ ID NO 11
<211> LENGTH: 109
<212> TYPE: PRT
<213> ORGANISM: Unknown
<220> FEATURE:
<223> OTHER INFORMATION: Description of Unknown: Rabbit polypeptide

<400> SEQUENCE: 11

Glu Leu Asp Leu Thr Gln Thr Pro Ser Leu Ser Ala Ser Val Gly
1               5                   10                  15

Glu Thr Val Arg Ile Arg Cys Leu Ala Ser Glu Asp Ile Tyr Ser Gly
            20                  25                  30

Ile Ser Trp Tyr Gln Gln Lys Pro Glu Lys Pro Pro Arg Leu Leu Ile
        35                  40                  45
```

```
Ser Gly Ala Ser Arg Leu Glu Ser Gly Val Pro Pro Arg Phe Ser Gly
        50                  55                  60

Ser Gly Ser Gly Thr Asp Tyr Thr Leu Thr Ile Gly Gly Val Gln Thr
 65                  70                  75                  80

Glu Asp Ala Ala Thr Tyr Tyr Cys Leu Gly Gly Ser Tyr Gly Ser Thr
                85                  90                  95

Gly Met Thr Phe Gly Ala Gly Thr Asn Val Glu Ile Lys
            100                 105
```

<210> SEQ ID NO 12
<211> LENGTH: 109
<212> TYPE: PRT
<213> ORGANISM: Unknown
<220> FEATURE:
<223> OTHER INFORMATION: Description of Unknown: Rabbit polypeptide

<400> SEQUENCE: 12

```
Glu Leu Val Met Thr Gln Thr Pro Ser Leu Ser Ala Ser Val Gly
 1               5                  10                  15

Glu Thr Val Arg Ile Arg Cys Leu Ala Ser Glu Asp Ile Tyr Ser Gly
                20                  25                  30

Ile Ser Trp Tyr Gln Gln Lys Pro Gly Lys Pro Thr Leu Leu Ile
            35                  40                  45

Tyr Gly Ala Ser Asn Leu Glu Ser Gly Val Pro Pro Arg Phe Ser Gly
        50                  55                  60

Ser Gly Ser Gly Thr Asp Tyr Thr Leu Thr Ile Gly Gly Val Gln Ala
 65                  70                  75                  80

Glu Asp Ala Ala Thr Tyr Tyr Cys Leu Gly Gly Tyr Thr Tyr Ser Gly
                85                  90                  95

Thr Leu Thr Phe Gly Ala Gly Thr Asn Val Glu Ile Lys
            100                 105
```

<210> SEQ ID NO 13
<211> LENGTH: 111
<212> TYPE: PRT
<213> ORGANISM: Unknown
<220> FEATURE:
<223> OTHER INFORMATION: Description of Unknown: Rabbit polypeptide

<400> SEQUENCE: 13

```
Glu Leu Val Met Thr Gln Thr Pro Ala Ser Val Ser Ala Ala Val Gly
 1               5                  10                  15

Gly Thr Val Thr Ile Asn Cys Gln Ala Ser Gln Ser Ile Gly Asn Asn
                20                  25                  30

Tyr Leu Cys Trp Tyr Gln Lys Lys Arg Gly Pro Pro Met Leu Leu
            35                  40                  45

Ile Tyr Lys Ala Ser Pro Leu Ala Ser Gly Val Pro Ser Arg Phe Glu
        50                  55                  60

Gly Gly Gly Ser Gly Thr Glu Tyr Pro Leu Thr Ile Gly Gly Val Arg
 65                  70                  75                  80

Gly Asp Asp Ala Ala Ser Tyr Cys Cys Gln Gly Tyr Ile Gly Tyr Asn
                85                  90                  95

Asn Asp Asp His Ala Phe Gly Gly Gly Thr Glu Val Val Val Lys
            100                 105                 110
```

<210> SEQ ID NO 14
<211> LENGTH: 112
<212> TYPE: PRT

```
<213> ORGANISM: Unknown
<220> FEATURE:
<223> OTHER INFORMATION: Description of Unknown: Rabbit polypeptide

<400> SEQUENCE: 14

Glu Leu Val Leu Thr Gln Thr Pro Ala Ser Val Glu Ala Ala Val Gly
1               5                   10                  15

Gly Thr Val Thr Ile Lys Cys Gln Ala Ser Glu Ser Ile Ser Asn Tyr
            20                  25                  30

Leu Ala Trp Tyr Gln Gln Lys Pro Gly Gln Pro Pro Lys Leu Leu Ile
        35                  40                  45

Tyr Ser Ala Ser Thr Leu Ala Ser Gly Val Pro Ser Arg Phe Ser Gly
50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Cys Thr Val Ala Ile Ser Gly
                85                  90                  95

Asn Ser Tyr Gly Asn Ala Phe Gly Gly Gly Thr Glu Val Val Lys
            100                 105                 110

<210> SEQ ID NO 15
<211> LENGTH: 108
<212> TYPE: PRT
<213> ORGANISM: Unknown
<220> FEATURE:
<223> OTHER INFORMATION: Description of Unknown: Rabbit polypeptide

<400> SEQUENCE: 15

Glu Leu Asp Leu Thr Gln Thr Pro Ser Ser Val Ser Ala Ala Val Gly
1               5                   10                  15

Gly Thr Val Thr Ile Asn Cys Gln Ala Ser Gln Ser Val Ser Asn Leu
            20                  25                  30

Leu Ala Trp Tyr Gln Gln Lys Pro Gly Gln Pro Pro Lys Leu Leu Ile
        35                  40                  45

Tyr Gly Ala Ser Asn Leu Glu Ser Gly Val Pro Ser Arg Phe Arg Gly
50                  55                  60

Ser Gly Ser Gly Thr Glu Phe Thr Leu Thr Ile Ser Gly Met Lys Ala
65                  70                  75                  80

Glu Asp Ala Ala Thr Tyr Tyr Cys Gln Ser Gly Tyr Tyr Ser Ala Gly
                85                  90                  95

Ala Thr Phe Gly Ala Gly Thr Asn Val Glu Ile Lys
            100                 105

<210> SEQ ID NO 16
<211> LENGTH: 107
<212> TYPE: PRT
<213> ORGANISM: Unknown
<220> FEATURE:
<223> OTHER INFORMATION: Description of Unknown: Rabbit polypeptide

<400> SEQUENCE: 16

Glu Leu Val Met Thr Gln Thr Pro Ala Ser Val Ser Glu Pro Val Gly
1               5                   10                  15

Gly Thr Val Thr Ile Lys Cys Gln Ala Ser Gln Ser Ile Tyr Ser Tyr
            20                  25                  30

Leu Ser Trp Tyr Gln Gln Lys Pro Gly Gln Arg Pro Lys Leu Leu Ile
        35                  40                  45

Tyr Glu Ala Ser Lys Leu Ala Ser Gly Val Pro Ser Arg Phe Ser Gly
50                  55                  60
```

```
Ser Gly Ser Gly Thr Glu Phe Thr Leu Thr Ile Ser Asp Leu Glu Cys
 65                  70                  75                  80

Ala Asp Ala Ala Thr Tyr Tyr Cys Gln Tyr Ser Gly Gly Ser Ile Tyr
                 85                  90                  95

Ser Phe Gly Gly Gly Thr Glu Leu Glu Ile Leu
                100                 105
```

<210> SEQ ID NO 17
<211> LENGTH: 110
<212> TYPE: PRT
<213> ORGANISM: Unknown
<220> FEATURE:
<223> OTHER INFORMATION: Description of Unknown: Rabbit polypeptide

<400> SEQUENCE: 17

```
Glu Leu Asp Leu Thr Gln Thr Pro Ala Ser Val Glu Ala Ala Val Gly
  1               5                  10                  15

Gly Thr Val Thr Ile Lys Cys Gln Ala Ser Gln Ser Ile Ser Ser Tyr
                 20                  25                  30

Leu Ala Trp Tyr Gln Gln Lys Pro Gly Gln Pro Pro Lys Leu Leu Ile
             35                  40                  45

Tyr Arg Ala Ser Thr Leu Ala Ser Gly Val Ser Ser Arg Phe Ser Gly
 50                  55                  60

Ser Gly Ser Gly Thr Glu Phe Thr Leu Thr Ile Ser Asp Leu Glu Cys
 65                  70                  75                  80

Ala Asp Ala Ala Thr Tyr Tyr Cys Gln Cys Thr Tyr Ala Gly Ser Ser
                 85                  90                  95

Tyr Gly Asn Thr Phe Gly Gly Gly Thr Glu Val Val Val Lys
                100                 105                 110
```

<210> SEQ ID NO 18
<211> LENGTH: 109
<212> TYPE: PRT
<213> ORGANISM: Unknown
<220> FEATURE:
<223> OTHER INFORMATION: Description of Unknown: Rabbit polypeptide

<400> SEQUENCE: 18

```
Glu Leu Asp Met Thr Gln Thr Pro Ser Pro Val Ser Gly Ala Val Gly
  1               5                  10                  15

Gly Thr Val Thr Ile Lys Cys Gln Ala Ser Gln Asn Ile Ile Gly Tyr
                 20                  25                  30

Leu Ser Trp Tyr Gln Gln Lys Pro Gly Gln Pro Pro Lys Leu Leu Ile
             35                  40                  45

Tyr Arg Ala Ser Thr Leu Ala Ser Gly Val Pro Ser Arg Phe Ser Gly
 50                  55                  60

Ser Gly Ser Gly Thr Gln Phe Thr Leu Thr Ile Ser Asp Val Gln Cys
 65                  70                  75                  80

Asp Asp Ala Ala Thr Tyr Tyr Cys Ala Gly Asp Tyr Thr Asp Asn Ser
                 85                  90                  95

Asp Asn Ala Phe Gly Gly Gly Thr Glu Val Val Val Lys
                100                 105
```

<210> SEQ ID NO 19
<211> LENGTH: 111
<212> TYPE: PRT
<213> ORGANISM: Unknown
<220> FEATURE:
<223> OTHER INFORMATION: Description of Unknown: Rabbit polypeptide

<400> SEQUENCE: 19

```
Glu Leu Val Leu Thr Gln Gln Pro Ala Ser Val Glu Ala Ala Pro Gly
1               5                   10                  15

Gly Thr Val Thr Ile Lys Cys Gln Ala Ser Gln Ser Ile Ser Ser Tyr
            20                  25                  30

Leu Ala Trp Tyr Gln Gln Lys Pro Gly His Pro Pro Lys Leu Leu Ile
        35                  40                  45

Tyr Lys Val Ser Thr Arg Ala Ser Gly Val Ser Arg Phe Ser Gly
50                  55                  60

Ser Gly Ser Gly Thr Glu Phe Thr Leu Thr Ile Ser Asp Leu Lys Ser
65                  70                  75                  80

Ala Asp Ala Ala Thr Tyr Tyr Cys Gln Ser Ala Tyr Leu Gly Gly Thr
                85                  90                  95

Tyr Val Gly Gly Ala Phe Gly Gly Gly Thr Glu Leu Glu Ile Lys
            100                 105                 110
```

<210> SEQ ID NO 20
<211> LENGTH: 111
<212> TYPE: PRT
<213> ORGANISM: Unknown
<220> FEATURE:
<223> OTHER INFORMATION: Description of Unknown: Rabbit polypeptide

<400> SEQUENCE: 20

```
Glu Leu Val Leu Thr Gln Gln Pro Ala Ser Val Glu Ala Ala Pro Gly
1               5                   10                  15

Gly Thr Val Thr Ile Lys Cys Gln Ala Ser Gln Ser Ile Ser Ser Tyr
            20                  25                  30

Leu Ala Trp Tyr Gln Gln Lys Pro Gly His Pro Pro Lys Leu Leu Ile
        35                  40                  45

Tyr Lys Val Ser Thr Glu Ala Ser Gly Val Ser Ser Arg Phe Ser Gly
50                  55                  60

Ser Gly Ser Gly Thr Glu Phe Thr Leu Thr Ile Ser Asp Leu Lys Ser
65                  70                  75                  80

Ala Asp Ala Ala Thr Tyr Tyr Cys Gln Ser Ala Tyr Leu Gly Gly Thr
                85                  90                  95

Tyr Val Gly Gly Ala Phe Gly Gly Gly Thr Glu Leu Glu Ile Lys
            100                 105                 110
```

<210> SEQ ID NO 21
<211> LENGTH: 111
<212> TYPE: PRT
<213> ORGANISM: Unknown
<220> FEATURE:
<223> OTHER INFORMATION: Description of Unknown: Rabbit polypeptide

<400> SEQUENCE: 21

```
Glu Leu Val Leu Thr Gln Gln Pro Ala Ser Val Glu Ala Ala Pro Gly
1               5                   10                  15

Gly Thr Val Thr Ile Lys Cys Gln Ala Ser Gln Ser Ile Ser Ser Tyr
            20                  25                  30

Leu Ala Trp Tyr Gln Gln Lys Pro Gly His Pro Pro Lys Leu Leu Ile
        35                  40                  45

Tyr Lys Val Ser Thr Arg Ala Ser Gly Val Ser Ser Arg Phe Ser Gly
50                  55                  60

Ser Gly Ser Gly Thr Glu Phe Thr Leu Thr Ile Ser Asp Leu Lys Ser
65                  70                  75                  80
```

```
Ala Asp Ala Ala Thr Tyr Tyr Cys Gln Ser Thr Tyr Leu Gly Gly Thr
                85                  90                  95

Tyr Val Gly Gly Ala Phe Gly Gly Gly Thr Glu Leu Glu Ile Lys
            100                 105                 110

<210> SEQ ID NO 22
<211> LENGTH: 111
<212> TYPE: PRT
<213> ORGANISM: Unknown
<220> FEATURE:
<223> OTHER INFORMATION: Description of Unknown: Rabbit polypeptide

<400> SEQUENCE: 22

Glu Leu Val Leu Thr Gln Gln Pro Ala Ser Val Glu Ala Ala Pro Gly
1               5                   10                  15

Gly Thr Val Thr Ile Lys Cys Gln Ala Ser Gln Ser Ile Ser Ser Tyr
            20                  25                  30

Leu Ala Trp Tyr Gln Gln Lys Pro Gly His Pro Pro Lys Leu Leu Ile
        35                  40                  45

Tyr Lys Val Ser Thr Glu Ala Ser Gly Val Ser Ser Arg Phe Ser Gly
    50                  55                  60

Ser Gly Ser Gly Thr Glu Phe Thr Leu Thr Ile Ser Asp Leu Lys Ser
65                  70                  75                  80

Ala Asp Ala Ala Thr Tyr Tyr Cys Gln Ser Thr Tyr Leu Gly Gly Thr
                85                  90                  95

Tyr Val Gly Gly Ala Phe Gly Gly Gly Thr Glu Leu Glu Ile Lys
            100                 105                 110

<210> SEQ ID NO 23
<211> LENGTH: 111
<212> TYPE: PRT
<213> ORGANISM: Unknown
<220> FEATURE:
<223> OTHER INFORMATION: Description of Unknown: Rabbit polypeptide

<400> SEQUENCE: 23

Glu Leu Val Leu Thr Gln Gln Pro Ala Ser Val Glu Ala Ala Pro Gly
1               5                   10                  15

Gly Thr Val Thr Ile Lys Cys Gln Ala Ser Gln Ser Ile Ser Ser Tyr
            20                  25                  30

Leu Ala Trp Tyr Gln Gln Lys Pro Gly His Pro Pro Lys Leu Leu Ile
        35                  40                  45

Tyr Lys Ala Ser Thr Leu Ala Ser Gly Val Ser Ser Arg Phe Ser Gly
    50                  55                  60

Ser Gly Ser Gly Thr Glu Phe Thr Leu Thr Ile Ser Asp Leu Lys Ser
65                  70                  75                  80

Ala Asp Ala Ala Thr Tyr Tyr Cys Gln Ser Thr Tyr Leu Gly Gly Thr
                85                  90                  95

Tyr Val Gly Gly Ala Phe Gly Gly Gly Thr Glu Leu Glu Ile Lys
            100                 105                 110

<210> SEQ ID NO 24
<211> LENGTH: 110
<212> TYPE: PRT
<213> ORGANISM: Unknown
<220> FEATURE:
<223> OTHER INFORMATION: Description of Unknown: Rabbit polypeptide

<400> SEQUENCE: 24
```

-continued

Glu Leu Val Met Thr Gln Gln Pro Ala Ser Val Glu Ala Ala Pro Gly
1               5                   10                  15

Gly Thr Val Thr Ile Lys Cys Gln Ala Ser Gln Ser Ile Ser Ser Tyr
                20                  25                  30

Leu Ala Trp Tyr Gln Gln Lys Pro Gly Gln Pro Pro Lys Leu Leu Ile
            35                  40                  45

Tyr Arg Val Ser Thr Arg Ala Ser Gly Val Ser Ser Arg Phe Ser Gly
        50                  55                  60

Ser Gly Ser Gly Thr Glu Phe Thr Leu Thr Ile Ser Asp Leu Lys Ser
65                  70                  75                  80

Ala Asp Ala Ala Thr Tyr Tyr Cys Gln Ser Ala Tyr Val Asn Arg Gly
                85                  90                  95

Ser Val Ala Ser Phe Gly Gly Gly Thr Lys Val Val Val Lys
                100                 105                 110

<210> SEQ ID NO 25
<211> LENGTH: 110
<212> TYPE: PRT
<213> ORGANISM: Unknown
<220> FEATURE:
<223> OTHER INFORMATION: Description of Unknown: Rabbit polypeptide

<400> SEQUENCE: 25

Glu Leu Val Met Thr Gln Gln Pro Ala Ser Val Glu Ala Ala Pro Gly
1               5                   10                  15

Gly Thr Val Thr Ile Lys Cys Gln Ala Ser Gln Ser Ile Ser Ser Tyr
                20                  25                  30

Leu Ala Trp Tyr Gln Gln Lys Pro Gly Gln Pro Pro Lys Leu Leu Ile
            35                  40                  45

Tyr Arg Val Ser Thr Glu Ala Ser Gly Val Ser Ser Arg Phe Ser Gly
        50                  55                  60

Ser Gly Ser Gly Thr Glu Phe Thr Leu Thr Ile Ser Asp Leu Lys Ser
65                  70                  75                  80

Ala Asp Ala Ala Thr Tyr Tyr Cys Gln Ser Ala Tyr Val Asn Arg Gly
                85                  90                  95

Ser Val Ala Ser Phe Gly Gly Gly Thr Lys Val Val Val Lys
                100                 105                 110

<210> SEQ ID NO 26
<211> LENGTH: 110
<212> TYPE: PRT
<213> ORGANISM: Unknown
<220> FEATURE:
<223> OTHER INFORMATION: Description of Unknown: Rabbit polypeptide

<400> SEQUENCE: 26

Glu Leu Val Met Thr Gln Gln Pro Ala Ser Val Glu Ala Ala Pro Gly
1               5                   10                  15

Gly Thr Val Thr Ile Lys Cys Gln Ala Ser Gln Ser Ile Ser Ser Tyr
                20                  25                  30

Leu Ala Trp Tyr Gln Gln Lys Pro Gly Gln Pro Pro Lys Leu Leu Ile
            35                  40                  45

Tyr Arg Val Ser Thr Arg Ala Ser Gly Val Ser Ser Arg Phe Ser Gly
        50                  55                  60

Ser Gly Ser Gly Thr Glu Phe Thr Leu Thr Ile Ser Asp Leu Lys Ser
65                  70                  75                  80

Ala Asp Ala Ala Thr Tyr Tyr Cys Gln Ser Thr Tyr Val Asn Arg Gly
                85                  90                  95

```
Ser Val Ala Ala Phe Gly Gly Gly Thr Lys Val Val Val Lys
            100                 105                 110

<210> SEQ ID NO 27
<211> LENGTH: 110
<212> TYPE: PRT
<213> ORGANISM: Unknown
<220> FEATURE:
<223> OTHER INFORMATION: Description of Unknown: Rabbit polypeptide

<400> SEQUENCE: 27

Glu Leu Val Met Thr Gln Gln Pro Ala Ser Val Glu Ala Ala Pro Gly
1               5                   10                  15

Gly Thr Val Thr Ile Lys Cys Gln Ala Ser Gln Ser Ile Ser Ser Tyr
            20                  25                  30

Leu Ala Trp Tyr Gln Gln Lys Pro Gly Gln Pro Pro Lys Leu Leu Ile
        35                  40                  45

Tyr Arg Val Ser Thr Glu Ala Ser Gly Val Ser Ser Arg Phe Ser Gly
    50                  55                  60

Ser Gly Ser Gly Thr Glu Phe Thr Leu Thr Ile Ser Asp Leu Lys Ser
65                  70                  75                  80

Ala Asp Ala Ala Thr Tyr Tyr Cys Gln Ser Thr Tyr Val Asn Arg Gly
                85                  90                  95

Ser Val Ala Ala Phe Gly Gly Gly Thr Lys Val Val Val Lys
            100                 105                 110

<210> SEQ ID NO 28
<211> LENGTH: 110
<212> TYPE: PRT
<213> ORGANISM: Unknown
<220> FEATURE:
<223> OTHER INFORMATION: Description of Unknown: Rabbit polypeptide

<400> SEQUENCE: 28

Glu Leu Val Met Thr Gln Gln Pro Ala Ser Val Glu Ala Ala Pro Gly
1               5                   10                  15

Gly Thr Val Thr Ile Lys Cys Gln Ala Ser Gln Ser Ile Ser Ser Tyr
            20                  25                  30

Leu Ala Trp Tyr Gln Gln Lys Pro Gly Gln Pro Pro Lys Leu Leu Ile
        35                  40                  45

Tyr Arg Ala Ser Thr Leu Ala Ser Gly Val Ser Ser Arg Phe Ser Gly
    50                  55                  60

Ser Gly Ser Gly Thr Glu Phe Thr Leu Thr Ile Ser Asp Leu Lys Ser
65                  70                  75                  80

Ala Asp Ala Ala Thr Tyr Tyr Cys Gln Ser Thr Tyr Val Asn Arg Gly
                85                  90                  95

Ser Val Ala Ala Phe Gly Gly Gly Thr Lys Val Val Val Lys
            100                 105                 110

<210> SEQ ID NO 29
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ser Gly Gly Gly Gly Ser Gly Gly Gly Gly Ser Gly Gly Gly Ser
1               5                   10                  15
```

Ser Gly

<210> SEQ ID NO 30
<211> LENGTH: 52
<212> TYPE: PRT
<213> ORGANISM: Streptococcus zooepidemicus

<400> SEQUENCE: 30

```
Asp Ile Thr Gly Ala Ala Leu Leu Glu Ala Lys Glu Ala Ala Ile Asn
1               5                   10                  15

Glu Leu Lys Gln Tyr Gly Ile Ser Asp Tyr Tyr Val Thr Leu Ile Asn
            20                  25                  30

Lys Ala Lys Thr Val Glu Gly Val Asn Ala Leu Lys Ala Glu Ile Leu
        35                  40                  45

Ser Ala Leu Pro
        50
```

<210> SEQ ID NO 31
<211> LENGTH: 52
<212> TYPE: PRT
<213> ORGANISM: Streptococcus zooepidemicus

<400> SEQUENCE: 31

```
Asp Ile Thr Gly Ala Ala Leu Leu Glu Ala Lys Asp Ala Ala Ile Asn
1               5                   10                  15

Glu Leu Lys Gln Tyr Gly Ile Ser Asp Tyr Tyr Val His Leu Ile Asn
            20                  25                  30

Lys Ala Asp Thr Val Glu Gly Val Asn Ala Leu Lys Asp Glu Ile Leu
        35                  40                  45

Ser Ala Leu Pro
        50
```

<210> SEQ ID NO 32
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

```
Glu Leu Val Leu Thr Gln Thr Pro Ala Ser Val Glu Ala Ala Val Gly
1               5                   10                  15

Gly Thr Val Thr Ile Lys Cys Gln Ala Ser Gln Ser Ile Ser Ser Tyr
            20                  25                  30

Leu Ala Trp Tyr Gln Gln Lys Pro Gly His Pro Pro Lys Leu Leu Ile
        35                  40                  45

Tyr Lys Ala Ser Thr Leu Ala Ser Gly Val Ser Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Ser Thr Tyr Leu Gly Gly Thr
                85                  90                  95

Tyr Val Gly Gly Ala Phe Gly Gly Gly Thr Glu Leu Glu Ile Leu Ser
            100                 105                 110

Gly Gly Gly Gly Ser Gly Gly Gly Ser Gly Gly Gly Ser
        115                 120                 125

Gly Glu Leu Val Met Thr Gln Thr Pro Ala Ser Val Glu Ala Ala Val
```

```
Gly Gly Thr Val Thr Ile Lys Cys Gln Ala Ser Gln Ser Ile Ser Arg
145                 150                 155                 160

Tyr Leu Ala Trp Tyr Gln Gln Lys Pro Gly Gln Pro Pro Lys Leu Leu
                165                 170                 175

Ile Tyr Arg Ala Ser Thr Leu Ala Ser Gly Val Ser Ser Arg Phe Lys
            180                 185                 190

Gly Ser Gly Ser Gly Thr Glu Phe Thr Leu Thr Ile Ser Asp Leu Glu
        195                 200                 205

Cys Ala Asp Ala Ala Thr Tyr Tyr Cys Gln Ser Thr Tyr Val Asn Arg
    210                 215                 220

Gly Ser Val Ala Ala Phe Gly Gly Gly Thr Glu Val Val Val Lys
225                 230                 235

<210> SEQ ID NO 33
<211> LENGTH: 309
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Glu Leu Val Leu Thr Gln Thr Pro Ala Ser Val Glu Ala Ala Val Gly
1               5                   10                  15

Gly Thr Val Thr Ile Lys Cys Gln Ala Ser Gln Ser Ile Ser Ser Tyr
            20                  25                  30

Leu Ala Trp Tyr Gln Gln Lys Pro Gly His Pro Pro Lys Leu Leu Ile
        35                  40                  45

Tyr Lys Ala Ser Thr Leu Ala Ser Gly Val Ser Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Ser Thr Tyr Leu Gly Gly Thr
                85                  90                  95

Tyr Val Gly Gly Ala Phe Gly Gly Gly Thr Glu Leu Glu Ile Leu Ser
            100                 105                 110

Gly Gly Gly Gly Ser Gly Gly Gly Ser Gly Gly Gly Ser Ser
        115                 120                 125

Gly Glu Leu Val Met Thr Gln Thr Pro Ala Ser Val Glu Ala Ala Val
    130                 135                 140

Gly Gly Thr Val Thr Ile Lys Cys Gln Ala Ser Gln Ser Ile Ser Arg
145                 150                 155                 160

Tyr Leu Ala Trp Tyr Gln Gln Lys Pro Gly Gln Pro Pro Lys Leu Leu
                165                 170                 175

Ile Tyr Arg Ala Ser Thr Leu Ala Ser Gly Val Ser Ser Arg Phe Lys
            180                 185                 190

Gly Ser Gly Ser Gly Thr Glu Phe Thr Leu Thr Ile Ser Asp Leu Glu
        195                 200                 205

Cys Ala Asp Ala Ala Thr Tyr Tyr Cys Gln Ser Thr Tyr Val Asn Arg
    210                 215                 220

Gly Ser Val Ala Ala Phe Gly Gly Gly Thr Glu Val Val Val Lys Ser
225                 230                 235                 240

Gly Gly Gly Gly Ser Gly Gly Gly Ser Gly Gly Gly Ser Ser
            245                 250                 255
```

Gly Asp Ile Thr Gly Ala Ala Leu Leu Glu Ala Lys Asp Ala Ala Ile
            260                 265                 270

Asn Glu Leu Lys Gln Tyr Gly Ile Ser Asp Tyr Tyr Val His Leu Ile
        275                 280                 285

Asn Lys Ala Asp Thr Val Glu Gly Val Asn Ala Leu Lys Asp Glu Ile
    290                 295                 300

Leu Ser Ala Leu Pro
305

<210> SEQ ID NO 34
<211> LENGTH: 309
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Glu Leu Val Leu Thr Gln Thr Pro Ala Ser Val Glu Ala Ala Val Gly
1               5                   10                  15

Gly Thr Val Thr Ile Lys Cys Gln Ala Ser Gln Ser Ile Ser Ser Tyr
            20                  25                  30

Leu Ala Trp Tyr Gln Gln Lys Pro Gly His Pro Lys Leu Leu Ile
        35                  40                  45

Tyr Lys Ala Ser Thr Leu Ala Ser Gly Val Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Ser Thr Tyr Leu Gly Gly Thr
                85                  90                  95

Tyr Val Gly Gly Ala Phe Gly Gly Thr Glu Leu Glu Ile Leu Ser
            100                 105                 110

Gly Gly Gly Gly Ser Gly Gly Gly Gly Ser Gly Gly Gly Ser Ser
            115                 120                 125

Gly Glu Leu Val Met Thr Gln Thr Pro Ala Ser Val Glu Ala Ala Val
130                 135                 140

Gly Gly Thr Val Thr Ile Lys Cys Gln Ala Ser Gln Ser Ile Ser Arg
145                 150                 155                 160

Tyr Leu Ala Trp Tyr Gln Gln Lys Pro Gly Gln Pro Pro Lys Leu Leu
                165                 170                 175

Ile Tyr Arg Ala Ser Thr Leu Ala Ser Gly Val Ser Ser Arg Phe Lys
            180                 185                 190

Gly Ser Gly Ser Gly Thr Glu Phe Thr Leu Thr Ile Ser Asp Leu Glu
        195                 200                 205

Cys Ala Asp Ala Ala Thr Tyr Tyr Cys Gln Ser Thr Tyr Val Asn Arg
    210                 215                 220

Gly Ser Val Ala Ala Phe Gly Gly Thr Glu Val Val Val Lys Ser
225                 230                 235                 240

Gly Gly Gly Gly Ser Gly Gly Gly Gly Ser Gly Gly Gly Gly Ser Ser
                245                 250                 255

Gly Asp Ile Thr Gly Ala Ala Leu Leu Glu Ala Lys Asp Ala Ala Ile
            260                 265                 270

Asn Glu Leu Lys Gln Tyr Gly Ile Ser Asp Tyr Tyr Val His Leu Ile
        275                 280                 285

Asn Lys Ala Asp Thr Val Glu Gly Val Asn Ala Leu Lys Asp Glu Ile
    290                 295                 300

Leu Ser Ala Leu Pro
305

<210> SEQ ID NO 35
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Glu Leu Val Leu Thr Gln Gln Pro Ala Ser Val Glu Ala Ala Pro Gly
1               5                   10                  15

Gly Thr Val Thr Ile Lys Cys Gln Ala Ser Gln Ser Ile Ser Ser Tyr
                20                  25                  30

Leu Ala Trp Tyr Gln Gln Lys Pro Gly His Pro Pro Lys Leu Leu Ile
            35                  40                  45

Tyr Lys Val Ser Thr Arg Ala Ser Gly Val Ser Ser Arg Phe Ser Gly
        50                  55                  60

Ser Gly Ser Gly Thr Glu Phe Thr Leu Thr Ile Ser Asp Leu Lys Ser
65                  70                  75                  80

Ala Asp Ala Ala Thr Tyr Tyr Cys Gln Ser Ala Tyr Leu Gly Gly Thr
                85                  90                  95

Tyr Val Gly Gly Ala Phe Gly Gly Gly Thr Glu Leu Glu Ile Lys Ser
            100                 105                 110

Gly Gly Gly Gly Ser Gly Gly Gly Ser Gly Gly Gly Gly Ser Ser
            115                 120                 125

Gly Glu Leu Val Met Thr Gln Gln Pro Ala Ser Val Glu Ala Ala Pro
            130                 135                 140

Gly Gly Thr Val Thr Ile Lys Cys Gln Ala Ser Gln Ser Ile Ser Ser
145                 150                 155                 160

Tyr Leu Ala Trp Tyr Gln Gln Lys Pro Gly Gln Pro Pro Lys Leu Leu
                165                 170                 175

Ile Tyr Arg Val Ser Thr Arg Ala Ser Gly Val Ser Ser Arg Phe Ser
            180                 185                 190

Gly Ser Gly Ser Gly Thr Glu Phe Thr Leu Thr Ile Ser Asp Leu Lys
        195                 200                 205

Ser Ala Asp Ala Ala Thr Tyr Tyr Cys Gln Ser Ala Tyr Val Asn Arg
    210                 215                 220

Gly Ser Val Ala Ser Phe Gly Gly Gly Thr Lys Val Val Val Lys
225                 230                 235

<210> SEQ ID NO 36
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Glu Leu Val Leu Thr Gln Gln Pro Ala Ser Val Glu Ala Ala Pro Gly
1               5                   10                  15

Gly Thr Val Thr Ile Lys Cys Gln Ala Ser Gln Ser Ile Ser Ser Tyr
                20                  25                  30

Leu Ala Trp Tyr Gln Gln Lys Pro Gly His Pro Pro Lys Leu Leu Ile
            35                  40                  45

```
Tyr Lys Val Ser Thr Glu Ala Ser Gly Val Ser Ser Arg Phe Ser Gly
             50                  55                  60

Ser Gly Ser Gly Thr Glu Phe Thr Leu Thr Ile Ser Asp Leu Lys Ser
 65                  70                  75                  80

Ala Asp Ala Ala Thr Tyr Tyr Cys Gln Ser Ala Tyr Leu Gly Gly Thr
                 85                  90                  95

Tyr Val Gly Gly Ala Phe Gly Gly Thr Glu Leu Glu Ile Lys Ser
                100                 105                 110

Gly Gly Gly Gly Ser Gly Gly Gly Ser Gly Gly Gly Ser Ser
                115                 120                 125

Gly Glu Leu Val Met Thr Gln Gln Pro Ala Ser Val Glu Ala Ala Pro
            130                 135                 140

Gly Gly Thr Val Thr Ile Lys Cys Gln Ala Ser Gln Ser Ile Ser Ser
145                 150                 155                 160

Tyr Leu Ala Trp Tyr Gln Gln Lys Pro Gly Gln Pro Pro Lys Leu Leu
                165                 170                 175

Ile Tyr Arg Val Ser Thr Glu Ala Ser Gly Val Ser Ser Arg Phe Ser
                180                 185                 190

Gly Ser Gly Ser Gly Thr Glu Phe Thr Leu Thr Ile Ser Asp Leu Lys
                195                 200                 205

Ser Ala Asp Ala Ala Thr Tyr Tyr Cys Gln Ser Ala Tyr Val Asn Arg
210                 215                 220

Gly Ser Val Ala Ser Phe Gly Gly Gly Thr Lys Val Val Lys
225                 230                 235

<210> SEQ ID NO 37
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Glu Leu Val Leu Thr Gln Gln Pro Ala Ser Val Glu Ala Ala Pro Gly
 1               5                  10                  15

Gly Thr Val Thr Ile Lys Cys Gln Ala Ser Gln Ser Ile Ser Ser Tyr
                20                  25                  30

Leu Ala Trp Tyr Gln Gln Lys Pro Gly His Pro Pro Lys Leu Leu Ile
                35                  40                  45

Tyr Lys Val Ser Thr Arg Ala Ser Gly Val Ser Ser Arg Phe Ser Gly
             50                  55                  60

Ser Gly Ser Gly Thr Glu Phe Thr Leu Thr Ile Ser Asp Leu Lys Ser
 65                  70                  75                  80

Ala Asp Ala Ala Thr Tyr Tyr Cys Gln Ser Thr Tyr Leu Gly Gly Thr
                 85                  90                  95

Tyr Val Gly Gly Ala Phe Gly Gly Thr Glu Leu Glu Ile Lys Ser
                100                 105                 110

Gly Gly Gly Gly Ser Gly Gly Gly Ser Gly Gly Gly Ser Ser
                115                 120                 125

Gly Glu Leu Val Met Thr Gln Gln Pro Ala Ser Val Glu Ala Ala Pro
            130                 135                 140

Gly Gly Thr Val Thr Ile Lys Cys Gln Ala Ser Gln Ser Ile Ser Ser
145                 150                 155                 160

Tyr Leu Ala Trp Tyr Gln Gln Lys Pro Gly Gln Pro Pro Lys Leu Leu
```

```
                    165                 170                 175

Ile Tyr Arg Val Ser Thr Arg Ala Ser Gly Val Ser Ser Arg Phe Ser
                180                 185                 190

Gly Ser Gly Ser Gly Thr Glu Phe Thr Leu Thr Ile Ser Asp Leu Lys
            195                 200                 205

Ser Ala Asp Ala Ala Thr Tyr Tyr Cys Gln Ser Thr Tyr Val Asn Arg
        210                 215                 220

Gly Ser Val Ala Ala Phe Gly Gly Gly Thr Lys Val Val Val Lys
225                 230                 235

<210> SEQ ID NO 38
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Glu Leu Val Leu Thr Gln Gln Pro Ala Ser Val Glu Ala Ala Pro Gly
1               5                   10                  15

Gly Thr Val Thr Ile Lys Cys Gln Ala Ser Gln Ser Ile Ser Ser Tyr
            20                  25                  30

Leu Ala Trp Tyr Gln Gln Lys Pro Gly His Pro Pro Lys Leu Leu Ile
        35                  40                  45

Tyr Lys Val Ser Thr Glu Ala Ser Gly Val Ser Ser Arg Phe Ser Gly
    50                  55                  60

Ser Gly Ser Gly Thr Glu Phe Thr Leu Thr Ile Ser Asp Leu Lys Ser
65                  70                  75                  80

Ala Asp Ala Ala Thr Tyr Tyr Cys Gln Ser Thr Tyr Leu Gly Gly Thr
                85                  90                  95

Tyr Val Gly Gly Ala Phe Gly Gly Gly Thr Glu Leu Glu Ile Lys Ser
            100                 105                 110

Gly Gly Gly Gly Ser Gly Gly Gly Gly Ser Gly Gly Gly Gly Ser Ser
        115                 120                 125

Gly Glu Leu Val Met Thr Gln Gln Pro Ala Ser Val Glu Ala Ala Pro
    130                 135                 140

Gly Gly Thr Val Thr Ile Lys Cys Gln Ala Ser Gln Ser Ile Ser Ser
145                 150                 155                 160

Tyr Leu Ala Trp Tyr Gln Gln Lys Pro Gly Gln Pro Pro Lys Leu Leu
                165                 170                 175

Ile Tyr Arg Val Ser Thr Glu Ala Ser Gly Val Ser Ser Arg Phe Ser
            180                 185                 190

Gly Ser Gly Ser Gly Thr Glu Phe Thr Leu Thr Ile Ser Asp Leu Lys
        195                 200                 205

Ser Ala Asp Ala Ala Thr Tyr Tyr Cys Gln Ser Thr Tyr Val Asn Arg
    210                 215                 220

Gly Ser Val Ala Ala Phe Gly Gly Gly Thr Lys Val Val Val Lys
225                 230                 235

<210> SEQ ID NO 39
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide
```

-continued

<400> SEQUENCE: 39

Glu Leu Val Leu Thr Gln Gln Pro Ala Ser Val Glu Ala Ala Pro Gly
1               5                   10                  15

Gly Thr Val Thr Ile Lys Cys Gln Ala Ser Gln Ser Ile Ser Ser Tyr
            20                  25                  30

Leu Ala Trp Tyr Gln Gln Lys Pro Gly His Pro Pro Lys Leu Leu Ile
        35                  40                  45

Tyr Lys Ala Ser Thr Leu Ala Ser Gly Val Ser Ser Arg Phe Ser Gly
    50                  55                  60

Ser Gly Ser Gly Thr Glu Phe Thr Leu Thr Ile Ser Asp Leu Lys Ser
65                  70                  75                  80

Ala Asp Ala Ala Thr Tyr Tyr Cys Gln Ser Thr Tyr Leu Gly Gly Thr
                85                  90                  95

Tyr Val Gly Gly Ala Phe Gly Gly Gly Thr Glu Leu Glu Ile Lys Ser
            100                 105                 110

Gly Gly Gly Gly Ser Gly Gly Gly Ser Gly Gly Gly Gly Ser Ser
            115                 120                 125

Gly Glu Leu Val Met Thr Gln Gln Pro Ala Ser Val Glu Ala Ala Pro
    130                 135                 140

Gly Gly Thr Val Thr Ile Lys Cys Gln Ala Ser Gln Ser Ile Ser Ser
145                 150                 155                 160

Tyr Leu Ala Trp Tyr Gln Gln Lys Pro Gly Gln Pro Pro Lys Leu Leu
                165                 170                 175

Ile Tyr Arg Ala Ser Thr Leu Ala Ser Gly Val Ser Ser Arg Phe Ser
            180                 185                 190

Gly Ser Gly Ser Gly Thr Glu Phe Thr Leu Thr Ile Ser Asp Leu Lys
        195                 200                 205

Ser Ala Asp Ala Ala Thr Tyr Tyr Cys Gln Ser Thr Tyr Val Asn Arg
    210                 215                 220

Gly Ser Val Ala Ala Phe Gly Gly Gly Thr Lys Val Val Val Lys
225                 230                 235

<210> SEQ ID NO 40
<211> LENGTH: 309
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Glu Leu Val Leu Thr Gln Gln Pro Ala Ser Val Glu Ala Ala Pro Gly
1               5                   10                  15

Gly Thr Val Thr Ile Lys Cys Gln Ala Ser Gln Ser Ile Ser Ser Tyr
            20                  25                  30

Leu Ala Trp Tyr Gln Gln Lys Pro Gly His Pro Pro Lys Leu Leu Ile
        35                  40                  45

Tyr Lys Val Ser Thr Arg Ala Ser Gly Val Ser Ser Arg Phe Ser Gly
    50                  55                  60

Ser Gly Ser Gly Thr Glu Phe Thr Leu Thr Ile Ser Asp Leu Lys Ser
65                  70                  75                  80

Ala Asp Ala Ala Thr Tyr Tyr Cys Gln Ser Ala Tyr Leu Gly Gly Thr
                85                  90                  95

Tyr Val Gly Gly Ala Phe Gly Gly Gly Thr Glu Leu Glu Ile Lys Ser
            100                 105                 110

Gly Gly Gly Gly Ser Gly Gly Gly Ser Gly Gly Gly Ser Ser
            115                 120                 125

Gly Glu Leu Val Met Thr Gln Gln Pro Ala Ser Val Glu Ala Ala Pro
    130                 135                 140

Gly Gly Thr Val Thr Ile Lys Cys Gln Ala Ser Gln Ser Ile Ser Ser
145                 150                 155                 160

Tyr Leu Ala Trp Tyr Gln Gln Lys Pro Gly Gln Pro Pro Lys Leu Leu
                165                 170                 175

Ile Tyr Arg Val Ser Thr Arg Ala Ser Gly Val Ser Ser Arg Phe Ser
            180                 185                 190

Gly Ser Gly Ser Gly Thr Glu Phe Thr Leu Thr Ile Ser Asp Leu Lys
    195                 200                 205

Ser Ala Asp Ala Ala Thr Tyr Tyr Cys Gln Ser Ala Tyr Val Asn Arg
210                 215                 220

Gly Ser Val Ala Ser Phe Gly Gly Gly Thr Lys Val Val Lys Ser
225                 230                 235                 240

Gly Gly Gly Gly Ser Gly Gly Gly Ser Gly Gly Gly Gly Ser Ser
                245                 250                 255

Gly Asp Ile Thr Gly Ala Ala Leu Leu Glu Ala Lys Asp Ala Ala Ile
    260                 265                 270

Asn Glu Leu Lys Gln Tyr Gly Ile Ser Asp Tyr Tyr Val His Leu Ile
    275                 280                 285

Asn Lys Ala Asp Thr Val Glu Gly Val Asn Ala Leu Lys Asp Glu Ile
    290                 295                 300

Leu Ser Ala Leu Pro
305

<210> SEQ ID NO 41
<211> LENGTH: 309
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Glu Leu Val Leu Thr Gln Gln Pro Ala Ser Val Glu Ala Ala Pro Gly
1               5                   10                  15

Gly Thr Val Thr Ile Lys Cys Gln Ala Ser Gln Ser Ile Ser Ser Tyr
            20                  25                  30

Leu Ala Trp Tyr Gln Gln Lys Pro Gly His Pro Pro Lys Leu Leu Ile
        35                  40                  45

Tyr Lys Val Ser Thr Glu Ala Ser Gly Val Ser Ser Arg Phe Ser Gly
    50                  55                  60

Ser Gly Ser Gly Thr Glu Phe Thr Leu Thr Ile Ser Asp Leu Lys Ser
65                  70                  75                  80

Ala Asp Ala Ala Thr Tyr Tyr Cys Gln Ser Ala Tyr Leu Gly Gly Thr
                85                  90                  95

Tyr Val Gly Gly Ala Phe Gly Gly Gly Thr Glu Leu Glu Ile Lys Ser
            100                 105                 110

Gly Gly Gly Gly Ser Gly Gly Gly Ser Gly Gly Gly Gly Ser Ser
        115                 120                 125

Gly Glu Leu Val Met Thr Gln Gln Pro Ala Ser Val Glu Ala Ala Pro
    130                 135                 140

Gly Gly Thr Val Thr Ile Lys Cys Gln Ala Ser Gln Ser Ile Ser Ser
145                 150                 155                 160

```
Tyr Leu Ala Trp Tyr Gln Gln Lys Pro Gly Gln Pro Pro Lys Leu Leu
                165                 170                 175

Ile Tyr Arg Val Ser Thr Glu Ala Ser Gly Val Ser Ser Arg Phe Ser
            180                 185                 190

Gly Ser Gly Ser Gly Thr Glu Phe Thr Leu Thr Ile Ser Asp Leu Lys
        195                 200                 205

Ser Ala Asp Ala Ala Thr Tyr Tyr Cys Gln Ser Ala Tyr Val Asn Arg
    210                 215                 220

Gly Ser Val Ala Ser Phe Gly Gly Thr Lys Val Val Lys Ser
225                 230                 235                 240

Gly Gly Gly Gly Ser Gly Gly Gly Ser Gly Gly Gly Gly Ser Ser
                245                 250                 255

Gly Asp Ile Thr Gly Ala Ala Leu Leu Glu Ala Lys Asp Ala Ala Ile
            260                 265                 270

Asn Glu Leu Lys Gln Tyr Gly Ile Ser Asp Tyr Tyr Val His Leu Ile
        275                 280                 285

Asn Lys Ala Asp Thr Val Glu Gly Val Asn Ala Leu Lys Asp Glu Ile
    290                 295                 300

Leu Ser Ala Leu Pro
305

<210> SEQ ID NO 42
<211> LENGTH: 309
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Glu Leu Val Leu Thr Gln Gln Pro Ala Ser Val Glu Ala Ala Pro Gly
1               5                   10                  15

Gly Thr Val Thr Ile Lys Cys Gln Ala Ser Gln Ser Ile Ser Ser Tyr
            20                  25                  30

Leu Ala Trp Tyr Gln Gln Lys Pro Gly His Pro Pro Lys Leu Leu Ile
        35                  40                  45

Tyr Lys Val Ser Thr Arg Ala Ser Gly Val Ser Ser Arg Phe Ser Gly
    50                  55                  60

Ser Gly Ser Gly Thr Glu Phe Thr Leu Thr Ile Ser Asp Leu Lys Ser
65                  70                  75                  80

Ala Asp Ala Ala Thr Tyr Tyr Cys Gln Ser Thr Tyr Leu Gly Gly Thr
                85                  90                  95

Tyr Val Gly Gly Ala Phe Gly Gly Thr Glu Leu Glu Ile Lys Ser
            100                 105                 110

Gly Gly Gly Gly Ser Gly Gly Gly Gly Ser Gly Gly Gly Ser Ser
        115                 120                 125

Gly Glu Leu Val Met Thr Gln Gln Pro Ala Ser Val Glu Ala Ala Pro
    130                 135                 140

Gly Gly Thr Val Thr Ile Lys Cys Gln Ala Ser Gln Ser Ile Ser Ser
145                 150                 155                 160

Tyr Leu Ala Trp Tyr Gln Gln Lys Pro Gly Gln Pro Pro Lys Leu Leu
                165                 170                 175

Ile Tyr Arg Val Ser Thr Arg Ala Ser Gly Val Ser Ser Arg Phe Ser
            180                 185                 190

Gly Ser Gly Ser Gly Thr Glu Phe Thr Leu Thr Ile Ser Asp Leu Lys
```

```
                195                 200                 205
Ser Ala Asp Ala Ala Thr Tyr Tyr Cys Gln Ser Thr Tyr Val Asn Arg
    210                 215                 220

Gly Ser Val Ala Ala Phe Gly Gly Thr Lys Val Val Lys Ser
225                 230                 235                 240

Gly Gly Gly Gly Ser Gly Gly Gly Ser Gly Gly Gly Ser Ser
                245                 250                 255

Gly Asp Ile Thr Gly Ala Ala Leu Leu Glu Ala Lys Asp Ala Ala Ile
            260                 265                 270

Asn Glu Leu Lys Gln Tyr Gly Ile Ser Asp Tyr Tyr Val His Leu Ile
        275                 280                 285

Asn Lys Ala Asp Thr Val Glu Gly Val Asn Ala Leu Lys Asp Glu Ile
    290                 295                 300

Leu Ser Ala Leu Pro
305

<210> SEQ ID NO 43
<211> LENGTH: 309
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Glu Leu Val Leu Thr Gln Gln Pro Ala Ser Val Glu Ala Ala Pro Gly
1               5                   10                  15

Gly Thr Val Thr Ile Lys Cys Gln Ala Ser Gln Ser Ile Ser Ser Tyr
            20                  25                  30

Leu Ala Trp Tyr Gln Gln Lys Pro Gly His Pro Pro Lys Leu Leu Ile
        35                  40                  45

Tyr Lys Val Ser Thr Glu Ala Ser Gly Val Ser Ser Arg Phe Ser Gly
    50                  55                  60

Ser Gly Ser Gly Thr Glu Phe Thr Leu Thr Ile Ser Asp Leu Lys Ser
65                  70                  75                  80

Ala Asp Ala Ala Thr Tyr Tyr Cys Gln Ser Thr Tyr Leu Gly Gly Thr
                85                  90                  95

Tyr Val Gly Gly Ala Phe Gly Gly Gly Thr Glu Leu Glu Ile Lys Ser
            100                 105                 110

Gly Gly Gly Gly Ser Gly Gly Gly Ser Gly Gly Gly Ser Ser
        115                 120                 125

Gly Glu Leu Val Met Thr Gln Gln Pro Ala Ser Val Glu Ala Ala Pro
    130                 135                 140

Gly Gly Thr Val Thr Ile Lys Cys Gln Ala Ser Gln Ser Ile Ser Ser
145                 150                 155                 160

Tyr Leu Ala Trp Tyr Gln Gln Lys Pro Gly Gln Pro Pro Lys Leu Leu
                165                 170                 175

Ile Tyr Arg Val Ser Thr Glu Ala Ser Gly Val Ser Ser Arg Phe Ser
            180                 185                 190

Gly Ser Gly Ser Gly Thr Glu Phe Thr Leu Thr Ile Ser Asp Leu Lys
        195                 200                 205

Ser Ala Asp Ala Ala Thr Tyr Tyr Cys Gln Ser Thr Tyr Val Asn Arg
    210                 215                 220

Gly Ser Val Ala Ala Phe Gly Gly Gly Thr Lys Val Val Lys Ser
225                 230                 235                 240
```

Gly Gly Gly Gly Ser Gly Gly Gly Ser Gly Gly Gly Ser Ser
            245                 250                 255

Gly Asp Ile Thr Gly Ala Ala Leu Leu Glu Ala Lys Asp Ala Ala Ile
            260                 265                 270

Asn Glu Leu Lys Gln Tyr Gly Ile Ser Asp Tyr Tyr Val His Leu Ile
            275                 280                 285

Asn Lys Ala Asp Thr Val Glu Gly Val Asn Ala Leu Lys Asp Glu Ile
            290                 295                 300

Leu Ser Ala Leu Pro
305

<210> SEQ ID NO 44
<211> LENGTH: 309
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Glu Leu Val Leu Thr Gln Gln Pro Ala Ser Val Glu Ala Ala Pro Gly
1               5                   10                  15

Gly Thr Val Thr Ile Lys Cys Gln Ala Ser Gln Ser Ile Ser Ser Tyr
            20                  25                  30

Leu Ala Trp Tyr Gln Gln Lys Pro Gly His Pro Pro Lys Leu Leu Ile
        35                  40                  45

Tyr Lys Ala Ser Thr Leu Ala Ser Gly Val Ser Ser Arg Phe Ser Gly
    50                  55                  60

Ser Gly Ser Gly Thr Glu Phe Thr Leu Thr Ile Ser Asp Leu Lys Ser
65                  70                  75                  80

Ala Asp Ala Ala Thr Tyr Tyr Cys Gln Ser Thr Tyr Leu Gly Gly Thr
                85                  90                  95

Tyr Val Gly Gly Ala Phe Gly Gly Gly Thr Glu Leu Glu Ile Lys Ser
            100                 105                 110

Gly Gly Gly Gly Ser Gly Gly Gly Ser Gly Gly Gly Gly Ser Ser
            115                 120                 125

Gly Glu Leu Val Met Thr Gln Gln Pro Ala Ser Val Glu Ala Ala Pro
            130                 135                 140

Gly Gly Thr Val Thr Ile Lys Cys Gln Ala Ser Gln Ser Ile Ser Ser
145                 150                 155                 160

Tyr Leu Ala Trp Tyr Gln Gln Lys Pro Gly Gln Pro Pro Lys Leu Leu
                165                 170                 175

Ile Tyr Arg Ala Ser Thr Leu Ala Ser Gly Val Ser Ser Arg Phe Ser
            180                 185                 190

Gly Ser Gly Ser Gly Thr Glu Phe Thr Leu Thr Ile Ser Asp Leu Lys
            195                 200                 205

Ser Ala Asp Ala Ala Thr Tyr Tyr Cys Gln Ser Thr Tyr Val Asn Arg
        210                 215                 220

Gly Ser Val Ala Ala Phe Gly Gly Gly Thr Lys Val Val Lys Ser
225                 230                 235                 240

Gly Gly Gly Gly Ser Gly Gly Gly Gly Ser Gly Gly Gly Gly Ser Ser
                245                 250                 255

Gly Asp Ile Thr Gly Ala Ala Leu Leu Glu Ala Lys Asp Ala Ala Ile
            260                 265                 270

Asn Glu Leu Lys Gln Tyr Gly Ile Ser Asp Tyr Tyr Val His Leu Ile
            275                 280                 285

```
Asn Lys Ala Asp Thr Val Glu Gly Val Asn Ala Leu Lys Asp Glu Ile
    290                 295                 300

Leu Ser Ala Leu Pro
305

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Gly Gly Gly Ser
1               5

<210> SEQ ID NO 46
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Gly Ser Gly
1

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Gly Ser Gly Gly Ser
1               5

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Gly Gly Gly Ser Gly Gly Gly Ser
1               5

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Gly Gly Gly Ser Gly Gly Gly Gly Ser
1               5                   10

<210> SEQ ID NO 50
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gly Gly Gly Gly Ser Gly Gly Gly Gly Ser Gly Gly Gly Gly Ser
1               5                   10                  15

<210> SEQ ID NO 51
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Gly Gly Gly Ser Gly Gly Gly Gly Ser Gly Gly Gly Gly Ser Gly
1               5                   10                  15

Gly Gly Gly Ser
            20

<210> SEQ ID NO 52
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 53
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ser Gly Gly Gly Gly Ser Ser Gly
1               5

<210> SEQ ID NO 55
```

```
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ser Gly Gly Gly Gly Ser Gly Gly Gly Ser Gly Gly Gly Gly Ser
1               5                   10                  15

Ser Gly

<210> SEQ ID NO 56
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ser Gly Gly Gly Gly Ser Gly Gly Gly Ser Gly Gly Gly Gly Ser
1               5                   10                  15

Gly Gly Gly Gly Ser Ser Gly
            20

<210> SEQ ID NO 57
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ser Gly Gly Gly Gly Ser Gly Gly Gly Ser Gly Gly Gly Gly Ser
1               5                   10                  15

Gly Gly Gly Gly Ser Gly Gly Gly Gly Ser Ser Gly
            20                  25

<210> SEQ ID NO 58
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Ser Gly Gly Gly Gly Ser Gly Gly Gly Ser Gly Gly Gly Gly Ser
1               5                   10                  15

Gly Gly Gly Gly Ser Gly Gly Gly Gly Ser Gly Gly Gly Gly Ser Gly
            20                  25                  30

Gly Gly Gly Ser Ser Gly
        35

<210> SEQ ID NO 59
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59
```

-continued

```
Pro Thr Pro Thr Pro Thr Thr Pro Thr Pro Thr Pro Thr Thr Pro Thr
1               5                   10                  15

Pro Thr Pro Thr Ser
            20

<210> SEQ ID NO 60
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 60

His His His His His His
1               5

<210> SEQ ID NO 61
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Tyr Pro Tyr Asp Val Pro Asp Tyr Ala
1               5

<210> SEQ ID NO 62
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(35)
<223> OTHER INFORMATION: This region may encompass 1, 2, 3, 4, 5, 6,
      or 7 '[Ser-(Gly)4]' repeating units
<220> FEATURE:
<221> NAME/KEY: MISC_FEATURE
<222> LOCATION: (6)..(35)
<223> OTHER INFORMATION: May or may not be present
<220> FEATURE:
<223> OTHER INFORMATION: See specification as filed for detailed
      description of substitutions and preferred embodiments

<400> SEQUENCE: 62

Ser Gly Gly Gly Gly Ser Gly Gly Gly Ser Gly Gly Gly Gly Ser
1               5                   10                  15

Gly Gly Gly Gly Ser Gly Gly Gly Gly Ser Gly Gly Gly Gly Ser Gly
            20                  25                  30

Gly Gly Gly Ser Ser Gly
            35
```

ANTI-TUMOR NECROSIS FACTOR-ALPHA AGENTS AND USES THEREOF

CROSS-REFERENCE TO RELATED APPLICATIONS

This is application claims the benefit of U.S. Provisional Application Ser. No. 61/538,548, filed Sep. 23, 2011, the contents of which are hereby incorporated-by-reference in its entirety. This application also relates to U.S. Provisional Application Ser. No. 61/538,552, entitled "Modified Albumin-binding Domains and Uses Thereof to Improve Pharmacokinetics", filed by Frederico Aires da Silva, Sofia Volker Côrte-Real, Rui Freitas and Sara Lourenço also on Sep. 23, 2011, the contents of which also are hereby incorporated-by-reference in its entirety.

The instant application contains a Sequence Listing which has been submitted electronically in ASCII format and is hereby incorporated by reference in its entirety. Said ASCII copy, created on Jan. 25, 2016, is named 14116-105011US_SL.txt and is 69,466 bytes in size.

FIELD OF THE INVENTION

The present invention relates to anti-Tumor Necrosis Factor polypeptides comprising one or more antibody single variable domains, or antigen-binding fragments thereof, in particular, dimers comprising two light chain variable domains that have high solubility. It also relates to methods of using anti-Tumor Necrosis Factor-alpha polypeptides of the invention in treating, preventing, or managing Tumor Necrosis Factor-alpha-related conditions, such as inflammatory disorders, e.g., rheumatoid arthritis. Compositions and methods for enhancing therapeutic potential of anti-Tumor Necrosis Factor-alpha polypeptides also are provided, including linking the polypeptide to an albumin-binding domain and/or de-immunizing the polypeptide, so as to provide therapeutic agents with good solubility, enhanced serum half-life, and/or reduced immunogenicity, while substantially maintaining the specific binding properties of the anti-Tumor Necrosis Factor-alpha polypeptides.

BACKGROUND

Tumor necrosis factor alpha (TNF-alpha) is a cytokine that exists as a trimeric molecule and has two bioactive forms—membrane-bound TNF-alpha and soluble TNF-alpha. The membrane bound form of TNF-alpha is composed of extracellular, transmembrane and cytoplasmic domains. Cleavage of the membrane bound form (about 26 kDa) results in the soluble form (~17 kDa), which exists as a homodimer. While both forms are biologically active, the soluble form of TNF-alpha is more potent.

TNF-alpha exerts effects on cell proliferation, cell differentiation, inflammation, and cell death, as well as on immunoregulation, by binding to specific cell surface receptors. The groove created by neighboring subunits of the trimeric molecule is important for interaction with its receptors. The two known TNF-alpha receptors include the p55 (CD120a) and p75 (CD120b) receptors. The p55 receptor is expressed on most cells; whereas the p75 receptor shows much more restricted expression, mainly on activated white blood cells. It is believed that TNF-alpha plays an important role in various conditions and disorders, including, for example, inflammatory disorders, such as rheumatoid arthritis, psoriatic arthritis, and Crohn's disease.

Chronic inflammatory diseases can be life-changing, debilitating conditions, and rheumatoid arthritis (RA) is one of the most common. RA is characterised by symmetric inflammation of the peripheral joints, resulting in progressive destruction of the joint. Approximately 1-2% of the world's population is affected by RA, and one in three patients is likely to become severely disabled within 20 years of diagnosis. The onset of RA most often occurs between the ages of 40 and 50, with three times more women affected than men. There is no cure for RA; treatment is aimed at slowing the disease and minimizing joint damage, while maintaining quality of life.

Several strategies have been developed to antagonize the action of TNF-alpha with its receptors in various conditions where the cytokine has been implicated as a causative agent. For example, blocking the action of excessive TNF-alpha is a therapeutic strategy in several inflammatory diseases, like rheumatoid arthritis. With RA, in particular, there has been a recent shift in treatment paradigm, with new emphasis on starting treatment against TNF-alpha earlier in the course of the disease. One type of therapeutic directed against TNF-alpha involves anti-TNF-alpha antibodies.

Conventional antibodies, however, may be difficult to raise against multimeric proteins, where the receptor-binding domain is embedded in a groove, as is the case with the active forms of TNF-alpha. Furthermore, mammalian cellular systems are normally needed to express intact, functional antibodies, which contributes to high costs of manufacture. Obtaining a therapeutically useful antibody can require additional modification, such as avoiding unwanted immunological reactions upon administration to a human subject. Traditional antibodies also may not be stable at room temperature, requiring refrigeration during manufacture, storage, and transport, further adding to expense. Moreover, the large size of conventional antibodies can restrict solubility and tissue penetration.

One approach to addressing some of these issues involves the use of single domain antibodies. However, the relatively small size of such molecules can result in the products having short half lives in vivo. Several strategies have been used to overcome the problems associated with short serum half-life. For example, certain protein fusions have been attempted to increase the size and, thus, stability and half-life of protein therapeutics. (Syed et al. (1997) *Blood* 89:3243-3252; Yeh, et al. (1992) *Proc. Natl. Acad. Sci. U.S.A.* 89:1904-1908). Fusion products are prone to misfolding, however, and the fused region can create additional immunogenic sites. Nonetheless, fusions of therapeutic proteins to albumin have been attempted.

Albumin (molecular mass of 67 kDa) is the most abundant protein in plasma, present at 50 mg/ml, and having a half-life of 19 days in humans (Peters, T., Jr. (1985) *Adv. Protein Chem.* 37:161-245; Peters, T., Jr. (1996) *All about Albumin*, Academic Press, Inc., San Diego, Calif.). Albumin plays a vital role in vivo by reversibly binding and transporting a wide variety of endogenous substances as well as drugs, and several major small molecule binding sites in albumin have been described. (e.g., see, Frick, et al. (1994) *Mol Microbiol.* 12:143-51; and Akesson et al. (1994) *Biochem. J.* 300:877-886). Still a further strategy involves coupling the therapeutic to another protein that allows in vivo association to serum albumins. Examples of this approach also have been described, e.g. in EP 0486525 and U.S. Pat. No. 6,267,964, which describe the use of albumin-binding peptides or proteins derived from streptococcal protein G (SpG) for increasing the half-life of other proteins.

There are at least five anti-TNF-alpha products on the market, Infliximab (Remicade™), Adalimumab (Humira), Etanercept (Enbrel), Certolizumab pegol (Cimzia), and Golimumab (Simponi), each of which is associated with a high cost of treatment. For example, each of the anti-TNF products on the market use non-human primates as the main relevant species for assessing toxicity, contributing to high costs. More importantly, existing treatments can be marginally effective and/or poorly tolerated, while too expensive for feasible use in combinations. Approximately one-third of patients fail to respond to these therapies and adverse reactions are common. Patients who have a poor response with one TNF-alpha inhibitor are typically switched to another and, further, many patients develop an immunogenic response towards a given product and thus similarly need to change their treatment.

Accordingly, there is a need for therapeutics directed against TNF-alpha that provide specificity, solubility, and longer half-life, as well as reduced immunogenicity in the subject, in a cost-effective manner. In particular, there is a need for therapeutics to treat TNF-alpha mediated conditions, like inflammatory disorders, that can be given less frequently, at lower doses, in combination with existing drugs, and/or in a manner that facilitates self-administration. Antibody single domain-based therapeutics provided herein address these and other needs.

The foregoing discussion is presented solely to provide a better understanding of the nature of the problems confronting the art and should not be construed in any way as an admission as to prior art nor should the citation of any reference herein be construed as an admission that such reference constitutes "prior art" to the instant application.

SUMMARY OF THE INVENTION

One aspect of the invention relates to polypeptides comprising an antibody single domain, or antigen-binding fragment thereof, that binds TNF-alpha, termed an anti-TNF-alpha polypeptide. In some embodiments, the domain comprises a light chain variable domain (VL), where the variable domain comprises at least one amino acid sequence selected from the group consisting of SEQ ID NO:1 (VL18); SEQ ID NO:2 (VL11); SEQ ID NOs:3-18, and a TNF-alpha-binding fragment or derivative thereof. In some preferred embodiments, the variable domain of the polypeptide antagonizes binding of human TNF-alpha to a TNF-alpha receptor, and/or further cross-reacts with at least one other mammalian TNF-alpha. In some preferred embodiments, the mammal is not a primate, e.g., the mammal may be a rat or a mouse. In some more preferred embodiments, the variable domain cross-reacts with TNF-alpha of at least two other mammals, including a rodent and a non-rodent species.

In some embodiments, the anti-TNF-alpha polypeptide in accordance with the invention further comprises a second antibody single domain, or antigen-binding fragment thereof, that also binds TNF-alpha, such that the single domains together form a dimer. The second domain also may comprise a light chain variable domain. For example, in some particular embodiments, the dimer comprises sequences corresponding to SEQ ID NO:1 (VL18) and SEQ ID NO:2 (VL11), or a TNF-alpha-binding fragment or derivative thereof for one or both sequences. In some particular embodiments, the dimer comprises a sequence corresponding to SEQ ID NO:32 (VL18-3L-VL11), or a TNF-alpha-binding fragment or derivative thereof.

Another aspect of the invention relates to an anti-TNF-alpha polypeptide further comprising an albumin-binding domain linked thereto. The albumin-binding domain may be linked to the polypeptide as a fusion, e.g., as a fusion via a linker. In some particular embodiments, the linker is a peptide linker comprising an amino acid sequence corresponding to SEQ ID NO:29 (3L). In some preferred embodiments, the albumin-binding domain enhances the half-life of the polypeptide, e.g., by five fold. In some more specific embodiments, the albumin-binding domain comprises a sequence corresponding to SEQ ID NO:30 (PEP), or an albumin-binding fragment or derivative thereof. For example, in some particular embodiments, the polypeptide comprises a sequence corresponding to SEQ ID NO: 33 (VL18-3L-VL11-PEP) or a TNF-alpha-binding fragment or derivative thereof.

In still another aspect of the invention, the anti-TNF-alpha polypeptides, and/or fusions or conjugates thereof with albumin-binding domains, are de-immunized. De-immunization reduces immunogenicity in the host and may be achieved by eliminating at least one $T_H$ epitope in the variable domain and/or in the albumin-binding domain. In some particular embodiments, the variable domain comprises a sequence corresponding to SEQ ID NO:1 (VL18), which is de-immunized by at least one amino acid substitution selected from the group consisting of T7Q, V15P, (A51V-L54R/A51V-L54E), K63S, E79K, (C80S), T91A, and L111K, the substitutions referring to amino acid positions in SEQ ID NO:1. In some particular embodiments, the variable domain comprises a sequence corresponding to SEQ ID NO:2 (VL11), which is de-immunized by at least one amino acid substitution selected from the group consisting of T7Q, V15P, R31S, (A51V-L54R/A51V-L54E), K63S, E79K, (C80S), T91A, A100S, and E106K, the substitutions referring to amino acid positions in SEQ ID NO:2. In some particular embodiments, the variable domain comprises at least one sequence selected from the group consisting of SEQ ID NOs:19-23 (five de-immunized VL18 variants), SEQ ID NOs: 24-28 (five de-immunized VL11 variants), and a TNF-alpha-binding fragment or derivative thereof. In some more specific embodiments, the polypeptide may comprise at least one sequence selected from the group consisting of SEQ ID NOs: 35-39 (VL18-3L-VL11 variants), or a TNF-alpha-binding fragment or derivative thereof. In some more specific embodiments, the polypeptide comprises at least one sequence selected from the group consisting of SEQ ID NOs: 34 and 40-44 (VL18-3L-VL1'-PEP variants), or a TNF-alpha-binding fragment or derivative thereof.

In some particular embodiments, the albumin-binding domain is de-immunized, e.g., by at least one amino acid substitution selected from the group consisting of E12D, T29H-K35D, and A45D, the substitutions referring to amino acid positions in SEQ ID NO:30. In some particular embodiments, the albumin-binding domain comprises an amino acid sequence corresponding to SEQ ID NO:31.

Yet another aspect of the invention relates to the use of an effective amount of one or more of the polypeptides according to the invention for the preparation of a medicament for treating and/or delaying a TNF-alpha-related condition in a subject suffering therefrom and/or pre-disposed thereto. In some embodiments, the TNF-alpha-related condition is an inflammatory disorder, such as rheumatoid arthritis. In some preferred embodiments, the medicament is administered no more than twice a month or, more preferably, no more than once a month.

Still yet another aspect of the invention relates to a pharmaceutical composition comprising an effective amount of an anti-TNF-alpha polypeptide in accordance with the invention, and/or or a nucleic acid comprising a nucleotide sequence encoding same, and a pharmaceutically acceptable carrier.

Another aspect relates to a nucleic acid comprising a nucleotide sequence encoding an anti-TNF-alpha polypeptide in accordance with the invention, as well as vectors and/or host cells and/or pharmaceutical compositions comprising same.

Still yet another aspect of the invention relates to a method of making an anti-TNF-alpha polypeptide of the invention comprising: (i) providing a host cell comprising a vector encoding the polypeptide; (ii) culturing the cell under conditions allowing expression of the polypeptide; and (iii) recovering the polypeptide from the culture.

BRIEF DESCRIPTION OF THE FIGURES

FIG. 1 illustrates a sequence comparison of VL single domains showing high affinity binding to human TNF-alpha. FIG. 1 discloses SEQ ID NOS 12, 11, 15, 8, 7, 3, 10, 13, 9, 18, 2, 6, 14, 17, 1, 16, 4, and 5, respectively, in order of appearance.

FIGS. 2A-D illustrate results of (A-C) Western Blot expression analysis for VL monomers and dimers; and (D) binding affinities of VL monomers and dimers for human and rat TNF-alpha.

FIGS. 3A-F illustrate results of binding assays and pharmacokinetics of a VL-VL dimer of the invention. FIGS. 3A-C illustrate results of affinity determinations of the dimer to human TNF-alpha and albumin-binding fusion thereof by BIAcore as compared with Remicade™; FIGS. 3D-E illustrate relative binding and specificity of the dimer to TNF molecules of various species by ELISA; FIG. 3F illustrates pharmacokinetics of VL-VL constructs (VL18-3L-VL11 and VL18-3L-VL11-PEP) tested by administration to Wistar female rats to determine the serum half-life thereof in vivo, data were normalized considering maximal concentration as that assayed 5 minutes after administration (% of 5 min value).

FIGS. 9A-F illustrates therapeutic effect of a VL-VL dimer of the invention in an established rat adjuvant-induced arthritis model (AIA) based on histological analyses.

FIGS. 12A-C illustrate proposed positions for substitutions (highlighted in gray) in two VL single domain antibodies of the invention (SEQ ID NOS 1 and 2, respectively, in order of appearance) (A-B), and in an albumin binding domain (SEQ ID NO: 30), (C), using Kabat and Ordinal numbering; CDRs are indicated by x;

FIG. 15A illustrates a schematic representation of downstream process development. FIGS. 15B-C illustrate results of Coomassie Blue SDS-PAGE expression analysis following Protein L Affinity purification of the a de-immunized dimer of the invention (VL18-3L-VL11 DI3-PEP DI #8). FIG. 15D illustrates results of Coomassie Blue SDS-PAGE expression analysis following SP Sepharose cation exchange chromatography of a de-immunized dimer of the invention (VL18-3L-VL11 DI3-PEP DI #8). FIG. 15D illustrates results of Coomassie Blue SDS-PAGE expression analysis following size exclusion chromatography of a de-immunized dimer of the invention (VL18-3L-VL11 DI3-PEP DI #8).

FIGS. 17A-I illustrates therapeutic effect of de-immunized VL-VL dimers of the invention in an established rat adjuvant-induced arthritis model (AIA) based on histological analyses.

DETAILED DESCRIPTION

1. Definitions

Figure 2D:
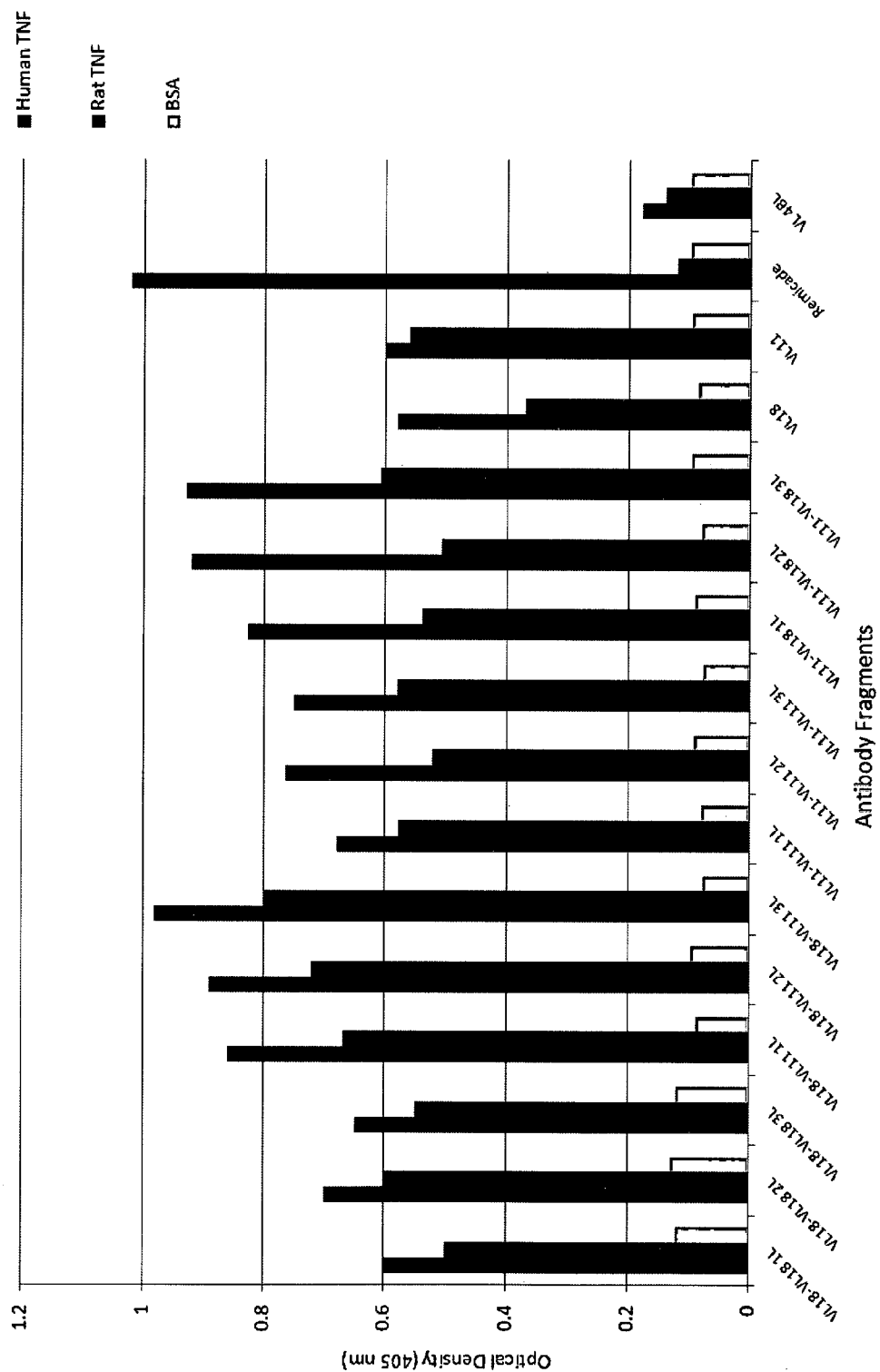

The term "derivative" when used in the context of a protein agent (including full length proteins, multimeric proteins, polypeptides, peptides, and specifically including antibodies and fragments thereof) refers to an agent that possesses a similar or identical function as a second agent but does not necessarily comprise a similar or identical amino acid sequence, modifications such as glycosylation, or secondary, tertiary or quaternary structure of the second agent. A protein agent that has a similar amino acid sequence refers to a second protein agent that satisfies at least one of the following: (a) a protein agent having an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of a second protein agent; (b) a protein agent encoded by a nucleotide sequence that hybridizes under stringent conditions to a nucleotide sequence encoding a second protein agent of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, or at least 150 contiguous amino acid residues; and (c) a protein agent encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% identical to the nucleotide sequence encoding a second protein agent. A protein agent with similar structure to a second protein agent refers to a protein agent that has a similar secondary, tertiary or quaternary structure to the second protein agent. The structure of a polypeptide can be determined by methods known to those skilled in the art, including but not limited to, peptide sequencing, X-ray crystallography, nuclear magnetic resonance, circular dichroism, and crystallographic electron microscopy.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions×100%). In one embodiment, the two sequences are the same length.

The determination of percent identity between two sequences can also be accomplished using a mathematical algorithm. One non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403.

As used herein, the term "derivative" in the context of proteins, including antibodies and fragments thereof, also refers to a polypeptide or peptide that comprises an amino acid sequence which has been altered by the introduction of amino acid residue substitutions, deletions or additions. The term "derivative" as used herein also refers to a polypeptide or peptide which has been modified, i.e., by the covalent attachment of any type of molecule to the polypeptide or peptide. For example, but not by way of limitation, a polypeptide may be modified, e.g., by glycosylation, acetylation, pegylation, phosphorylation, amidation, derivatization by known protecting/blocking groups, proteolytic cleavage, linkage to a cellular ligand or other protein, etc. A derivative polypeptide or peptide may be produced by chemical modifications using techniques known to those of skill in the art, including, but not limited to specific chemical cleavage, acetylation, formylation, metabolic synthesis of tunicamycin, etc. Further, a derivative polypeptide or peptide derivative possesses a similar, identical, or improved function as the polypeptide or peptide from which it was derived.

As used herein, "derivative" in used interchangeably with "variant."

As used herein, the term "fragment" refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, or at least contiguous 250 amino acid residues of the amino acid sequence of another polypeptide. In a specific embodiment, a fragment of a polypeptide retains at least one function of the polypeptide.

As used herein, the terms "heavy chain," "light chain," "variable region," "framework region," "constant domain," and the like, have their ordinary meaning in the immunology art and refer to domains in naturally occurring immunoglobulins and the corresponding domains of synthetic (e.g., recombinant) binding proteins (e.g., humanized antibodies, single chain antibodies, chimeric antibodies, etc.).

As used herein, the terms "immunospecifically binds," "immunospecifically recognizes," "specifically binds," "specifically recognizes" and analogous terms refer to molecules that specifically bind to an antigen (e.g., epitope or immune complex) and do not specifically bind to another molecule under physiological conditions. Molecules that specifically bind an antigen can be identified, for example, by immunoassays, BIAcore, or other techniques known to those of skill in the art. A molecule that specifically binds to an antigen may bind to other peptides or polypeptides but with lower affinity as determined by, e.g., immunoassays, BIAcore, or other assays known in the art. In some embodiments, molecules that specifically bind an antigen cross-react with other molecules (such as analogous protein from other species). As used herein, the term "antigen-binding fragment thereof" refers to an TNF-alpha-binding fragment, unless indicated otherwise.

The term "in vivo half-life", "serum half-life", or "plasma half life" (also referred to as $t_{1/2}$) as used herein refers to a biological half-life of a molecule in the circulation of a given host and is represented by a time required for half the quantity administered in the animal to be cleared from the circulation and/or other tissues in the animal. The in vivo half-life is an important clinical parameter which determines the amount and frequency of administration for a therapeutic. When a clearance curve of a given molecule is constructed as a function of time, the curve is usually biphasic with a rapid "α-phase", which represents an equilibration of the injected molecules between the intra- and extra-vascular space and which is, in part, determined by the size of molecules; and a longer "β-phase", which represents the catabolism of the molecules in the intravascular space. In practical terms, the in vivo half-life usually corresponds closely to the half life of the molecules in the β-phase.

As used herein, the terms "nucleic acids" and "nucleotide sequences" include DNA molecules (e.g., cDNA or genomic DNA), RNA molecules (e.g., mRNA), combinations of DNA and RNA molecules or hybrid DNA/RNA molecules, and derivatives of DNA or RNA molecules. Such derivatives can be generated using, for example, nucleotides which include, but are not limited to, inosine or tritylated bases. Such derivatives can also comprise DNA or RNA molecules comprising modified backbones that lend beneficial attributes to the molecules such as, for example, nuclease resistance or an increased ability to cross cellular membranes. The nucleic acids or nucleotide sequences can be single-stranded, double-stranded, may contain both single-stranded and double-stranded portions, and may contain triple-stranded portions, but preferably are double-stranded DNA.

An "isolated" or "purified" molecule is substantially free of cellular material or other contaminants from the cell or tissue source from which the molecule is derived, or substantially free of chemical precursors or other chemicals when chemically synthesized. The language "substantially free of cellular material" includes preparations of molecule in which the molecule is separated from cellular components of the cells from which it is isolated or recombinantly produced. Thus, a protein that is substantially free of cellular material includes preparations having less than about 30%, 20%, 10%, or 5% (by dry weight) of contaminating protein. When the molecule, typically a protein, is recombinantly produced, it is also typically substantially free of culture medium, i.e., culture medium represents less than about 30%, 20%, 10%, or 5% of the volume of the preparation. When the molecule is produced by chemical synthesis, it is typically substantially free of chemical precursors or other chemicals, i.e., it is separated from chemical precursors or other chemicals which are involved in the synthesis of the molecule. Accordingly such preparations have less than about 30%, 20%, 10%, 5% (by dry weight) of chemical precursors or compounds other than the molecule of interest. In one embodiment of the present invention, proteins, and in particular single domain antibodies and fusion proteins thereof, are isolated or purified.

As used herein, the terms "subject," "host" and "patient" are used interchangeably. A subject is typically a mammal such as a non-primate (e.g., cows, pigs, horses, cats, dogs, rats etc.) or a primate (e.g., monkey and human), most often a human.

2. Anti-TNF-Alpha Polypeptides

One aspect of the instant invention relates to polypeptides directed against tumor necrosis factor-alpha (TNF-alpha), or antigen-binding fragments thereof. Such polypeptides are referred to herein as "anti-TNF-alpha polypeptides" and include, e.g., antigen-binding fragments thereof and derivatives thereof, as well as fusions thereof, such as fusions with an albumin-binding domain. The anti-TNF-alpha polypeptides of the invention comprise one or more immunoglobulin single domains, commonly referred to as "single domain antibodies", which is used herein interchangeably with the expression "antibody single domains". Anti-TNF-alpha polypeptides, along with nucleic acids encoding same and pharmaceutical compositions comprising same, may be referred to herein as "anti-TNF-alpha agents."

Antibody fragments can be generated from an intact conventional IgG and include antigen-binding fragments, Fc domains, Fab fragments (F(ab)), F(ab') fragments, single-chain Fv fragments (scFv) (VH-VL dimer), heavy chain domains only, light chain domains only, as well as individual (single) domains, e.g., VH domain, VL domain, $CH_1$ domain, $CH_2$ domain, $CH_3$ domain, CL domain, etc. The anti-TNF-alpha polypeptides in accordance with the invention may involve light chain antibodies, single domain antibodies derived from conventional 4-chain antibodies, engineered antibodies, and single domain scaffolds other than those derived from antibodies.

The terms "antibody single domain", "single domain antibody", or "sdAb" refer to antibody fragments that comprise or consist of either a VH or VL domain of an antibody, that is, a single monomeric variable antibody domain. In some embodiments, the antibody comprises dimers, trimers, or higher order multiples, thereof. Like an intact antibody, an antibody single domain can immunospecifically bind a specific antigen. Unlike whole antibodies, however, antibody single domains do not exhibit complement system triggered cytotoxicity, as they lack an Fc region.

Antibody single domains often have peptide chains of about 110 amino acids in length and molecular weights in the range of about 12 to about 15 kDa. Antibody single domains are thus much smaller than intact antibodies, which generally are about 150 to about 160 kDa, being composed of two heavy chains and two light chains. Antibody single domains are also smaller than Fab fragments (about 50 kDa; one light chain and half a heavy chain) and single-chain variable fragments (about 25 kDa; a light chain variable domain and a heavy chain variable domain). See, e.g., Harmsen, M M, et al. (2007) *Appl. Microbiol. Biotechnol.* 77(1): 13-22.

The small size of antibody single domains allows better solubility and better permeability in tissues, as well as greater heat-resistance and stability towards detergents and urea. Small size often leads also to a short serum half-life, as smaller molecules are eliminated renally more readily. Nonetheless, small size facilitates binding to "hidden" epitopes that may be not accessible to intact antibodies or larger antibody fragments, e.g., hidden active sites of enzymes or binding sites within grooves formed between multimeric polypeptides (such as in the case of the receptor binding site of TNF-alpha, as described above).

Early sdAbs were engineered from heavy-chain antibodies found in camelids. These sdAbs are often referred to as "VHH fragments." Most research involving sdAbs still focuses on heavy chain variable domains.

Anti-TNF-alpha polypeptides of the invention can include antibody single domains derived from any species (e.g., rabbit, mouse, rat, goat, bovine, Camelidae (camel, llama), and human immunoglobulin molecules). In some embodiments, the variable domain of a polypeptide in accordance with the invention is a rabbit variable domain. In some embodiments, the variable domain of a polypeptide in accordance with the invention is not a Camelidae variable domain. The immunoglobulin also may be of any type (e.g., IgG, IgE, IgM, IgD, IgA and IgY) and/or class (e.g., $IgG_1$, $IgG_2$, $IgG_3$, $IgG_4$, $IgA_1$, and $IgA_2$) and/or subclass. In some embodiments, domains of IgG are used.

In certain embodiments, the anti-TNF-alpha polypeptide of the invention, or antigen-binding fragment thereof, specifically excludes one or more antibody domains found in intact naturally-occurring immunoglobulins. For example, an anti-TNF-alpha polypeptide in accordance with the invention may comprise one or more single domains other than an Fc domain, Fab fragments (F(ab)) or F(ab') fragments. In some embodiments, the anti-TNF-alpha polypeptide of the invention comprises or consists of single-chain Fv fragments (scFv) (VH-VL dimer), heavy chain domains only, light chain domains only, as well as individual (single) domains only, e.g., a VH domain or a VL domain, or dimers, trimers, or higher structures of antibody single domains, such as VL-VL dimers. In some embodiments, the polypeptide in accordance with the invention does not include an Fc domain.

In certain embodiments, the anti-TNF-alpha polypeptide of the invention, or antigen-binding fragment thereof, does not comprise a VH domain, e.g., a rabbit VH domain, and/or does not comprise a VH domain derived from any species other than rabbit. In other embodiments, the polypeptide (or fragment thereof) does not comprise a VL domain and/or does not comprise a VL domain derived from any species other than rabbit. In certain embodiments, anti-TNF-alpha polypeptide of the invention, or antigen-binding fragment thereof, does not comprise a $CH_1$ domain and/or does not comprise a $CH_1$ domain derived from any species other than rabbit. In certain embodiments, the anti-TNF-alpha polypeptide of the invention, or antigen-binding fragment thereof, does not comprise a VH domain, e.g., a human VH domain, and/or does not comprise a VH domain derived from any species other than human. In other embodiments, the polypeptide (or fragment thereof) does not comprise a VL domain and/or does not comprise a VL domain derived from any species other than human. In certain embodiments, anti-TNF-alpha polypeptide of the invention, or antigen-binding fragment thereof, does not comprise a $CH_1$ domain and/or does not comprise a $CH_1$ domain derived from any species other than human.

In other embodiments, the anti-TNF-alpha polypeptide, or antigen-binding fragment thereof, does not comprise one or more of a $CH_1$ domain, $CH_2$ domain, CL domain, $CH_3$ domain, or H domain (hinge region), or does not comprise any of a $CH_1$ domain, $CH_2$ domain, CL domain, $CH_3$ domain, or H domain (hinge region). In still other embodiments, the anti-TNF-alpha polypeptide of the invention, or antigen-binding fragment thereof, comprises one of a $CH_1$ domain, H domain (hinge region), $CH_2$ domain, CL domain, or $CH_3$ domain, and does not comprise any other constant domain or hinge region derived from an immunoglobulin (for example, in certain embodiments, the anti-TNF-alpha polypeptide of the invention, or antigen-binding fragment thereof, comprises a $CH_1$ domain, but does not comprise any of an H domain (hinge region), a $CH_2$ domain, or a $CH_3$ domain; or comprises a $CH_2$ domain, but does not comprise any of a $CH_1$ domain, H domain (hinge region), or a $CH_3$ domain, etc). In some embodiments, the anti-TNF-alpha polypeptide of the invention, or antigen-binding fragment thereof, comprises only a heavy chain, only a light chain, only a VH domain, only a VL domain, or any combination of the above fragments and/or domains.

In some embodiments, the invention is directed to polypeptides comprising single domain antibody fragments, VH and/or VL. In some embodiments, the anti-TNF-alpha polpeptides in accordance with the invention may involve a single domain used as a monomer (e.g., a monomeric VH domain or VL domain). A VL or VH monomer may be selected based on its affinity and specificity for binding to one or more TNF-alpha molecules. Preferably, the selected VH or VL domain has a high binding affinity for human TNF-alpha. For example, sera from an animal immunized with TNF-alpha (e.g., an immunized rabbit) is analyzed for binding to one or more TNF-alpha molecules (e.g., human, rat, mouse, and/or monkey TNF-alpha), using techniques known in the art. Selected clones may be used to generate variable domain libraries, e.g., a VH and/or VL library to further select for suitable anti-TNF-alpha polypeptides. Selection may be based on high binding to one or more TNF-alpha molecules and/or for cross-reactivity.

In some embodiments, clones are selected that show high binding to human TNF-alpha and cross-reactivity with rat and/or mouse TNF-alpha, or with TNF-alpha from one or more non-human species, preferably including a relatively small mammal other than a primate. Relatively small mammals may include a rat, mouse, guinea pig, hamster, etc. In some preferred embodiments, clones are selected that exhibit cross-reactivity to TNF-alpha from at least one rodent species and at least one non-rodent species. Rodent species include, e.g., rats, mice, squirrels, gerbils, porcupines, beavers, chipmunks, guinea pigs, and voles. Such clones provide anti-TNF-alpha polypeptides suitable for use in the invention, where therapeutic effect can be achieved in human patients, while in vivo testing for such, in terms of, e.g., efficacy and toxicology assays, can be conducted in rat and/or mice models, and/or in one rodent and one non-rodent species. That is, cross-reactivity allows certain in vivo (pre-clinical) testing of putative therapeutic polypeptides to be conducted in the animal whose TNF-alpha is a binding target for the putuative therapeutic, along with human TNF-alpha. For example, a putative therapeutic polypeptide that has binding affinity for rat TNF-alpha, as well as human TNF-alpha, may be tested, e.g., for toxicology, in rat models of rheumatoid arthritis. Rat and/or mice models provide a cost advantage over, e.g, primate models for pre-clinical work of putative therapeutic anti-TNF-alpha polypeptides in accordance with the invention. Deliberately selecting anti-TNF-alpha polypeptides for cross-reactivity in non-primates, e.g., rats and mice, can reduce primate use, especially in toxicology assessments, keeping down costs-to-market.

In some embodiments, the anti-TNF-alpha polypeptide is a heavy chain variable domain (VH) used as a monomer. In some embodiments, the anti-TNF-alpha polypeptide is a light chain variable domain (VL) used as a monomer. Such monomers may be obtained from selected clones of naturally-occurring antibodies. For example, a VL library may be constructed by extracting light chain variable domain RNA from selected clones, synthesizing corresponding cDNA and using same to generate a phage display library. Phage display technology can be used to increase the affinity of an antibody domain for a target antigen and/or epitope, such as a TNF-alpha molecule. The technology, referred to as affinity maturation, employs mutagenesis or CDR walking and re-selection using target antigen and/or an epitope thereof to identify amino acid sequences of the invention that bind with higher affinity to TNF-alpha when compared with the initial pool of selected sequences. Libraries can be constructed having a pool of variant clones each of which differs by a single amino acid alteration in a single CDR and which contain variants representing each possible amino acid substitution for each CDR residue. Domains with increased binding affinity for the antigen can be screened, for example, by contacting the immobilized mutant domains with labeled antigen. Any screening method known in the art can be used to identify mutant antibodies with increased avidity to the antigen (e.g., ELISA) (See Wu et al., 1998, *Proc Natl. Acad. Sci. USA* 95:6037; Yelton et al., 1995, *J. Immunology* 155:1994, each of which is hereby incorporated by reference herein in its entirety). Variable light chain domains may be screened for affinity, specificity, and/or cross-reactivity with respect to one or more TNF-alpha molecules, as described above.

Figure 1:
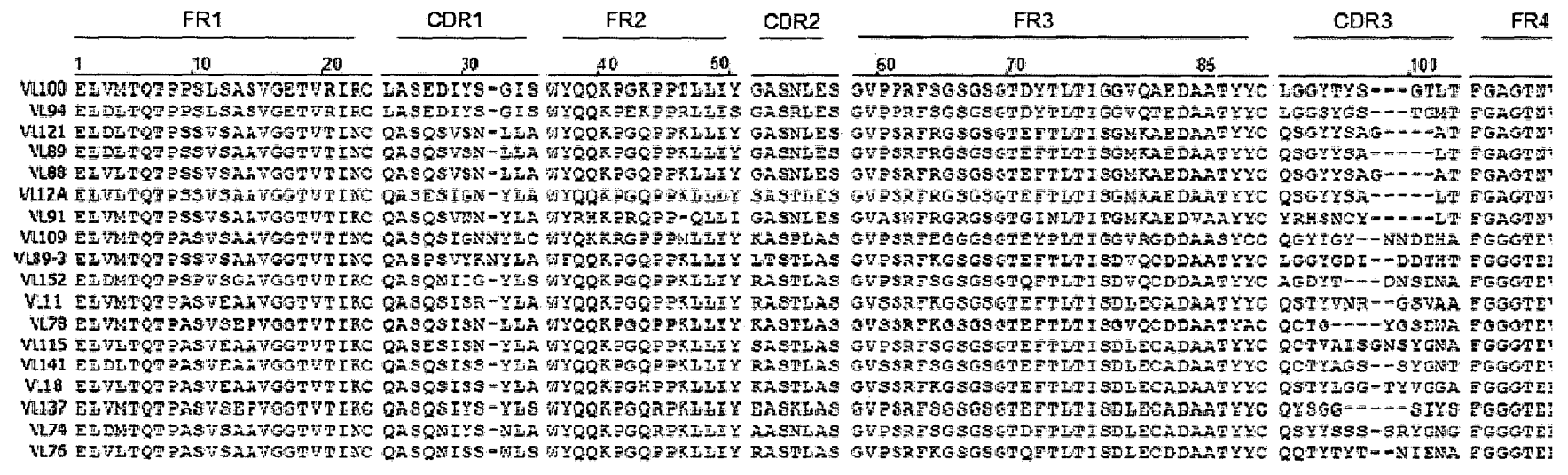

In particularly preferred embodiments, the anti-TNF-alpha polypeptide comprises a light chain variable domain that comprises or consists of an amino acid sequence selected from the group consisting of SEQ ID NOs: 1 to 18. See also Example 1 and FIG. 1.

In some embodiments, the anti-TNF-alpha polypeptide in accordance with the invention comprises more than one single domain of an immunoglobulin, in higher order format, e.g., as a dimer, trimer, tetramer, etc. In some embodiments, the anti-TNF-alpha polypeptide comprises two antibody single domains, or antigen-binding fragments thereof, in the form of a dimer. Dimer formats include, e.g., VH-VH dimers, VL-VL dimers, and VH-VL dimers. The VH-VH and VL-VL dimers may homodimers or heterodimers. In some preferred embodiments, the anti-TNF-alpha polypeptide comprises two different VL domains (VL1-VL2), each VL single domain being directed against a TNF-alpha molecule. In specific embodiments, the anti-TNF-alpha polypeptide comprises a VL-VL homo- or heterodimer, wherein one or both of the VL domains comprises an amino acid sequence selected from the group consisting of SEQ ID NOs: 1 to 18. Dimeric forms can provide two binding domains, facilitating more effective binding to the target molecule, and consequently more effective TNF-alpha blocking and/or inhibition.

In forming a dimer, the individual domains may be linked by a variety of methods, as known in the art. In some embodiments, the individual single domains are linked directly, e.g., by di-sulfide bonds.

In some embodiments, the individual single domains are linked by a linker, e.g., a peptide linker or chemical linker. Examples of chemical linkers include, without limitation, a maleimide linker, a biocompatible polymer (preferably with a length of about 1 to about 100 atoms), aldehyde/Schiff base linkage, suphydryl linkage, and the like. See, e.g., US Patent Publication Application No. 2011/0196085 to Selinfreund.

Alternatively, a peptide linker may be used, e.g., where the polypeptide constructs are expressed as fusion proteins along with a connecting linker. Peptide linkers often comprise flexible amino acid residues, such as glycine and serine, so that adjacent domains are free to move relative to one another. In preferred embodiments, the linker is of a length such that the two single domains are bridged without substantially affecting binding to the target TNF-alpha molecule(s). In some embodiments, the peptide linker used is 2 to 100 amino acids in length, 5 to 80, 10 to 50, 10 to 20, or 15 to 20 amino acids in length. Examples of peptide linkers include, without limitation, polyglycine, polyserine, polylysine, polyglutamate, polyisoleucine, or polyarginine residues, or combinations thereof. In a specific embodiment, the polyglycine or polyserine linkers include at least 5, 6, 7, 8, 9, 10, 12, 15, 20, 30, and 40 glycine and/or serine residues. In another specific embodiment, the linker involves repeats of glycine and serine residues, e.g., (Gly-Ser)$_n$ residues, or (Gly-Ser)$_n$ residues with Glu or Lys residues dispersed throughout, e.g., to increase solubility. Other linkers comprising glycine and serine repeats include, e.g., (Gly)$_4$-Ser repeats (SEQ ID NO: 45); Gly-Gly-Ser-Gly repeats (SEQ ID NO: 46); Gly-Gly-Ser-Gly-Gly-Ser repeats (SEQ ID NO: 47); or (Gly)$_4$-Ser-(Gly)$_3$-Ser repeats (SEQ ID NO: 48); each at one, two, three, four, five, six, seven or more repeats. Standard linkers include (GGGGS) (SEQ ID NO: 45); (GGGGS)$_2$ (SEQ ID NO: 49); (GGGGS)$_3$ (SEQ ID NO: 50); (GGGGS)$_4$ (SEQ ID NO: 51); (GGGGS)$_5$ (SEQ ID NO: 52); (GGGGS)$_6$ (SEQ ID NO: 53). In some particular embodiments, the linker comprises repeats according to the formula [Ser-(Gly)$_4$]$_n$-(Ser)$_2$-Gly-, where n is 1, 2, 3, 4, 5, or 7 (SEQ ID NO: 62). In other embodiments, n is 6, 8, 9, 10, or higher interger.

In another specific embodiment, the linker includes proline and threonine residues, e.g., a ((PT)3T(PT)3T(PT)3S) (SEQ ID NO: 59) linker. Additional peptide linkers are provided in Argos P. "An investigation of oligopeptides linking domains in protein tertiary structures and possible candidates for general gene fusion." *J Mol Biol* 211(4): 943-58, 1990; Crasto, C J et al. "LINKER: a program to generate linker sequences for fusion proteins." *Protein Eng* 13(5): 309-12, 2000; George, R A et al. "An analysis of protein domain linkers: their classification and role in protein folding." *Protein Eng* 15(11): 871-9, 2002; and Arai R, et al. "Design of the linkers which effectively separate domains of a bifunctional fusion protein." *Protein Eng* 14(8): 529-32, 2001, each of which is herein incorporated by reference in its entirety.

In some embodiments, the linker is a peptide linker comprising the amino acid sequence corresponding to SEQ ID NO: 29, which is also referred to herein as "3L". In some embodiments, the linker is a peptide linker comprising a derivative of the amino acid sequence of SEQ ID NO: 29, wherein the derivative differs by one or more amino acid residues from the amino acid sequence of SEQ ID NO: 29 but maintains the desired functionality of the linker. For example, 3L derivatives for use in accordance with the invention generally maintain the ability to link VL domains in such a way as to allow or improve immunospecific binding of the VL-VL dimer to a TNF-alpha molecule.

The dimer can be constructed using a two-step cloning strategy, where the carboxy terminal VL is cloned in a first step followed by the other VL in a second step, into a plasmid, which then is used to transform cells that can express the dimeric construct. Dimer formation may be confirmed, e.g, by Western Blot analysis, where dimeric forms are expected to have approximately twice the size and molecular weight of their monomeric constituents. See Example 2 and FIGS. 2A-C.

As described with respect to monomer forms, one or both of the single domains constituting the dimer may exhibit high affinity to a TNF-alpha molecule, preferably human TNF-alpha, and/or may exhibit cross-reactivity to TNF-alpha from one or more non-human species, preferably including rat, mouse, or other small mammal other than a primate. In some preferred embodiments, one or both of the single domains constituting the dimer may exhibit cross-reactivity to TNF-alpha from at least one rodent species and at least one non-rodent species. Rodent species include, e.g., rats, mice, squirrels, gerbils, porcupines, beavers, chipmunks, guinea pigs, and voles. As described above, cross-reactivity allows for in vivo assays in non-primate animals, where use of non-primate small mammals facilitates less expensive pre-clinical work. See Example 2 and FIG. 2D.

In a particularly preferred embodiment, the anti-TNF-alpha polypeptide comprises or consists of a light chain variable domain that comprises an amino acid sequence corresponding to SEQ ID NO:1 or SEQ ID NO:2, or both as a heterodimer. Herein, SEQ ID NO:1 may be referred to as "VL18"; whereas SEQ ID NO:2 may be referred to as "VL11".

In some embodiments, the anti-TNF-alpha polypeptide of the invention comprises a TNF-alpha-binding fragment of VL18 and/or VL11 comprising at least 10 contiguous amino acids of SEQ ID NO:1 and/or 2, respectively. In other embodiments, the polypeptide comprises a TNF-alpha-binding fragment of VL18 and/or VL11 comprising at least 15 contiguous amino acids of SEQ ID NO:1 and/or 2, respectively. In other embodiments, the polypeptide comprises a TNF-alpha-binding fragment of VL18 and/or VL11 comprising at least 20 contiguous amino acids of SEQ ID NO:1 and/or 2, respectively. In other embodiments, the polypeptide comprises a TNF-alpha-binding fragment of VL18 and/or VL11 comprising at least 25 contiguous amino acids of SEQ ID NO:1 and/or 2, respectively. In other embodiments, the polypeptide comprises a TNF-alpha-binding fragment of VL18 and/or VL11 comprising at least 30 contiguous amino acids of SEQ ID NO:1 and/or 2, respectively. In other embodiments, the polypeptide comprises a TNF-alpha-binding fragment of VL18 and/or VL11 comprising at least 35 contiguous amino acids of SEQ ID NO:1 and/or 2, respectively. In other embodiments, the polypeptide comprises a TNF-alpha-binding fragment of VL18 and/or VL11 comprising at least 40 contiguous amino acids of SEQ ID NO:1 and/or 2, respectively.

In some embodiments, the anti-TNF-alpha polypeptide of the invention comprises an amino acid sequence corresponding to a derivative of the amino acid sequence of SEQ ID NO:1 and/or 2. In some embodiments, the anti-TNF-alpha polypeptide of the invention has at least 45%, at least 50%, at least 55%, at least 60%, at least 65%, at least 70%, at least 75%, at least 80%, at least 85%, at least 90%, at least 95%, at least 98%, or at least 99% sequence identity to the amino acid sequence of SEQ ID NO:1 and/or 2.

In certain embodiments, the invention encompasses an anti-TNF-alpha polypeptide that comprises 1, 2, 3, 4, 5, 6, 7, 8, 9, 10, or more amino acid modifications (e.g., insertion, substitution, deletion, etc.) relative to the amino acid sequence SEQ ID NO:1 and/or 2. Amino acid sequence derivatives of the polypeptides of the invention can be created such that they are substitutional, insertional or deletion derivatives. Deletion derivatives lack one or more residues of the native polypeptide which are not essential for function (e.g., TNF-binding). Insertional mutants typically involve the addition of material at a non-terminal point in the polypeptide. Substitutional derivatives typically contain the exchange of one amino acid for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

Preferably, mutation of the amino acids of a protein creates an equivalent, or even an improved, second-generation molecule. For example, certain amino acids may be substituted for other amino acids in a protein structure without detectable loss of function (e.g., TNF-alpha-binding). In making such changes, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, interaction with a TNF-alpha molecule. Each amino acid has been assigned a hydropathic index on the basis of their hydrophobicity and charge characteristics; for example: isoleucine(+4.5); valine(+4.2); leucine(+3.8); phenylalanine (+2.8); cysteine/cystine(+2.5); methionine(+1.9); alanine(+1.8); glycine(−0.4); threonine(−0.7); serine(−0.8); tryptophan 0.9); tyrosine(−1.3); proline(−1.6); histidine(−3.2); glutamate(−3.5); glutamine(−3.5); aspartate (−3.5); asparagine (−3.5); lysine (−3.9); and arginine (−4.5). It is also understood in the art that the substitution of like amino acids can be made effectively on the basis of hydrophilicity. Like hydrophobicity, values of hydrophilicity have been assigned to each amino acid: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In general, equivalent molecules may be obtained by substitution of one amino acid for another where their hydrophilicity indices are within ±2, preferably ±1, or most preferably ±0.5 of each other.

An anti-TNF-alpha polypeptide according to the invention, e.g., a polypeptide comprising a monomer or dimer of single domains, binds human TNF-alpha so as to antagonize binding of the TNF-alpha molecule to a TNF-alpha receptor. In preferred embodiments, the anti-TNF alpha polypeptide can produce a therapeutic effect in one or more TNF-alpha-related conditions, as discussed in more detail below.

Binding assays known in the art that may be used in analyzing the binding and/or cross-reactivity of anti-TNF-alpha polypeptides, include any techniques for detecting specific binding to a binding partner, such as using any immunological or biochemical based method known in the art for characterizing binding-pair interactions. Specific binding may be determined for example using any art-known immunological or biochemical based methods including, but not limited to, an ELISA assay, surface plasmon resonance assays, immunoprecipitation assay, affinity chromatography, and equilibrium dialysis.

Immunoassays which can be used to analyze immunospecific binding and cross-reactivity of the anti-TNF-alpha polypeptides of the invention include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, and protein A immunoassays, to name a few. Such assays are routine and well known in the art (see, e.g., Ausubel et al., eds, 1994, Current Protocols in Molecular Biology, Vol. 1, John Wiley & Sons, Inc., New York, which is incorporated by reference herein in its entirety).

The anti-TNF-alpha polypeptides of the invention may also be assayed using any surface plasmon resonance based assays known in the art for characterizing the kinetic parameters of the interaction of an immunospecific protein with an antigen and/or epitope of interest (a TNF-alpha molecule). Any SPR instrument commercially available may be used including, but not limited to, BIAcore Instruments, available from Biacore AB (Uppsala, Sweden); IAsys instruments available from Affinity Sensors (Franklin, Mass.); IBIS system available from Windsor Scientific Limited (Berks, UK); SPR-CELLIA systems available from Nippon Laser and Electronics Lab (Hokkaido, Japan); and SPR Detector Spreeta available from Texas Instruments (Dallas, Tex.). For a review of SPR-based technology see Mullet et al., 2000, *Methods* 22: 77-91; Dong et al., 2002, *Review in Mol. Biotech.*, 82: 303-23; Fivash et al., 1998, *Current Opinion in Biotechnology* 9: 97-101; Rich et al., 2000, *Current Opinion in Biotechnology* 11: 54-61; all of which are incorporated herein by reference in their entireties. Additionally, any of the SPR instruments and SPR-based methods for measuring protein-protein interactions described in U.S. Pat. Nos. 6,373, 577; 6,289,286; 5,322,798; 5,341,215; and 6,268,125 are contemplated in the methods of the invention, all of which are incorporated herein by reference in their entireties.

In preferred embodiments, the anti-TNF-alpha polypeptide of the invention comprises a heterodimer of VL dimers, said dimer having a high binding affinity for human TNF-alpha, or antigen-binding fragment thereof. In a specific embodiment, e.g., the anti-TNF-alpha polypeptide may antagonize binding of human (or other) TNF-alpha to one or more of its cognate receptors by at least 10%, at least 15%, at least 20%, at least 25%, at least 30%, at least 35%, at least 40%, at least 45%, at least 50%, at least 60%, at least 70%, at least 80%, at least 90%, or more.

In some embodiments, the affinity to human (or other) TNF-alpha of the anti-TNF-alpha polypeptide, or antigen-binding fragment thereof, is at least $0.5 \times 10^9$ M$^{-1}$. In other instances, the affinity is at least $1 \times 10^4$ M$^{-1}$, at least $1 \times 10^5$ M$^{-1}$, at least $1 \times 10^6$ M$^{-1}$, at least $1 \times 10^7$ M$^{-1}$, at least $1 \times 10^8$ M$^{-1}$, at least $1 \times 10^9$ M$^{-1}$, at least $2 \times 10^9$ M$^{-1}$, at least $3 \times 10^9$ M$^{-1}$, at least $4 \times 10^9$ M$^{-1}$, at least $5 \times 10^9$ M$^{-1}$, at least $6 \times 10^9$ M$^{-1}$, at least $7 \times 10^9$ M$^{-1}$, at least $8 \times 10^9$ M$^{-1}$, or at least $9 \times 10^9$ M$^{-1}$. Affinity binding can be measured by any technique known in the art, as described above.

In a specific embodiment, the anti-TNF-alpha polypeptide of the invention, or antigen-binding fragment thereof, has an association rate constant or $k_{on}$ rate of at least $10^3$ M$^{-1}$ s$^{-1}$, at least $2 \times 10^3$ M$^{-1}$ s$^{-1}$, at least $3 \times 10^3$ M$^{-1}$ s$^{-1}$, at least $5 \times 10^3$ M$^{-1}$ s$^{-1}$, at least $8 \times 10^3$ M$^{-1}$ s$^{-1}$, at least $10^4$ M$^{-1}$ s$^{-1}$, at least $2 \times 10^4$ M$^{-1}$ s$^{-1}$, at least $3 \times 10^4$ M$^{-1}$ s$^{-1}$, at least $5 \times 10^4$ M$^{-1}$ s$^{-1}$, at least $7 \times 10^4$ M$^{-1}$ s$^{-1}$, at least $8 \times 10^4$ M$^{-1}$ s$^-$, at least $10^5$ M$^{-1}$ s$^{-1}$, at least $5 \times 10^5$ M$^{-1}$ s$^{-1}$, at least $10^6$ M$^{-1}$ s$^{-1}$, at least $5 \times 10^6$ M$^{-1}$ s$^{-1}$, at least $10^7$ M$^{-1}$ s$^{-1}$, at least $5 \times 10^7$ M$^{-1}$ s$^{-1}$, or at least $10^8$ M$^{-1}$ s$^{-1}$. In a specific embodiment, the anti-TNF-alpha polypeptide of the invention, or antigen-binding fragment thereof, has a dissociation rate constant or $k_{off}$ rate of at least $10^{-6}$ s$^{-1}$, at least $5 \times 10^{-6}$ s$^{-1}$, at least $10^{-5}$ s$^{-1}$, at least $5 \times 10^{-5}$ s$^{-1}$, at least $10^{-4}$ s$^{-1}$, at least $5 \times 10^{-4}$ s$^{-1}$, or at least $10^{-3}$ s$^{-1}$. In a specific embodiment, the anti-TNF-alpha polypeptide of the invention, or antigen-binding fragment thereof, has a Kd of at least 1 nM, at least 1.5 nM, at least 2 nM, at least 2.5 nM, at least 3 nM, at least 3.5 nM, at least 4 nM, at least 4.5 nM, at least 5 nM, at least 5.5 nM, at least 6 nM, at least 6.5, nM, at least 7 nM, at least 8 nM, at least 10 nM, at least 20 nM, at least 30 nM, at least 40 nM, at least 45 nM, or at least 50 nM.

In particular embodiments, one or both of the VL domains of a VL-VL dimer of the invention comprises an amino acid sequence selected from the group consisting of SEQ ID NO:1 (VL18) and SEQ ID NO:2 (VL11), or a TNF-alpha-binding fragment or derivative thereof for one or both sequences. For example, a polypeptide of the invention may comprise a dimer selected from the group consisting of VL18-VL18; VL18-VL11; VL11-VL11; VL11-VL18, or an antigen-binding fragment or derivative thereof for one or both of the individual VL dimers (as detailed above, for example). In some embodiments, a linker such as a peptide linker, occurs between the individual domains comprising a dimer of the invention.

In some embodiments, the anti-TNF-alpha polypeptide of the invention is a dimer comprising one or both of SEQ ID NOs: 1 and 2. In some embodiments, one or both VL domains of the dimer has at least 45%, at least 50%, at least 55%, at least 60%, at least 65%, at least 70%, at least 75%, at least 80%, at least 85%, at least 90%, at least 95%, at least 98%, or at least 99% sequence identity to SEQ ID NO: 1 or 2.

In certain embodiments, the invention encompasses a dimeric anti-TNF-alpha polypeptide that comprises one or both of SEQ ID NOs: 1 and 2, wherein at least one of which has been modified. In certain embodiments, the polypeptide comprises 1, 2, 3, 4, 5, 6, 7, 8, 9, 10, or more amino acid modifications (e.g., insertion, substitution, deletion, etc.) relative to SEQ ID NOs: 1 and/or 2. Amino acid sequence derivatives of the polypeptides of the invention can be created such that they are substitutional, insertional or deletion derivatives, as detailed above.

In a particular embodiment, the polypeptide of the invention involves a VL-VL dimer comprising an amino acid sequence corresponding to SEQ ID NO:32 (VL18-3L-VL11), or a TNF-alpha-binding fragment thereof. In some embodiments, the anti-TNF-alpha polypeptide of the invention comprises an amino acid sequence corresponding to a derivative of the amino acid sequence of SEQ ID NO:32. In some embodiments, the anti-TNF-alpha polypeptide of the invention has at least 45%, at least 50%, at least 55%, at least 60%, at least 65%, at least 70%, at least 75%, at least 80%, at least 85%, at least 90%, at least 95%, at least 98%, or at least 99% sequence identity to the amino acid sequence of SEQ ID NO:32.

In certain embodiments, the invention encompasses an anti-TNF-alpha polypeptide that comprises 1, 2, 3, 4, 5, 6, 7, 8, 9, 10, or more amino acid modifications (e.g., insertion, substitution, deletion, etc.) relative to the amino acid sequence of SEQ ID NO. 32. Amino acid sequence derivatives of the polypeptides of the invention can be created such that they are substitutional, insertional or deletion derivatives, as detailed above.

In further specific embodiments, the anti-TNF-alpha polypeptide comprises a light chain variable domain, said variable domain comprising at least one sequence selected from the group consisting of SEQ ID NOs:3-18, and a TNF-alpha-binding fragment or derivative thereof.

In some embodiments, the anti-TNF-alpha polypeptide of the invention comprises a TNF-alpha-binding fragment of at least one sequence selected from the group consisting of SEQ ID NOs:3-18 comprising at least 10 contiguous amino acids of said sequence. In other embodiments, the anti-TNF-alpha polypeptide comprises a TNF-alpha-binding fragment of any one of more or SEQ ID NOs:3-18 comprising at least 15 contiguous amino acids of said sequence. In other embodiments, the anti-TNF-alpha polypeptide comprises a TNF-alpha-binding fragment of any one or more SEQ ID NOs:3-18 comprising at least 20 contiguous amino acids of said sequence. In other embodiments, the anti-TNF-alpha polypeptide comprises a TNF-alpha-binding fragment of any one or more of SEQ ID NOs:3-18 comprising at least 25 contiguous amino acids of said sequence. In other embodiments, the anti-TNF-alpha polypeptide comprises a TNF-alpha-binding fragment of any one or more of SEQ ID NOs: 3-18 comprising at least 30 contiguous amino acids of said sequence. In other embodiments, the anti-TNF-alpha polypeptide comprises a TNF-alpha-binding fragment of any one or more of SEQ ID NOs:3-18 comprising at least 35 contiguous amino acids of said sequence. In other embodiments, the anti-TNF-alpha polypeptide comprises a TNF-alpha-binding fragment of any one or more of SEQ ID NOs: 3-18 comprising at least 40 contiguous amino acids of said sequence.

In some embodiments, the anti-TNF-alpha polypeptide of the invention comprises an amino acid sequence corresponding to a derivative of any one or more of SEQ ID NOs:3-18. In some embodiments, the anti-TNF-alpha polypeptide has at least 45%, at least 50%, at least 55%, at least 60%, at least 65%, at least 70%, at least 75%, at least 80%, at least 85%, at least 90%, at least 95%, at least 98%, or at least 99% sequence identity to any one or more of SEQ ID NOs:3-18.

In certain embodiments, the invention encompasses an anti-TNF-alpha polypeptide that comprises 1, 2, 3, 4, 5, 6, 7, 8, 9, 10, or more amino acid modifications (e.g., insertion, substitution, deletion, etc.) relative to any one or more of SEQ ID NOs:3-18. Amino acid sequence derivatives of the polypeptides of the invention can be created such that they are substitutional, insertional or deletion derivatives, as described above.

In some embodiments, the amino acid modification occurs in one or more of the framework regions of a variable domain of a polypeptide of the invention. Mutations in a framework region may improve certain therapeutic parameters without affecting (or substantially affecting) binding of the polypeptide to its target (a TNF-alpha molecule). For example, in preferred embodiments, modifications in a framework region enhance the stability and/or half-life of the polypeptide. In some preferred embodiments, modifications in a framework region improve binding affinity of the polypeptide to its target or improve other binding parameters. In some embodiments, framework region mutations result in decreased immunogenicity, e.g., by destruction of a $T_H$ epitope occurring therein, as described in more detail below.

In some embodiments, the amino acid modification occurs in one or more CDRs of a variable domain of a polypeptide of the invention. Mutations in a CDR may improve certain therapeutic parameters, e.g., improving binding of the polypeptide to human TNF-alpha molecule and/or improved cross-reactivity to another non-human TNF-alpha molecule, preferably a TNF-alpha of a non-primate mammal, such as mice or rats, more preferably a TNF-alpha of both at least one rodent and at least one non-rodent species. In some embodiments, CDR mutations result in decreased immunogenicity, e.g., by destruction of a $T_H$ epitope occurring therein, as described in more detail below.

In some embodiments, amino acid modification occurs in both one or more framework regions and one or more CDRs, e.g., to provide a derivative having one or more improved therapeutic parameters, such as enhanced stability and/or half-life, improved binding and/or cross-reactivity, enhanced expression, increased solubility, and/or reduced immunogenicity. Additional approaches to improving therapeutic potential of a polypeptide of the invention include the creation of fusions with albumin-binding domains, as discussed in more detail below.

3. Anti-TNF-alpha Polypeptide Fusions with Albumin-Binding Domains

In some embodiments, an anti-TNF-alpha polypeptide in accordance with the invention is linked to an albumin-binding domain. Albumin-binding domains include any polypeptide that can bind albumin under physiological conditions. Coupling an anti-TNF-alpha polypeptide of the invention to an albumin-binding domain can allow in vivo association to serum albumins, which in turn can extend the half-life of the polypeptide, as well as improve solubility, and/or improve stability. Accordingly, albumin-binding domains can be used to make conjugates and/or fusions with therapeutic molecules to improve stability and/or serum half-life, preferably while maintaining bioavailability and/or bioactivity. Without being bound by theory, a preferred strategy involves high-affinity non-covalent interaction with albumin to improve serum half-life.

Examples of albumin-binding domains include albumin-binding peptides or proteins from streptococcal protein G (SpG), described e.g. in EP 0486525; U.S. Pat. No. 6,267, 964; Makrides, S. et al. (1996) *J. Pharmacol. Exp. Ther.* 277, 534-542; and Sjolander, A et al. (1997) *J. Immunol. Methods* 201, 115-123. Additional albumin-binding protein sequences are provided in, e.g., PCT Publication No. WO 91/19741, PCT Publication No. WO 05/097202, PCT Publication No. WO 01/45746; U.S. Patent Publication No. 2004/0001827; and Konig T, et al. *J Immunol Methods.* 218 (1-2): 73-83, 1998.

Another albumin-binding protein involves protein MAG, a protein isolated from *Streptococcus dysgalactiae* stains found in cases of bovine mastitis (see, e.g., Jonsson, H. et al. (1994) *Gene* 143: 85-89; and Jonsson, H. et al. (1994) *Eur. J. Biochem.* 220: 819-826). Protein MAG binds serum albumin via a 50-amino acid stretch in the middle of the polypeptide, which is partially homologous to the albumin-binding domain of protein G. Another albumin-binding protein involves DG12 protein, a protein isolated from a bovine group G *streptococcus* (see, e.g., Sjobring, U. (1993) *Infect. Immun.* 60: 3601-3608). Still another albumin-binding protein involves protein PAB, isolated from *Peptostreptococcus magnus* (see, e.g., de Chateau, M. et al. (1994) *J. Biol. Chem.* 269: 12147-12151). This protein contains a short albumin-binding domain with homology to certain streptococcal albumin-binding domains. Still another related albumin-binding domain involves protein EAG, isolated from some strains of *Streptococcus equi*.

In some embodiments, the albumin-binding domain comprises one isolated and/or derived from protein H, a molecule expressed at the surface of some strains of *Streptococcus pyogenes* (see, e.g., Nilson, et al. (1995) *Biochem.* 34:13688-98). *Streptococcus pyogenes* bacteria are responsible for a number of suppurative infections in humans, such as acute pharyngitis and skin infections. It is known that protein H has affinity for the constant region of immunoglobulin G (IgGFc), as well as for plasma albumin (Frick I M, et al. (1994) *Mol Microbiol.* 12:143-51). Albumin-binding domains of protein H may bind human, rat, and/or mouse serum albumin. In some embodiments, there is cross-reactivity of albumin-binding domain of protein H to rat, mouse, and human albumins. The albumin-binding domain of protein H corresponds to a three repeat region, termed "C1C2C3" or "C1-C3" in the C-terminal half of protein H. This albumin-binding domain can be determined, e.g., by analyzing the binding of albumin to protein H to map the binding region. The albumin-binding domain region corresponds roughly to the C-terminal cell-wall-attached region. Interestingly, the affinity constant of the protein H binding region for albumin is higher than that for IgG, that is, the affinity constant for the reaction between albumin and protein H domain (C1C2C3) is $7.8 \times 10^9$ $M^{-1}$, which is higher than the affinity ($K_a = 1.6 \times 10^9$ $M^{-1}$) between IgG and protein H domain (C1C2C3).

In some embodiments, the albumin-binding domain comprises one isolated and/or derived from a protein G-related cell surface protein, expressed in some strains of *Streptococcus zooepidemicus* (see, e.g., Jonsson, et al. (1995) *Infection and Immunity.* 63(8): 2968-2975). *Streptococcus zooepidemicus* bacteria are common etiological agents in a variety of horse diseases. *S. zooepidemicus* specifically binds, through cell surface components, to a number of host proteins, including immunoglobulin G (IgG), serum albumin, fibronectin, collagen, and $\alpha_2$-macroglobulin ($\alpha_2 M$). (see, e.g., Wideback, K. et al. (1983) *Acta Pathol. Microbiol. Immunol. Scand. Sect. B* 91: 373-382). One particular albumin-binding protein is isolated from *S. zooepidemicus* Z5. Nygren, P., et al. (1990) *Eur. J. Biochem.* 1993: 143-148).

In particular embodiments, the albumin-binding domain comprises or consists of an amino acid sequence corresponding to SEQ ID NO:30, which also may be referred to herein as "PEP." In some embodiments, an albumin-binding fragment of SEQ ID NO:30 is used. In some embodiments, the albumin-binding domain comprises or consists of an albumin-binding fragment of protein PEP comprising at least 10 contiguous amino acids of SEQ ID NO:30. In other embodiments, the albumin-binding domain comprises an albumin binding-fragment of PEP comprising at least 15 contiguous amino acids of SEQ ID NO:30. In other embodiments, the albumin-binding domain comprises an albumin-binding fragment of PEP comprising at least 20 contiguous amino acids of SEQ ID NO:30. In other embodiments, the albumin-binding domain comprises an albumin-binding fragment of PEP comprising at least 25 contiguous amino acids of SEQ ID NO:30. In other embodiments, the albumin-binding domain comprises an albumin-binding fragment of PEP comprising at least 30 contiguous amino acids of SEQ ID NO:30. In other embodiments, the albumin-binding domain comprises an albumin-binding fragment of PEP comprising at least 35 contiguous amino acids of SEQ ID NO:30. In other embodiments, the albumin-binding domain comprises an albumin-binding fragment of PEP comprising at least 40 contiguous amino acids of SEQ ID NO:30.

In still other embodiments, the albumin-binding domain comprises or consists of at least two fragments of PEP that together bind albumin and that each independently include at least 10 contiguous amino acids of SEQ ID NO:30. In yet other embodiments, the albumin-binding domain comprises at least two fragments of PEP that together bind albumin and that each independently include at least 15 contiguous amino acids of SEQ ID NO:30. In yet other embodiments, the albumin-binding domain comprises at least two fragments of PEP that together bind albumin and that each independently include at least 20 contiguous amino acids of SEQ ID NO:30. In yet still further embodiments, the albumin-binding domain comprises or consists of at least 10, at least 20, at least 30, at least 40, or at least 50 contiguous amino acids of SEQ ID NO:30.

In some embodiments, the albumin-binding domain comprises or consists of an amino acid sequence corresponding to a derivative of the amino acid sequence of SEQ ID NO:30. In some instances, the albumin-binding domain has at least 45%, at least 50%, at least 55%, at least 60%, at least 65%, at least 70%, at least 75%, at least 80%, at least 85%, at least 90%, at least 95%, at least 98%, or at least 99% sequence identity to the amino acid sequence of SEQ ID NO:30.

In certain embodiments, the albumin-binding domain comprises 1, 2, 3, 4, 5, 6, 7, 8, 9, 10, or more amino acid modifications (e.g., insertion, substitution, deletion, etc.) relative to the amino acid sequence of SEQ ID NO:30. Amino acid sequence derivatives of the albumin-binding domain can be created such that they are substitutional, insertional or deletion derivatives, as detailed above with respect to derivatives of the anti-TNF-alpha polypeptides of the invention. The resulting derivatives may show improved solubility, improved stability and/or albumin binding, improved binding to human TNF-alpha and/or improved cross-reactivity to one or more non-primate mammalian TNF-alpha molecules, or to at least one rodent and at least one non-rodent species; reduced immunogenicity; or other advantageous feature described herein and/or known in the art.

In some instances, the affinity to albumin of an albumin-binding domain peptide, or of its conjugate or fusion with an anti-TNF-alpha polypeptide, is at least $0.5 \times 10^9$ $M^{-1}$. In other instances, the affinity is at least $1 \times 10^4$ $M^{-1}$, at least $1 \times 10^5$ $M^{-1}$, at least $1 \times 10^6$ $M^{-1}$, at least $1 \times 10^7$ $M^{-1}$, at least $1 \times 10^8$ $M^{-1}$, at least $1 \times 10^9$ $M^{-1}$, at least $2 \times 10^9$ $M^{-1}$, at least $3 \times 10^9$ $M^{-1}$, at least $4 \times 10^9$ $M^{-1}$, at least $5 \times 10^9$ $M^{-1}$, at least $6 \times 10^9$ $M^{-1}$, at least $7 \times 10^9$ $M^{-1}$, at least $8 \times 10^9$ $M^{-1}$, or at least $9 \times 10^9$ $M^{-1}$. Albumin binding can be measured by any technique known in the art. In certain instances, albumin binding is measured by an in vitro assay such as those described in, for e.g. Epps, et al. (1999) *J. Pharm. Pharmacol.* 51:41-48; Nguyen, et al. (2006) *Prot. Engin. Design Select.* 19:291-297; Weisiger, et al. (2001) *J. Biol. Chem.*, 276:29953-29960.

The albumin-binding domains can be linked to one or more anti-TNF-alpha polypeptides of the invention, including in particular to a single domain in monomer form (e.g., VL or VH) or to a dimer thereof (e.g., VL-VL). In preferred embodiments, the linkage is a fusion resulting in a product that binds to serum albumin while maintaining (or substantially maintaining) original binding affinity to a TNF-alpha molecule, as described in more detail below. Accordingly, in some embodiments, the anti-TNF-alpha polypeptide is linked to an albumin binding domain by fusion. Linkage can occur by any means known in the art, and may or may not include a linker. Linkers may include any of the linkers described above with respect to dimeric constructs, e.g., peptide linkers comprising (GGGGS (SEQ ID NO: 45)) repeats. Fusions typically are created using recombinant techniques, known in the art, and described in more detail below. See also Example 3.

The anti-TNF-alpha polypeptide fusions with an albumin-binding domain, in accordance with the invention, retain antigen binding specificity, i.e., binding specificity to a TNF-alpha molecule. Fusions can be tested for retention of binding specificity to a TNF-alpha molecule, where binding can be determined by any means known in the art, e.g., as detailed above. See also Example 4.

In preferred embodiments, the anti-TNF-alpha polypeptides linked to an albumin-binding domain in accordance with the invention show improved pharmacokinetics in vivo. In certain embodiments, linkage to PEP, or a derivative or albumin-binding fragment thereof, increases the half-life of the anti-TNF-alpha polypeptide in a host. In some embodiments, the half-life of the anti-TNF-alpha polypeptide in the host is increased by about 10%, by about 20%, by about 30%, by about 40%, by about 50%, by about 60%, by about 70%, by about 80%, by about 90%, by about 100%, by about 150%, by about 200%, by about 300%, by about 500%, by about 1000% or more. In other embodiments, linkage to PEP, or a derivative or albumin-binding fragment thereof, increases the half-life of the anti-TNF-alpha polypeptide in a host by at least double, at least 3 times, at least 4 times, at least 5 times, at least 6 times, at least 7 times, at least 8 times, at least 9 times, at least 10 times, or more compared with the half-life of the anti-TNF-alpha polypeptide alone (not linked to the albumin-binding domain). See also Example 5.

In preferred embodiments, the anti-TNF-alpha polypeptides linked to an albumin-binding domain in accordance with the invention have a half-life of at least about 10 hours, at least about 20 hours, at least about 30 hours, at least about 35 hours, at least about 40 hours, at least about 45 hours, at least about 50 hours, or at least about 55 hours. In some particular embodiments, the anti-TNF-alpha polypeptides linked to an albumin-binding domain in accordance with the invention have a half-life of from about 35 to about 42 hours, e.g., where the construct corresponds to SEQ ID NO:33. For comparison, in some particular embodiments, the anti-TNF-alpha polypeptide not linked to albumin-binding domain may have a half-life of only about 2 to about 5 hours, e.g., where the dimer corresponds to SEQ ID NO:32.

In some embodiments, linkage to PEP, or a derivative or albumin-binding fragment thereof, reduces elimination of the anti-TNF-alpha polypeptide from the host by at least 1 day, by at least 2 days, by at least 3 days, by at least 4 days, by at least 5 days, by at least one week, or more. In some embodiments, anti-TNF-alpha polypeptide linked to PEP, or a derivative or an albumin-binding fragment thereof, has a serum half-life ($t_{1/2}$) of about 12 hours, of about 24 hours, of about 2 days, of about 3 days, of about 4 days, of about 5 days, of about 6 days, of about 7 days, of about 8 days, of about 9 days, of about 10 days, of about 11 days, of about 12 days, of about 13 days, of about 14 days, or more, such as for example, for about 3 weeks, about 4 weeks, or more.

In a specific embodiment, the anti-TNF-alpha polypeptide is fused with an albumin-binding domain to provide an agent comprising an amino acid sequence corresponding to SEQ. ID. NO: 33 (VL18-3L-VL11-PEP), or an antigen-binding fragment thereof. VL18-3L-VL11-PEP retains binding specificity to TNF-alpha, as detailed below. See Example 6 and Examples 7a and 7b, as well as FIGS. 3 and 4.

In specific preferred embodiments, the anti-TNF-alpha polypeptide of the invention binds to recombinant human TNF-alpha with affinities comparable to products on the market for treating rheumatoid arthritis (e.g., comparable to infliximab (Remicade™) and etanercept (Enbrel)). See also Table 1 below.

In some embodiments, the anti-TNF-alpha polypeptide-albumin-binding domain fusion of the invention comprises a TNF-alpha-binding fragment of VL18 and/or VL11 comprising or consisting of at least 10 contiguous amino acids of SEQ ID NO:1 and/or 2, respectively. In other embodiments, the fusion comprises a TNF-alpha-binding fragment of VL18 and/or VL11 comprising or consisting of at least 15 contiguous amino acids of SEQ ID NO:1 and/or 2, respectively. In other embodiments, the fusion comprises a TNF-alpha-binding fragment of VL18 and/or VL11 comprising or consisting of at least 20 contiguous amino acids of SEQ ID NO:1 and/or 2, respectively. In other embodiments, the fusion comprises a TNF-alpha-binding fragment of VL18 and/or VL11 comprising or consisting of at least 25 contiguous amino acids of SEQ ID NO:1 and/or 2, respectively. In other embodiments, the fusion comprises a TNF-alpha-binding fragment of VL18 and/or VL11 comprising or consisting of at least 30 contiguous amino acids of SEQ ID NO:1 and/or 2, respectively. In other embodiments, the fusion comprises a TNF-alpha-binding fragment of VL18 and/or VL11 comprising or consisting of at least 35 contiguous amino acids of SEQ ID NO:1 and/or 2, respectively. In other embodiments, the fusion comprises a TNF-alpha-binding fragment of VL18 and/or VL11 comprising or consisting of at least 40 contiguous amino acids of SEQ ID NO:1 and/or 2, respectively.

In some embodiments, the anti-TNF-alpha polypeptide-albumin-binding domain fusion of the invention comprises an amino acid sequence corresponding to a derivative of the amino acid sequence of SEQ ID NO:1 and/or 2. In some embodiments, the fusion has at least 45%, at least 50%, at least 55%, at least 60%, at least 65%, at least 70%, at least 75%, at least 80%, at least 85%, at least 90%, at least 95%, at least 98%, or at least 99% sequence identity to the amino acid sequence of SEQ ID NO:1 and/or 2.

In certain embodiments, the invention encompasses an anti-TNF-alpha polypeptide-albumin-binding domain fusion that comprises 1, 2, 3, 4, 5, 6, 7, 8, 9, 10, or more amino acid modifications (e.g., insertion, substitution, deletion, etc.) relative to the amino acid sequence of SEQ ID NO. 1 and/or SEQ ID NO. 2. Amino acid sequence derivatives of the polypeptides of the invention can be created such that they are substitutional, insertional or deletion derivatives, as described above.

In further specific embodiments, the anti-TNF-alpha polypeptide-albumin-binding domain comprises a light chain variable domain, said variable domain comprising at least one sequence selected from the group consisting of SEQ ID NOs: 3-18.

In some embodiments, the anti-TNF-alpha polypeptide-albumin-binding domain fusion of the invention comprises a TNF-alpha-binding fragment of at least one sequence selected from the group consisting of SEQ ID NOs:3-18 comprising or consisting of at least 10 contiguous amino acids of said sequence. In other embodiments, the fusion comprises a TNF-alpha-binding fragment of any one of more or SEQ ID NOs:3-18 comprising or consisting of at least 15 contiguous amino acids of said sequence. In other embodiments, the fusion comprises a TNF-alpha-binding fragment of any one or more SEQ ID NOs:3-18 comprising or consisting of at least 20 contiguous amino acids of said sequence. In other embodiments, the fusion comprises a TNF-alpha-binding fragment of any one or more of SEQ ID NOs:3-18 comprising or consisting of at least 25 contiguous amino acids of said sequence. In other embodiments, the fusion comprises a TNF-alpha-binding fragment of any one or more of SEQ ID NOs:3-18 comprising or consisting of at least 30 contiguous amino acids of said sequence. In other embodiments, the fusion comprises a TNF-alpha-binding fragment of any one or more of SEQ ID NOs:3-18 comprising or consisting of at least 35 contiguous amino acids of said sequence. In other embodiments, the fusion comprises a TNF-alpha-binding fragment of any one or more of SEQ ID NOs:3-18 comprising or consisting of at least 40 contiguous amino acids of said sequence.

In some embodiments, the anti-TNF-alpha polypeptide-albumin-binding domain fusion of the invention comprises an amino acid sequence corresponding to a derivative of any one or more of SEQ ID NOs:3-18. In some embodiments, the fusion has at least 45%, at least 50%, at least 55%, at least 60%, at least 65%, at least 70%, at least 75%, at least 80%, at least 85%, at least 90%, at least 95%, at least 98%, or at least 99% sequence identity to any one or more of SEQ ID NOs: 3-18.

In certain embodiments, the invention encompasses an anti-TNF-alpha polypeptide-albumin-binding domain fusion that comprises 1, 2, 3, 4, 5, 6, 7, 8, 9, 10, or more amino acid modifications (e.g., insertion, substitution, deletion, etc.) relative to any one or more of SEQ ID NOs:3-18. Amino acid sequence derivatives of the polypeptides of the invention can be created such that they are substitutional, insertional or deletion derivatives, as described above.

In some embodiments, the anti-TNF-alpha polypeptide-albumin-binding domain fusion of the invention comprises an amino acid sequence corresponding to a derivative of the amino acid sequence of SEQ ID NO:33. In some embodiments, fusion has at least 45%, at least 50%, at least 55%, at least 60%, at least 65%, at least 70%, at least 75%, at least 80%, at least 85%, at least 90%, at least 95%, at least 98%, or at least 99% sequence identity to the amino acid sequence of SEQ ID NO:33.

In certain embodiments, the invention encompasses an anti-TNF-alpha polypeptide-albumin-binding domain fusion that comprises 1, 2, 3, 4, 5, 6, 7, 8, 9, 10, or more amino acid modifications (e.g., insertion, substitution, deletion, etc.) relative to the amino acid sequence of SEQ ID NO:33. Amino acid sequence derivatives of the polypeptides of the invention can be created such that they are substitutional, insertional or deletion derivatives, as detail above.

In some embodiments, the amino acid modification occurs in one or more of the framework regions of a variable domain of a fusion of the invention, in one or more CDRs of a variable domain of the fusion, or both. Mutations in a framework region may improve certain therapeutic parameters without affecting (or substantially affecting) binding of the polypeptide to its target (a TNF-alpha molecule and/or serum albumin), or may improve binding. In preferred embodiments, modifications in a framework region further enhance the stability and/or half life of the polypeptide.

Mutations in a CDR also may improve certain therapeutic parameters, e.g., improving binding affinity of the polypeptide for human TNF-alpha molecule and/or improving cross-reactivity to another non-human TNF-alpha molecule, e.g., to a non-primate mammalian TNF-alpha molecule, or to at least one rodent and at least one non-rodent species, without affecting (or substantially affecting) binding affinity of the fusion for serum albumin. In some embodiments, mutations in any of the framework, CDR, or albumin-binding domains result in decreased immunogenicity, e.g., by destruction of a $T_H$ epitope occurring therein, as described in more detail below. In some embodiments, amino acid modification occurs in both one or more framework regions, CDRs, or albumin-binding domains, e.g., to provide a derivative having one or more improved therapeutic parameters, such as enhanced stability and/or half life, improved binding and/or cross-reactivity, and/or reduced immunogenicity, while maintaining binding to serum albumin.

Derivatives of anti-TNF-alpha polypeptide-albumin-binding domain fusions retain antigen-binding specificity, e.g., to TNF-alpha. The anti-TNF-alpha polypeptide-albumin-binding domain fusions of the invention, along with antigen-binding fragments and derivatives thereof, find use as therapeutic agents, as described in detail below. See also Example 8 and FIGS. 5-9.

In some embodiments, additional strategies are used to enhance the half life the anti-TNF-alpha polypeptides, instead of or in addition to the use of albumin-binding domains. Such additional strategies are described in more detail below.

4. Other Anti-TNF-Alpha Polypeptides with Enhanced Half-Life

In some embodiments, the anti-TNF-alpha polypeptide of the invention, or fusion thereof, is modified to give a derivative. In particular, the present invention encompasses anti-TNF-alpha polypeptides, or albumin-binding fusions thereof, comprising one or more antibody single domains that have been modified by any method known in the art and/or described herein to increase or improve the serum half-life of the polypeptide, with or without fusion to an albumin-binding domain.

For example, but not by way of limitation, derivatives include anti-TNF-alpha polypeptides that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formylation, metabolic synthesis of tunicamycin, etc. Additionally, the derivative may contain one or more non-classical amino acids. That is, another modification to extend the serum half-life of the molecules of the invention involves the use non-natural amino acids, for example in the D form and/or the use of amino acid such as sulfur-containing forms of amino acids. In certain embodiments, reactive side chains of amino acid residues are capped, for example the carboxy side chain in glutamic acid. Capping can by accomplished using any suitable capping groups, as known in the art.

The anti-TNF-alpha polypeptides for use in accordance with the invention may contain modifications to the C- and/or N-terminus which include, but are not limited to, amidation or acetylation, and that may also improve serum half-life. Acetylation refers to the introduction of a $COCH_3$ group and can occur either at the amino terminus or on a lysine side chain(s) of a protein or fragment thereof. Importantly, acetylation can regulate protein stability. For example, analysis of in vivo acetylated E2F1 shows that the acetylated version has a longer half-life (Martínez-Balbás et al., (2000) *EMBO J.* 19(4):662-71; see also Takemura et al. (1992) *J Cell Sci.* 103 (Pt 4):953-64; each of which is hereby incorporated in its entirety). Accordingly, in certain embodiments, the amino-terminal of the anti-TNF-alpha polypeptide is modified by acetylation. In certain embodiments, a lysine side chain in the anti-TNF-alpha polypeptide is modified by acetylation. In yet other embodiments, the anti-TNF-alpha polypeptide is acetylated both at the amino terminus and on one or more lysine side chains.

As another particular example, the serum half-life of proteins can also be increased by attaching polymer molecules such as high molecular weight polyethyleneglycol (PEG). PEG can be attached to polypeptides or fragments thereof with or without a multifunctional linker and either through site-specific conjugation of the PEG to the N- or C-terminus; or via epsilon-amino groups present on lysine residues. Linear or branched polymer derivatization that results in minimal loss of biological activity can be used. The degree of conjugation can be closely monitored, e.g., by SDS-PAGE and mass spectrometry, to ensure proper conjugation of PEG molecules to the polypeptides of the invention. Unreacted PEG can be separated from polypeptide-PEG conjugates by, e.g., size exclusion or ion-exchange chromatography.

Other methods known in the art to increase serum half-life include conjugation and/or fusion to antibody domains including, but not limited to, antibody constant regions including Fc and/or hinge regions (see for example, U.S. Pat. Nos. 5,565,335, and 6,277,375); and/or conjugation and/or fusion to interferon, thymosin targeting peptides, and/or permeability increasing proteins (see, e.g., U.S. Pat. Nos. 6,319, 691 and 5,643,570).

The invention also encompasses the use of liposomes for prolonging or increasing the serum half-life of anti-TNF-alpha polypeptides of the invention. In certain embodiments, the anti-TNF-alpha polypeptides, e.g, a monomer or dimer comprising VL and/or VH domain(s), may be conjugated to liposomes using previously described methods, see, e.g., Martin et al., 1982, J. Biol. Chem. 257: 286-288, which is incorporated herein by reference in its entirety. The invention thus encompasses methods of preparing liposomes containing anti-TNF-alpha polypeptides, with or without an albumin-binding domain, with a prolonged serum half-life, i.e., enhanced circulation time. See, e.g., U.S. Pat. No. 5,013,556. In particular, sterically stabilized liposomes increase half-life e.g., by virtue of having lipid components with bulky and highly flexible hydrophilic moieties, which reduce reaction with serum proteins, reduce oposonization with serum components, and/or reduce recognition by the mononuclear phagocyte system MPS. Sterically stabilized liposomes are usually prepared using polyethylene glycol. For preparation of liposomes and sterically stabilized liposome see, e.g., Bendas et al., 2001 BioDrugs, 15(4): 215-224; Allen et al., 1987 FEBS Lett. 223: 42-6; Klibanov et al., 1990 FEBS Lett., 268: 235-7; Blum et al., 1990, Biochim. Biophys. Acta., 1029: 91-7; Torchilin. et al., 1996, J. Liposome Res. 6: 99-116; Litzinger et al., 1994, Biochim. Biophys. Acta, 1190: 99-107; Maruyama et al., 1991, Chem. Pharm. Bull., 39: 1620-2; Klibanov et al., 1991, Biochim Biophys Acta, 1062; 142-8; Allen et al., 1994, Adv. Drug Deliv. Rev, 13: 285-309; all of which are incorporated herein by reference in their entireties.

The invention also encompasses liposomes that are adapted for specific organ targeting, see, e.g., U.S. Pat. No. 4,544,545, or specific cell targeting, see, e.g., U.S. Patent Application Publication No. 2005/0074403. Particularly useful liposomes for use in the compositions and methods of the invention can be generated by reverse phase evaporation method with a lipid composition comprising phosphatidylcholine, cholesterol, and PEG derivatized phosphatidylethanolamine (PEG-PE). Liposomes are extruded through filters of defined pore size to yield liposomes with the desired diameter.

5. Anti-TNF-Alpha Polypeptide Variants with Reduced Immunogenicity

Another aspect of the invention relates to anti-TNF-alpha polypeptides having reduced immunogenicity, that is anti-TNF-alpha polypeptides in which at least one $T_H$ epitope has been eliminated and/or reduced. In some embodiments, the anti-TNF-alpha polypeptide is mutated to provide improved solubility and/or affinity, as well as (or separately from) reduced immunogenicity. A polypeptide having reduced immunogenicity is referred to as a "de-immunized" polypeptide. De-immunized anti-TNF-alpha polypeptides of the invention result in reduced immunogenicity in the intended host, e.g., in a human patient. Anti-TNF-alpha polypeptides, with or without fusion to an albumin-binding domain, can be modified, where the modification reduces immunogenicity. In some embodiments, the albumin-binding domain of the fusion may be de-immunized separately. In particular, the present invention encompasses anti-TNF-alpha polypeptides that comprise one or more antibody single domains fused to one or more albumin-binding domains, either or both of which have been modified by any method known in the art and/or described herein to reduce immunogenicity of the polypeptide construct.

De-immunization may be achieved by any process known in the art and/or described herein. In one approach, a model of the 3-D structure of the polypeptide is built. A list of substitutions then is proposed to minimize the number of $T_H$ epitopes, preferably eliminating the most important epitopes, without affecting the stability of the polypeptide or its binding affinity to a target, e.g., human TNF-alpha and/or serum albumin. Genes comprising various combinations of the suggested substitutions can be synthesized and expressed, and then solubility, affinity, and cross-reactivity can be determined. See also Example 9 and FIGS. 10-13.

Accordingly, in some embodiments, anti-TNF-alpha polypeptides, and fusions thereof with albumin-binding domains, are provided that are de-immunized. The "de-immunized" polypeptide has been mutated to reduce $T_H$ epitope content and comprises one or more substitutions that reduce immunogenicity. Generally, the polypeptide comprises one or more domains that have been de-immunized, e.g, substituted at one or more amino acid positions to reduce or eliminate epitopes that bind one or more HLA class II receptors. Substitutions may occur, e.g, in an antibody single domain, such as in a light chain variable domain; and/or in an albumin-binding domain.

In some embodiments, the de-immunized polypeptide comprises substitutions that eliminate at least 10 $T_H$ epitopes, at least 15 $T_H$ epitopes, at least 20 $T_H$ epitopes, at least 25 $T_H$ epitopes, at least 30 $T_H$ epitopes, at least 40 $T_H$ epitopes, or at least 50 $T_H$ epitopes. In preferred embodiments, the substitutions do not affect, or at least do not substantially affect, binding of the polypeptide construct to serum albumin and/or to a TNF-alpha molecule compared with the construct before de-immunization.

In particular embodiments, the anti-TNF-alpha polypeptide in accordance with the invention comprises one or more of any of the antibody single domains, dimers, derivatives, and/or albumin-binding domains described herein, wherein the antibody single domain, dimer, derivative, and/or albumin-binding domain is de-immunized. In some preferred embodiments, the anti-TNF-alpha polypeptide comprises a VL-VL heterodimer fused to an albumin-binding domain, wherein one or both VL domains, and/or the albumin-binding domain, are de-immunized. In some more preferred embodiments, the VL-VL heterodimer comprises one or both of VL18 or VL11, one or both of which are de-immunized. In particular embodiments, the heterodimer is fused to PEP, which may or may not also be de-immunized. In some even more preferred embodiments, the anti-TNF-alpha polypeptide comprises one or more of VL18, VL11, and PEP, where one or more of which is de-immunized.

In particular embodiments, the anti-TNF-alpha polypeptide comprises a light chain variable domain, said variable domain comprising an amino acid sequence corresponding to SEQ ID NO:1 (VL18) or an antigen-binding fragment or derivative thereof, which is de-immunized, e.g., by at least one amino acid substitution selected from the group consisting of T7Q, V15P, (A51V-L54R/A51V-L54E), K63S, E79K, (C80S), T91A, and L111K. The numbering refers to amino acid positions of SEQ ID NO:1. Also, values between brackets refer to germline-filtered peptides, e.g. (C80S); double mutants are linked by a hyphen, e.g. A51V-L54R; and alternate proposed substitutions involving the same position are presented within brackets, separated by a slash, e.g. (A51V-L54R/A51V-L54E).

In particular embodiments, the anti-TNF-alpha polypeptide comprises a light chain variable domain, said variable domain comprising an amino acid sequence corresponding to SEQ ID NO:2 (VL11), or an antigen-binding fragment or derivative thereof, which is de-immunized e.g., by at least one amino acid substitution selected from the group consisting of T7Q, V15P, R31S, (A51V-L54R/A51V-L54E), K63S, E79K, (C80S), T91A, A100S, and E106K (where the numbering refers to amino acid residues of SEQ ID NO:2 according to the Ordinal system).

In further specific embodiments, the anti-TNF-alpha polypeptide comprises a light chain variable domain, said variable domain comprising at least one sequence selected from the group consisting of SEQ ID NOs:19-23 (five de-immunized VL18 variants), SEQ ID NOs: 24-28 (five de-immunized VL11 variants), and a TNF-alpha-binding fragment or derivative thereof. The five de-immunized VL18 variants corresponding to SEQ ID NOs:19-23 may also be referred to herein as VL18 #1, VL18 #2, VL18 #3, VL18 #4, and VL18 #5, respectively. The five de-immunized VL11 variants corresponding to SEQ ID NOs:24-28 may also be referred to herein as VL11 #1, VL11 #2, VL11 #3, VL11 #4, and VL11 #5, respectively.

In some embodiments, the anti-TNF-alpha polypeptide-albumin-binding domain fusion of the invention comprises a TNF-alpha-binding fragment of at least one sequence selected from the group consisting of SEQ ID NOs:19-28 comprising at least 10 contiguous amino acids of said sequence. In other embodiments, the fusion comprises a TNF-alpha-binding fragment of any one of more or SEQ ID NOs:19-28 comprising at least 15 contiguous amino acids of said sequence. In other embodiments, the fusion comprises a TNF-alpha-binding fragment of any one or more SEQ ID NOs:19-28 comprising at least 20 contiguous amino acids of said sequence. In other embodiments, the fusion comprises a TNF-alpha-binding fragment of any one or more of SEQ ID NOs:19-28 comprising at least 25 contiguous amino acids of said sequence. In other embodiments, the fusion comprises a TNF-alpha-binding fragment of any one or more of SEQ ID NOs:19-28 comprising at least 30 contiguous amino acids of said sequence. In other embodiments, the fusion comprises a TNF-alpha-binding fragment of any one or more of SEQ ID NOs:19-28 comprising at least 35 contiguous amino acids of said sequence. In other embodiments, the fusion comprises a TNF-alpha-binding fragment of any one or more of SEQ ID NOs:19-28 comprising at least 40 contiguous amino acids of said sequence.

In some embodiments, the anti-TNF-alpha polypeptide-albumin-binding domain fusion of the invention comprises an amino acid sequence corresponding to a derivative of any one or more of SEQ ID NOs:19-28. In some embodiments, the fusion has at least 45%, at least 50%, at least 55%, at least 60%, at least 65%, at least 70%, at least 75%, at least 80%, at least 85%, at least 90%, at least 95%, at least 98%, or at least 99% sequence identity to any one or more of SEQ ID NOs: 19-28.

In certain embodiments, the invention encompasses an anti-TNF-alpha polypeptide-albumin-binding domain fusion that comprises 1, 2, 3, 4, 5, 6, 7, 8, 9, 10, or more amino acid modifications (e.g., insertion, substitution, deletion, etc.) relative to any one or more of SEQ ID NOs:19-28. Amino acid sequence derivatives of the polypeptides of the invention can be created such that they are substitutional, insertional or deletion derivatives, as described above.

In particular embodiments, the anti-TNF-alpha polypeptide comprises an albumin-binding domain, said albumin-binding domain comprising an amino acid sequence corresponding to SEQ ID NO:30 (PEP), or an albumin-binding fragment or derivative thereof, which is de-immunized e.g., by at least one amino acid substitution selected from the group consisting of E12D, T29H-K35D, and A45D (where the numbering refers to amino acid residues of SEQ ID NO:30 according to the Ordinal system). In more particularly preferred embodiments, PEP is de-immunized to comprise an amino acid sequence corresponding to SEQ ID NO:31. SEQ ID NO:31 refers to a particular de-immunized PEP variant, that also is referred to herein as "PEP DI."

In further particular embodiments, the anti-TNF-alpha polypeptide comprises a dimer, said dimer comprising an amino acid sequence corresponding to SEQ ID NO:32 (VL18-3L-VL11), or SEQ ID NO:33 (VL18-3L-VL11-PEP), or an antigen-binding fragment or derivative thereof, which is de-immunized. For example, in specific embodiments, the polypeptide of the invention comprises at least one amino acid sequence selected from the group consisting of SEQ ID NOs: 34-44 (eleven VL18-3L-VL11/PEP variants), or a TNF-alpha-binding fragment or derivative thereof.

In some embodiments, the agent of the invention comprises or consists of an amino acid sequence selected from the group consisting of SEQ ID NOs: 34-44. These sequences correspond to eleven VL18-3L-VL11/PEP variants, which have been de-immunized. SEQ ID NO:34 refers to a VL18-3L-VL11-PEP construct where PEP is de-immunized, as described herein, and also is referred to herein as "VL18-3L-VL11-PEP DI". SEQ ID NOs:35-39 refer to de-immunized VL18-3L-VL11 constructs, which also may be referred to herein as VL18-3L-VL11 DI #1, VL18-3L-VL11 DI #2, VL18-3L-VL11 DI #3, VL18-3L-VL11 DI #4, and VL18-3L-VL11 DI #5, respectively. SEQ ID NOs:40-44 refer to de-immunized VL18-3L-VL11-PEP constructs, which also may be referred to herein as VL18-3L-VL11 DI #1-PEP DI, VL18-3L-VL11 DI #2-PEP DI, VL18-3L-VL11 DI #3-PEP DI, VL18-3L-VL11 DI #4-PEP DI, and VL18-3L-VL11 DI #5-PEP DI, respectively.

Anti-TNF-alpha polypeptides of the invention, including fusions and/or de-immunized variants thereof, can be made by any technique known in the art or described herein, as detailed below.

6. Methods of Making Anti-TNF-Alpha Polypeptides, Variants and Fusions Thereof Another aspect of the present invention involves making the anti-TNF-alpha polypeptides of the invention, antigen-binding fragments or derivatives thereof, as well as making anti-TNF-alpha polypeptides that are de-immunized and/or that are linked to albumin-binding domains. In some embodiments, an anti-TNF-alpha polypeptide according to the invention is produced by recombinant DNA techniques, or other protein synthetic techniques, e.g., by use of a peptide synthesizer.

In some embodiments, the anti-TNF-alpha polypeptide, or albumin-binding domain fusion (or conjugate) thereof, includes more than one antibody single domains that are linked, e.g., to form a dimer, trimer, tetramer, etc., such as VL-VL dimers in accordance with certain aspects of the invention. Methods for producing dimeric polypeptides, as well as higher order polypeptide constructs, are known in the art. For example, a nucleic acid encoding a first antibody single domain can be cloned into an expression vector containing a second antibody single domain, such that the two domains are linked in-frame, with or without and intervening linker. See e.g., Morrison, 1985, *Science* 229:1202; Oi et al., 1986, *BioTechniques* 4:214; Gillies et al., 1989, *J. Immunol. Methods* 125:191-202; and U.S. Pat. Nos. 6,311,415; 5,807,715; 4,816,567; and 4,816,397, which are incorporated herein by reference in their entirety. The first and second antibody single domains may be the same or different, as described above, producing, e.g., VL-VL, VH-VH, VH-VL, or VL-VH homo- or hetero-dimeric constructs. In preferred embodiments, each of the single domains (VH or VL) is directed to a TNF-alpha molecule, such as human TNF-alpha, with possible cross-reactivity to a non-human TNF-alpha, such as that of a small non-primate mammal, or to both at least one rodent and at least one non-rodent species, as described herein.

In some embodiments, the anti-TNF-alpha polypeptide according to the invention is fused to an albumin-binding domain. Fusion proteins also can be produced by standard recombinant DNA techniques or by protein synthetic techniques, e.g., by use of a peptide synthesizer, or by PCR amplification. In addition to recombinant fusion, linkage to an albumin-binding domain may involve, e.g., chemical conjugation, including both covalent and non-covalent conjugations.

Linkage does not necessarily need to be direct, but may occur through linker sequences or through chemical conjugation. Protein linkers between albumin-binding domains and the anti-TNF-alpha polypeptides of interest can be selected in order to maintain flexibility and proper folding, preferably such that the linked product shows binding to albumin, as well as to a TNF-alpha molecule. A linker can be selected, e.g, that allows good simultaneous binding to both TNF-alpha and serum albumin. Such binding can be assayed by techniques known to those of skill in the art.

Polynucleotides of the invention also encompass vectors, such as vectors for the expression of the anti-TNF-alpha polypeptides of the invention. Expression vectors containing the coding sequences of polypeptides in accordance with the invention, along with appropriate transcriptional and translational control signals, can be constructed using methods well known to those skilled in the art. These methods include, for example, in vitro recombinant DNA techniques, synthetic techniques, and in vivo genetic recombination. (See, for example, the techniques described in Sambrook et al., 1990, Molecular Cloning, A Laboratory Manual, 2d Ed., Cold Spring Harbor Laboratory, Cold Spring Harbor, N.Y. and Ausubel et al. eds., 1998, Current Protocols in Molecular Biology, John Wiley & Sons, NY). See also Example 10 and Tables 2-4 below.

An expression vector comprising the nucleotide sequence of an anti-TNF-alpha polypeptides of the invention, e.g., a fusion protein with an albumin-binding domain, can be transferred to a host cell by conventional techniques (e.g., electroporation, liposomal transfection, and calcium phosphate precipitation) and the transfected cells then can be cultured by conventional techniques to produce a polypeptide of the invention.

In a specific embodiment, the expression of an anti-TNF-alpha polypeptide or fusion thereof is regulated by a constitutive promoter. In another embodiment, expression is regulated by an inducible promoter. In accordance with these embodiments, the promoter may be a tissue-specific promoter.

In a specific embodiment, a vector is used that comprises a promoter operably linked to a protein-encoding nucleic acid, one or more origins of replication, and, optionally, one or more selectable markers (e.g., an antibiotic resistance gene). A variety of host-expression vector systems may be utilized to express the anti-TNF-alpha polypeptides of the invention, and/or fusions thereof with albumin-binding domains. The host cells used to express the recombinant anti-TNF-alpha polypeptides or fusions thereof may be, e.g., either bacterial cells such as *Escherichia coli*, or eukaryotic cells. Examples of suitable bacterial cells include the bacteria *E. coli* or *B. subtilis*, transformed with recombinant bacteriophage DNA, plasmid DNA, or cosmid DNA expression vectors.

In a particular embodiment, *E. coli* Tuner™ (DE3) cells are used for large-scale expression of anti-TNF-alpha polypeptides of the invention. "Tuner™ strains" are lacZY deletion mutants of *E. coli* BL21 that facilitate controlled adjustment of the level of protein expression in cell culture. Expression levels are controlled by the lac permease (lacY) mutation, which allows uniform entry of IPTG into cells in a population, producing a concentration-dependent, homogeneous induction in response to varying IPTG concentration. "DE3" indicates that the host is a lysogen of λDE3, carrying a chromosomal copy of the T7 RNA polymerase gene under control of the lacUV5 promoter. See also Example 11 below, and Tables 5-6.

The expression levels of an anti-TNF-alpha polypeptide of the invention, or fusion thereof, can be increased, e.g., by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing a polypeptide described herein is amplifiable, changes in the culture medium can increase the number of copies of the marker gene. Since the amplified region can be associated with the nucleotide sequence encoding an anti-TNF-alpha polypeptide of the invention, production of the polypeptide also can increase (Crouse et al., 1983, *Mol. Cell. Biol.* 3:257).

For long-term, high-yield production of recombinant proteins, stable expression is preferred. For example, cell lines which stably express an anti-TNF-alpha polypeptide of the invention may be engineered. Rather than using expression vectors which contain viral origins of replication, host cells can be transformed with DNA controlled by appropriate expression control elements (e.g., promoter, enhancer sequences, transcription terminators, polyadenylation sites, etc.) and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci, which in turn can be cloned and expanded into cell lines. This method may advantageously be used to engineer cell lines which express an anti-TNF-alpha polypeptides of the invention for long-term, high-yield production. Such engineered cell lines also may be particularly useful in screening and evaluation of compounds that interact directly or indirectly with anti-TNF-alpha polypeptides and/or fusions thereof.

Once an anti-TNF-alpha polypeptide of the invention has been recombinantly expressed, it may be purified by any method known in the art for purification of an agent, for example, by chromatography (e.g., ion exchange, affinity, particularly by affinity for the specific antigen after Protein A, and sizing column chromatography), centrifugation, differential solubility, or by any other standard technique for the purification of proteins. Polypeptides of the invention can be fused to marker sequences, such as a peptide, to facilitate purification. In some embodiments, the marker amino acid sequence is a hexahistidine peptide (SEQ ID NO: 60), such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA, 86:821 824, 1989 (hereby incorporated by reference in its entirety), for instance, a hexahistidine tag (SEQ ID NO: 60) provides for convenient purification of the anti-TNF-alpha polypeptide or fusion thereof. Other peptide tags useful for purification include, but are not limited to, the hemagglutinin "HA" tag, which corresponds to an epitope derived from the influenza hemagglutinin protein (Wilson et al., Cell, 37:767 1984, hereby incorporated by reference in its entirety) and the "flag" tag (Knappik et al., *Biotechniques*, 17(4):754 761, 1994), each of which are hereby incorporated by reference in its entirety. Another technique involves nickel affinity chromatography for endotoxin removal, following expression in *E. coli*. Another technique involves Protein L and/or human albumin affinity chromatography. See also Example 12.

De-immunized anti-TNF-alpha polypeptides may be generated using techniques to reduce or eliminate one or more $T_H$ epitotes in the polypeptide, as described in detail above. Substitutions at the amino acid level inform the construction of the corresponding nucleic acids encoding same, as described in more detail below.

7. Polynucleotides Encoding the Polypeptides of the Invention

The invention provides polynucleotides comprising a nucleotide sequence encoding a polypeptide of the invention, such as an anti-TNF-alpha polypeptide comprising one or more antibody single domains, as well as fusions thereof to an albumin-binding domain, or a fragment or derivative thereof. In specific embodiments, the polynucleotide of the invention comprises or consists of a nucleic acid encoding a polypeptide disclosed herein, such as one or more of SEQ ID NOs: 1-44. The invention also encompasses polynucleotides that hybridize under high stringency, intermediate or lower stringency hybridization conditions, to polynucleotides that encode a polypeptide of the invention.

The polynucleotides may be obtained, and the nucleotide sequence of the polynucleotides determined, by any method known in the art. For example, a polynucleotide encoding a polypeptide of the invention may be generated from nucleic acid from a suitable source (e.g., a TNF-alpha immunized rabbit). If a source containing a nucleic acid encoding a particular polypeptide is not available, but the amino acid sequence of the polypeptide of the invention is known, a nucleic acid encoding the polypeptide may be chemically synthesized and cloned into replicable cloning vectors using methods well known in the art.

Once the nucleotide sequence of the polynucleotide of the invention is determined, the nucleotide sequence may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are incorporated by reference herein in their entireties), to generate polypeptides having a different amino acid sequence, for example to create amino acid substitutions, deletions, and/or insertions. As described above, such mutated sequences can provide polypeptides of the invention with enhanced pharmaceutical properties, e.g., improved serum half-life and/or reduced immunogenicity.

Polynucleotides encoding fusion products may be obtained by recombinant techniques, as are well known and routinely practiced in the art. Such polynucleotides may be referred to as "chimeric polynucleotides." Recombinant chimeric polynucleotides typically are created by joining two or more genes, or portions thereof, which originally coded for separate proteins. The individual sequences typically correspond to coding sequences for a functional domain of each of the respective proteins, such that the fusion polypeptide encodes a fusion protein having dual functionality (e.g., binding to serum albumin and to TNF-alpha). For example, a first coding sequence, or portion thereof, may be joined in frame to a second coding sequence, or portion thereof, which typically is achieved through ligation or overlap extension PCR. Ligation is used with the conventional method of creating chimeric genes, called the "cassette mutagenesis method." In this method, DNA can be cut into specific fragments by restriction endonucleases acting at restriction endonuclease recognition sites, and the specific fragments can be then ligated. A particular fragment can be substituted with a heterologous one having compatible ends in order to ligate it into the parental DNA. See, e.g., Wells et al., Gene 34:315-23 (1985), hereby incorporated by reference in its entirety.

Alternatively, various approaches involving PCR may be used, such as the overlap extension PCR method. See, e.g., Ho, S, N., et al (1989). Site-directed mutagenesis by overlap extension using the polymerase chain reaction. Gene. 77: 51-59, hereby incorporated by reference in its entirely. Several variations of this PCR approach are known and have been used to generate fusion products. One such approach, for example, involves modified overlap extension PCR to create chimeric genes in the absence of restriction enzymes in three steps: (i) a conventional PCR step, using primers partially complementary at their 5' ends to the adjacent fragments that are to be fused to create the chimeric molecule; (ii) a second PCR step where the PCR fragments generated in the first step are fused using the complementary extremities of the primers; and (iii) a third step involving PCR amplification of the fusion product. The final PCR product is a chimeric gene built up with the different amplified PCR fragments. See, e.g., Wurch, T. et al (1998) A modified overlap extension PCR method to create chimeric genes in the absence of restriction enzymes. Biotechnology Techniques. 12(9):653-657, hereby incorporated by reference in its entirety. Any ligation and/or PCR-based recombinant approaches may be used to create the chimeric polynucleotides of the present invention.

Alternatively a nucleic acid encoding the fusion product may be chemically synthesized. For example, using the desired amino acid sequence of a fusion polypeptide of the invention, the corresponding nucleotide sequence may be devised, chemically synthesized, and cloned into replicable cloning vectors using, e.g., well known methods in the art.

The invention further provides a vector comprising at least one polynucleotide encoding a polypeptide of the invention. In some embodiments, the vector is an expression vector. The invention further provides host cells comprising one or more vectors of the invention. The vectors, expression vectors, and host cells can include any of those discussed above.

8. Methods of Use

Another aspect of the present invention relates to therapies which involve administering an anti-TNF-alpha polypeptide (or nucleic acid) according to the invention to a host for delaying, preventing, treating, or ameliorating symptoms associated with a TNF-alpha-related condition. A "TNF-alpha-related condition" as used herein refers to any disorder, disease, or infection in which TNF-alpha plays a role, e.g., a condition mediated by and/or associated with the binding of TNF-alpha to a cognate receptor (a TNF-alpha receptor), or where TNF-alpha is otherwise implicated in the development, progression, or symptoms of the condition. TNF-alpha-related conditions include, but are not limited to, inflammatory disorders, including systemic inflammation and localized inflammation. Inflammatory disorders include, but are not limited to, rheumatoid arthritis, psoriatic arthritis, Crohn's disease, ulcerative colitis, inflammatory bowel syndrome, multiple sclerosis, spondyloarthropathies, asthma, macular degeneration, and the like.

Inflammation can be acute or chronic. Acute inflammation is the initial response of the body to harmful stimuli, achieved, e.g., by the increased movement of plasma and leukocytes (especially granulocytes) from the blood to the injured tissue. A cascade of biochemical events propagates and matures the inflammatory response, involving the vascular system, the immune system, and various cells within the injured tissue. Chronic or prolonged inflammation, leads to a progressive shift in the type of cells present at the site of inflammation and can lead to destruction of the tissue from the inflammatory process itself. Chronic inflammation can also lead to a host of related conditions, including hay fever, atherosclerosis, rheumatoid arthritis, and even cancer (e.g., gallbladder carcinoma). Inflammation is normally closely regulated by the body, whereas faulty regulation can lead to a TNF-alpha-related condition, as defined herein. In a particularly preferred embodiment, the present invention is directed to the treatment of a human subject, e.g., by administering an anti-TNF-alpha polypeptide (or nucleic acid encompassing same) according to the instant disclosure, to a human subject in need thereof.

The invention provides methods of treatment, prophylaxis, and amelioration of one or more symptoms associated with a TNF-alpha related condition by administering to a subject an effective amount of a polypeptide comprising at least one antibody single domain specific for TNF-alpha, with or without fusion to an albumin-binding domain, or a nucleic acid encoding same; or by administering a pharmaceutical composition comprising at least one of the polypeptides or nucleic acids of the invention. The pharmaceutical compositions, polynucleotides, and nucleic acids of the invention function as therapeutic and/or prophylactic agents against a TNF-alpha-related condition.

In some embodiments, the anti-TNF-alpha agent for use as described herein is a polypeptide comprising or consisting of one of more of SEQ ID NO:1 (VL18); SEQ ID NO:1 (VL18) further comprising at least one amino acid substitution selected from the group consisting of T7Q, V15P, (A51V-L54R/A51V-L54E), K63S, E79K, (C80S), T91A, and L111K (where the numbering refers to amino acid positions of SEQ ID NO:2 according to the Ordinal system); SEQ ID NO:2 (VL11); SEQ ID NO:2 (VL11) further comprising at least one amino acid substitution selected from the group consisting of T7Q, V15P, R31S, (A51V-L54R/A51V-L54E), K63S, E79K, (C80S), T91A, A100S, and E106K (where the numbering refers to amino acid residues of SEQ ID NO:2 according to the Ordinal system); SEQ ID NOs:3-18 (16 rabbit VLs); SEQ ID NOs:19-23 (five VL18 variants); SEQ ID NOs:24-28 (five VL11 variants); SEQ ID NO:32 (VL18-3L-VL11); SEQ ID NO:33 (VL18-3L-VL11-PEP); and SEQ ID NOs:34-44 (11 VL18-3L-VL11/PEP variants). In some embodiments, the anti-TNF-alpha agent is a polypeptide comprising one or more of SEQ ID NO:29 (3L); SEQ ID NO:30 (PEP); SEQ ID NO:30 (PEP) further comprising at least one amino acid substitution selected from the group consisting of E12D, T29H-K35D, and A45D (where the numbering refers to amino acid residues of SEQ ID NO:30 according to the Ordinal system); and/or SEQ ID NO:31 (de-immunized PEP). In some embodiments, the anti-TNF-alpha agent is one or more of said polypeptides, one or more nucleic acids encoding one or more of said polypeptides, a pharmaceutical composition comprising one or more of the above-recited amino acid sequences and/or nucleic acid sequences, or any combination thereof.

In particular embodiments, one or more anti-TNF-alpha polypeptides comprising at least one antibody single domain specific for TNF-alpha, or antigen-binding fragment or derivative thereof, according to the present invention, can function as prophylactic and/or therapeutic agents against a TNF-alpha-related condition. Without wishing to be bound by theory, anti-TNF-alpha polypeptides of the invention may bind to TNF-alpha so as to antagonize the action of TNF-alpha with its receptor(s). This may have the effect of blocking the action of excessive TNF-alpha in a condition where TNF-alpha is a causative agent, such as rheumatoid arthritis.

Accordingly, an anti-TNF-alpha polypeptide of the invention can be administered to a host, particularly to a human, to treat, delay, prevent, or ameliorate one or more symptoms associated with a TNF-alpha-related condition. In some embodiments, the anti-TNF-alpha polypeptide is linked to at least one albumin-binding domain, e.g., PEP, other albumin-binding domain, or albumin-binding fragment or derivative thereof, as described above, to form a fusion product. As well as protein-based therapies, prophylactic and therapeutic agents of the invention include, but are not limited to, nucleic acids encoding anti-TNF-alpha polypeptides and/or fusions thereof. The agents may be provided as pharmaceutically acceptable compositions as known in the art and/or as described herein. Also, an anti-TNF-alpha polypeptide of the invention may be administered alone or in combination with other prophylactic and/or therapeutic agents.

As used herein, the terms "therapeutic agent" refers to any agent which can be used in treating or amelioring symptoms associated with a TNF-alpha-related condition. As used herein, a "therapeutically effective amount" refers to the amount of agent, (e.g., an amount of an anti-TNF-alpha polypeptide of the invention) that provides at least one therapeutic benefit in the treatment or management of a TNF-alpha-related condition, when administered to a subject suffering therefrom. Further, a therapeutically effective amount with respect to an agent of the invention means that amount of agent alone, or when in combination with other therapies, that provides at least one therapeutic benefit in the treatment or management of the condition.

As used herein, the term "prophylactic agent" refers to any agent which can be used in the prevention, delay, or slowing down of the progression of a TNF-alpha related condition. A "prophylactically effective amount" refers to the amount of the prophylactic agent (e.g., an amount of an anti-TNF-alpha polypeptide) that provides at least one prophylactic benefit in the prevention or delay of a TNF-alpha related condition, when administered to a subject predisposed thereto. A prophylactically effective amount also may refer to the amount of agent sufficient to prevent or delay the occurrence of the condition; or slow the progression of the condition; the amount sufficient to delay or minimize the onset of the condition; or the amount sufficient to prevent or delay the recurrence or spread thereof. A prophylactically effective amount also may refer to the amount of agent sufficient to prevent or delay the exacerbation of symptoms of a TNF-alpha related condition. Further, a prophylactically effective amount with respect to a prophylactic agent of the invention means that amount of prophylactic agent alone, or when in combination with other agents, that provides at least one prophylactic benefit in the prevention or delay of the condition.

A prophylactic agent of the invention can be administered to a subject "pre-disposed" to a TNF-alpha-related condition. A subject that is "pre-disposed" to a TNF-alpha related condition is one that shows symptoms associated with the development of the condition, or that has a genetic makeup, environmental exposure, or other risk factor for such a condition, but where the symptoms are not yet at the level to be diagnosed as the condition. For example, a patient with a family history of rheumatoid arthritis may qualify as one predisposed thereto.

The dosage amounts and frequencies of administration provided herein are encompassed by the terms therapeutically effective and prophylactically effective. The dosage and frequency will typically vary according to factors specific for each patient depending on the specific therapeutic or prophylactic agents administered, the severity and type of disease, the route of administration, as well as age, body weight, response, and the past medical history of the patient, and should be decided according to the judgment of the practitioner and each patient's circumstances. Suitable regimens can be selected by one skilled in the art by considering such factors and by following, for example, dosages reported in the literature and recommended in the Physician's Desk Reference (56$^{th}$ ed., 2002). Prophylactic and/or therapeutic agents can be administered repeatedly. Several aspects of the procedure may vary such as the temporal regimen of administering the prophylactic or therapeutic agents, and whether such agents are administered separately or as an admixture.

The amount of an agent of the invention that will be effective can be determined by standard clinical techniques. Effective doses may be extrapolated from dose-response curves derived from in vitro or animal model test systems. For any agent used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

Prophylactic and/or therapeutic agents, as well as combinations thereof, can be tested in suitable animal model systems prior to use in humans. Such animal model systems include, but are not limited to, rats, mice, chicken, cows, monkeys, pigs, dogs, rabbits, etc. Any animal system well-known in the art may be used. Such model systems are widely used and well known to the skilled artisan. In some preferred embodiments, animal model systems for a TNF-alpha related condition are used that are based on rats, mice, or other small mammal other than a primate. For example, in a specific embodiment, putative prophylactic and/or therapeutic anti-TNF-alpha polypeptides of the invention are tested in a mouse or rat model system, such as, e.g., the established rat-adjuvant-induced arthritis (AIA) model or the collagen-induced arthritis (CIA) model. The AIA model is a much more aggressive model of arthritis compared to the CIA model. Testing in such systems, rather than primate-based model systems, afford the advantage of reduced costs in in vivo and/or pre-clinical testing. Without wishing to be bound by theory, testing in animals other than primates is feasible where anti-TNF-alpha antibody molecules are selected based on cross-reactivity with rat and/or mouse TNF-alpha, or with TNF-alpha of another non-primate, small mammal. Such antibodies provide anti-TNF-alpha polypeptides suitable for use in the invention, where therapeutic effect can be achieved in human patients, while in vivo testing, e.g., testing for low toxicity, can be conducted in rat and/or mice models. See also Example 13a and FIG. 16.

Another animal model involves the transgenic mouse (Tg197) model. The Tg197 model of arthritis is a humanized TNF transgenic mouse model with human TNF-alpha deregulated expression resulting in the spontaneous development of arthritis pathology closely resembling that of the human rheumatoid arthritis (Keffer et al. 1991 "Transgenic mice expressing human tumor necrosis factor: a predictive genetic model of arthritis" The *EMBO Journal* 10(13): 4025-4031, the contents of which are hereby incorporated by reference in entirety). The Tg197 mouse develops chronic polyarthritis with 100% incidence at 4-7 weeks of age and provides a fast in vivo model for assessing human therapeutics for the treatment of rheumatoid arthritis. This model was successfully used in establishing the therapeutic efficacy of Remicade™ and is currently widely used for efficacy studies testing bio-similars or novel anti-human TNF-alpha therapeutics. See also Example 13b and Examples 14-19, and Tables 7-12.

Once the prophylactic and/or therapeutic agents of the invention have been tested in an animal model, they can be tested in clinical trials to establish their efficacy. Establishing clinical trials will be done in accordance with common methodologies known to one skilled in the art, and the optimal dosages and routes of administration as well as toxicity profiles of agents of the invention can be established. For example, a clinical trial can be designed to test an anti-TNF-alpha polypeptide of the invention for efficacy and toxicity against rheumatoid arthritis in human patients. See Example 20 below.

In some embodiments, an anti-TNF-alpha polypeptide is administered in a total dose of about 0.1 ng to about 1 g to treat a TNF-alpha-related condition, in a human patient, such as rheumatoid arthritis. In more particular embodiments, anti-TNF-alpha polypeptide is administered in a total dose of about 0.1 µg to about 1 mg; about 1 µg to about 500 µg; about 10 µg to about 400 µg; or about 50 µg to about 200 µg.

Toxicity and efficacy of the prophylactic and/or therapeutic agents of the instant invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Prophylactic and/or therapeutic agents that exhibit large therapeutic indices are preferred. While prophylactic and/or therapeutic agents that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of the prophylactic and/or therapeutic agents for use in humans. The dosage of such agents lies preferably within a range of circulating concentrations that include the $ED_{50}$ with little or no toxicity. The dosage may vary within this range depending upon the dosage form employed and the route of administration utilized.

Therapeutic or prophylactic agents of the present invention that function as antagonists of a TNF-alpha related condition can be administered to a host to treat, delay prevent, or ameliorate one or more symptoms associated with the condition. Anti-TNF-alpha agents of the invention, e.g., polypeptides comprising an antibody single domain fused to an albumin-binding domain, can be used to reduce the inflammation experienced by animals, particularly mammals, more particularly humans with inflammatory symptoms and/or disorders.

In specific embodiments, a therapeutic or prophylactic agent comprising an anti-TNF-alpha polypeptide of the invention, antigen-binding fragment derivative, or fusion thereof, can be administered to treat, delay, prevent, or ameliorate one or more symptoms associated with an inflammatory condition. In a specific embodiment, a polypeptide in accordance with the invention reduces the inflammation in an animal by at least 99%, at least 95%, at least 90%, at least 85%, at least 80%, at least 75%, at least 70%, at least 60%, at least 50%, at least 45% at least 40%, at least 35%, at least 30%, at least 25%, at least 20%, or at least 10% relative to the inflammation in an animal not administered the agent. In another embodiment, a therapeutic or prophylactic agent comprising a combination of anti-TNF-alpha polypeptides, antigen-binding fragments derivatives, or fusions thereof, reduce the inflammation in an animal by at least 99%, at least 95%, at least 90%, at least 85%, at least 80%, at least 75%, at least 70%, at least 60%, at least 50%, at least 45%, at least 40%, at least 35%, at least 30%, at least 25%, at least 20%, or at least 10% relative to the inflammation in an animal in not administered the combination.

In specific embodiments, a therapeutic or prophylactic agent comprising an anti-TNF-alpha polypeptide of the invention, antigen-binding fragment derivative, or fusion thereof, can be administered to treat, delay, prevent, or ameliorate one or more symptoms associated with rheumatoid arthritis. Rheumatoid arthritis is characterized by inflammatory responses in the synovial joints (synovitis), leading to destruction of cartilage and ankylosis of the joints. Synovitis involves inflammation of the synovial membranes lining joints and tendon sheaths. The affected joints become swollen, tender, and stiff. Other characteristic symptoms of RA include rheumatoid nodules, which can be a few millimeters to a few centimeters in diameter, often subcutaneous, and generally found over bony prominences; as well as vasculitis, which leads to a purplish discoloration of the skin. Lungs, kidneys, heart and blood vessels may also be affected. For example, fibrosis of the lungs and pleural effusions are associated with rheumatoid arthritis; and renal amyloidosis can occur due to chronic inflammation. Also, rheumatoid arthritis patients are more prone to artheroscleorsis, myocardial infarction, and stroke.

In preferred embodiments, a polypeptide in accordance with the invention reduces inflammation in a synovial joint in an animal by at least 99%, at least 95%, at least 90%, at least 85%, at least 80%, at least 75%, at least 70%, at least 60%, at least 50%, at least 45% at least 40%, at least 35%, at least 30%, at least 25%, at least 20%, or at least 10% relative to the inflammation in a synovial joint in an animal not administered the agent. In particularly preferred embodiments, reduction in inflammation leads to reduced swelling, tenderness, and/or stiffness in the affected joint. In some preferred embodiments, a polypeptide in accordance with the invention reduces rheumatoid nodules in an animal, e.g., in terms of their frequency over body prominences and/or their size. In some preferred embodiments, a polypeptide in accordance with the invention reduces vasculitis, e.g, reducing the extent and/or degree of discoloration of vasculitis over the skin.

Clinical diagnosis of rheumatoid arthritis is made on the basis of a number of criteria. Criteria include two or more swollen joints, morning stiffness lasting more than one hour for at least six weeks, detection of rheumatoid factor (a non-specific antibody) or anti-citrullinated protein antibodies (ACPAs). In some embodiments, a polypeptide in accordance with the invention reduces one or more of these criteria. For example, in some preferred embodiments, a polypeptide in accordance with the invention reduces the level of rheumatoid factor in the blood of an animal by at least 99%, at least 95%, at least 90%, at least 85%, at least 80%, at least 75%, at least 70%, at least 60%, at least 50%, at least 45% at least 40%, at least 35%, at least 30%, at least 25%, at least 20%, or at least 10% relative to the level of rheumatoid factor in an animal not administered the agent. In some preferred embodiments, a polypeptide in accordance with the invention reduces the level of ACPAs in the blood of an animal by at least 99%, at least 95%, at least 90%, at least 85%, at least 80%, at least 75%, at least 70%, at least 60%, at least 50%, at least 45% at least 40%, at least 35%, at least 30%, at least 25%, at least 20%, or at least 10% relative to the level of ACPAs in an animal not administered the agent. Assays for rheumatoid factor and ACPAs are known in the art, e.g., a serological point-of-care test for early detection of rheumatoid arthritis has been developed, which combines the detection of rheumatoid factor and ACPAs. See, e.g., Luime J J, et al. (2009) *Ann Rheum Dis.* 69 (2): 337-44.

The progression of rheumatoid arthritis can be followed using scores, such as the Disease Activity Score of 28 joints (DAS28). From this, the severity of the rheumatoid arthritis can be classified based on disease activity and improvement, if any. In some embodiments, a polypeptide in accordance with the invention results in a lower DAS28. For example, in some preferred embodiments, a polypeptide in accordance with the invention reduces DAS28 score of an animal by at least 99%, at least 95%, at least 90%, at least 85%, at least 80%, at least 75%, at least 70%, at least 60%, at least 50%, at least 45% at least 40%, at least 35%, at least 30%, at least 25%, at least 20%, or at least 10% relative to the DAS28 score of an animal not administered the agent.

An outcome measure in rheumatotoid arthritis clinical studies, in particular, involves ACR Criteria or American College of Rheumatology Criteria. The criteria is referred to in nearly all published studies of clinical trials for rheumatoid arthritis assessing efficacy, e.g., comparing the effectiveness of various arthritis medications or arthritis treatments, or comparing one trial to another trial. The ACR criteria is indicated as ACR 20, ACR 50, and ACR 70. ACR criteria measures improvement in tender or swollen joint counts and improvement in three of the following five parameters: (1) acute phase reactant (such as sedimentation rate); (2) patient assessment; (3) physician assessment; (4) pain scale; and (5) disability/functional questionnaire. Clinical trials report the percentage of study participants who achieve ACR 20, ACR 50, and ACR 70. For example, if a study reported that 60% of patients achieved ACR 20, that means 60% of patients in the study achieved a 20% improvement in tender or swollen joint counts as well as 20% improvement in three of the other five criteria. As another example, if a clinical trial reports that 45% of patients achieved ACR 50, that means 45% of patients in the study achieved a 50% improvement in tender or swollen joint counts as well as 50% improvement in three of the other five criteria. In some embodiments, a polypeptide of the invention in accordance with the invention results in improved ACR criteria. For example, in some preferred embodiments, a polypeptide in accordance with the invention increases the % of patients achieving ACR 20, ACR 50, or ACR 70 by at least 99%, at least 95%, at least 90%, at least 85%, at least 80%, at least 75%, at least 70%, at least 60%, at least 50%, at least 45% at least 40%, at least 35%, at least 30%, at least 25%, at least 20%, or at least 10% relative to the % of patients achieving ACR 20, ACR 50, or ACR 70, without having been administered the agent.

Prophylactic treatment of rheumatoid arthritis may delay, prevent, or slow the disease, including preventing, delaying, or slowing down one or more characteristic symptoms, diagnostic criteria, and/or disease activity score. In some embodiments, administering a polypeptide of the invention to an animal predisposed to rheumatoid arthritis delays, prevents, and/or slows the development of one or more characteristic symptoms, diagnostic criteria, and/or disease activity score compared to an animal not administered the agent. For example, in some preferred embodiments, a polypeptide in accordance with the invention delays, prevents, and/or slows synovitis, the destruction of cartilage, and/or ankylosis of the joints. In some preferred embodiments, a polypeptide in accordance with the invention delays, prevents, and/or slows swelling, tenderness, and/or stiffness of the joints. In some preferred embodiments, a polypeptide in accordance with the invention delays, prevents, and/or slows rheumatoid nodules and/or vasculitis. In some preferred embodiments, a polypeptide in accordance with the invention delays, prevents, and/or slows the appearance of rheumatoid factor and/or ACPAs in the blood.

Treatment of a subject with a therapeutically or prophylactically effective amount of the agents of the invention can include a single treatment or can include a series of treatments. For example, pharmaceutical compositions comprising an agent of the invention may be administered once a day, twice a day, or three times a day. In some embodiments, the agent may be administered once a day, every other day, once a week, twice a week, once every two weeks, once a month, once every six weeks, once every two months, twice a year, or once per year. It will also be appreciated that the effective dosage of certain agents, e.g., the effective dosage of agents comprising an antibody single domain, or antigen-binding fragment derivative, or fusion thereof, may increase or decrease over the course of treatment.

In some embodiments, ongoing treatment is indicated, e.g., on a long-term basis, such as in the ongoing treatment and/or management of chronic inflammatory disorders, such as rheumatoid arthritis. For example, in particular embodiments, an agent of the invention is administered over a period of time, e.g., for at least 6 months, at least one year, at least two years, at least five years, at least ten years, at least fifteen years, at least twenty years, or for the rest of the lifetime of a subject in need thereof.

In some embodiments, the anti-TNF-alpha polypeptide of the invention comprises one or more substitutions that reduce the immunogenicity of the polypeptide. In some embodiments, the anti-TNF-alpha polypeptide of the invention comprises an albumin-binding domain that extends the half life of the polypeptide, such that frequency of administration is reduced. For example, certain embodiments provide an anti-TNF-alpha polypeptide with an in vivo half life of about 35 to about 42 hours. In some embodiments, the anti-TNF-alpha polypeptide comprising at least one antibody single domain fused to at least one albumin-binding domain is administered no more than twice a week, no more than once a week, no more than once every two weeks, no more than once a month, no more than once every six weeks, no more than once every two months, no more than twice a year, or no more than once per year. In a specific embodiment, a therapeutic agent comprising an anti-TNF-alpha polypeptide of the invention is administered only once a month, e.g., to treat rheumatoid arthritis.

Therapeutic or prophylactic agents of this invention may also be advantageously utilized in combination with one or more other drugs used to treat the particular TNF-alpha related condition such as, for example, anti-inflammatory agents. Accordingly, a therapeutic or prophylactic agent of the invention can be administered in combination with one or more other prophylactic and/or therapeutic agents useful in the treatment, prevention, or management of a TNF-alpha-related condition.

In some particular embodiments, the therapeutic or prophylactic agent of the invention is administered in combination with one or more drugs used in the treatment of rheumatoid arthritis. For example, an anti-TNF-alpha polypeptide of the invention may be administered in combination with a disease modifying anti-rheumatic drug (DMARDs). A DMARD generally refers to a drug which reduces the rate of damage to bone and cartilage resulting from rheumatoid arthritis. DMARDs include, without limitation, azathioprine, ciclosporin (e.g., cyclosporine A), D-penicillamine, gold salts, hydroxychloroquine, leflunomide, methotrexate, minocycline, sulfasalazine, cyclophosphamide, and the like. Other drugs useful in the treatment of rheumatoid arthritis that may be administered in combination with the anti-TNF-alpha polypeptide of the invention include, without limitation, interleukin 1 (IL-1) blockers (Kineret), such as anakinra; monoclonal antibodies against B cells, such as rituximab (Rituxan); T cell costimulation blockers, such as abatacept (Orencia); interleukin 6 (IL-6) blockers, such as tocilizumab, an anti-IL-6 receptor antibody; and the like. In some embodiments, anti-TNF-alpha polypeptide of the invention is administered in combination with one or more other TNF-alpha blockers used against rheumatoid arthritis. For example, in some embodiments, a polypeptide of the invention is administered in combination with, e.g., Infliximab (Remicade™), Adalimumab (Humira), Etanercept (Enbrel), Certolizumab pegol (Cimzia), and Golimumab (Simponi). In some particularly preferred embodiments, a polypeptide of the invention is administered in combination with methotrexate. Combined effects may be additive or synergistic.

In some particular embodiments, the therapeutic or prophylactic agent of the invention is administered in combination with a one or more anti-inflammatory agents used in the treatment of rheumatoid arthritis. Anti-inflammatory agents include, but are not limited to, gluccocorticoids and non-steroidal anti-inflammatory drugs (NSAIDs), including ibuprofen, naproxen, meloxicam, etodolac, nabumetone, sulindac, tolementin, choline magnesium salicylate, diclofenac, diflusinal, indomethicin, piroxicam, and the like. Another NSAID involves Celecoxib, a selective COX-2 inhibitor, sold under the name Celebrex. In some embodiments, the anti-inflammaotry agent is an analgesic. Analgesics include, but are not limited to, paracetamol (acetaminophen), opiates, diproqualone, topical lidocaine, and the like.

The anti-TNF-alpha polypeptides of the invention, antigen-binding fragments, derivatives, or fusions thereof, may be administered alone or in combination with other prophylactic and/or therapeutic agents. Each prophylactic or therapeutic agent may be administered at the same time or sequentially in any order at different points in time; however, if not administered at the same time, they should be administered sufficiently close in time so as to provide the desired therapeutic or prophylactic effect. Each therapeutic agent can be administered separately, in any appropriate form and by any suitable route.

In various embodiments, the different prophylactic and/or therapeutic agents are administered less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, no more than 24 hours apart, no more than 48 hours apart, no more than 72 hours apart, no more than 96 hours apart, no more than 5 days apart, no more than 6 days apart, no more than a week apart, no more than 2 weeks apart, no more than three weeks apart, no more than a month apart, no more than two months apart, or no more than three months apart. In certain embodiments, two or more agents are administered within the same patient visit.

Various delivery systems are known and can be used to administer the agents of the invention, e.g., encapsulation in liposomes, microparticles, microcapsules, recombinant cells capable of expressing the anti-TNF-alpha polypeptides or fusions thereof (See, e.g., Wu and Wu, 1987, J. Biol. Chem. 262:4429-4432), construction of a nucleic acid as part of a retroviral or other vector, etc. Methods of administering agents of the invention include, but are not limited to, parenteral administration (e.g., intradermal, intramuscular, intraperitoneal, intravenous, and subcutaneous, including infusion or bolus injection), epidural, and by absorption through epithelial or mucocutaneous or mucosal linings (e.g., intranasal, oral mucosa, rectal, and intestinal mucosa, etc.).

In certain embodiments, the agents of the invention are administered intramuscularly, intravenously, or subcutaneously, and may be administered together with other biologically active agents. In a specific embodiment, the anti-TNFalpha polypeptide of the invention is formulated for subcutaneous administration as a sterile product. Administration can be systemic or local.

In a specific embodiment, it may be desirable to locally administer an agent of the invention to an area in need of treatment; this may be achieved by, for example, and not by way of limitation, local infusion, by injection, or by means of an implant, said implant being of a porous, non-porous, or gelatinous material, including membranes, such as sialastic membranes, or fibers. Typically, when administering an agent comprising an anti-TNF-alpha polypeptide, or antigen-binding fragment, derivative, or fusion thereof, care must be taken to use materials to which the polypeptide does not absorb.

In another embodiment, the agent can be delivered in a vesicle, in particular a liposome (see Langer, *Science*, 249: 1527 1533, 1990; Treat et al., in Liposomes in the Therapy of Infectious Disease and Cancer, Lopez-Berestein and Fidler (eds.), Liss, New York, pp. 353 365 (1989); Lopez-Berestein, ibid., pp. 3 17 327; see generally ibid.).

In another specific embodiment, agents of the invention may be delivered in a sustained release formulation, e.g., where the formulations provide extended release and thus extended half-life of the administered agent. Controlled release systems suitable for use include, without limitation, diffusion-controlled, solvent-controlled, and chemically-controlled systems. Diffusion controlled systems include, for example reservoir devices, in which the anti-TNF-alpha agents of the invention are enclosed within a device such that release of the molecules is controlled by permeation through a difussion barrier. Common reservoir devices include, for example, membranes, capsules, microcapsules, liposomes, and hollow fibers. Monolithic (matrix) device are a second type of diffusion controlled system, wherein the anti-TNF-alph agents are dispersed or dissolved in an rate-controlling matrix (e.g., a polymer matrix). Agents of the invention can be homogeneously dispersed throughout a rate-controlling matrix and the rate of release is controlled by diffusion through the matrix. Polymers suitable for use in the monolithic matrix device include naturally occurring polymers, synthetic polymers and synthetically modified natural polymers, as well as polymer derivatives.

Any technique known to one of skill in the art can be used to produce sustained release formulations comprising one or more agents described herein, e.g., in particular anti-TNF-alpha polypeptides comprising an antibody single domain fused to an albumin-binding domain. See, e.g. U.S. Pat. No. 4,526,938; PCT publication WO 91/05548; PCT publication WO 96/20698; Ning et al., "Intratumoral Radioimmunotheraphy of a Human Colon Cancer Xenograft Using a Sustained-Release Gel," *Radiotherapy & Oncology*, 39:179 189, 1996; Song et al., "Antibody Mediated Lung Targeting of Long-Circulating Emulsions," PDA *Journal of Pharmaceutical Science & Technology*, 50:372 397, 1995; Cleek et al., "Biodegradable Polymeric Carriers for a bFGF Antibody for Cardiovascular Application," *Pro. Intl. Symp. Control. Rel. Bioact. Mater.*, 24:853 854, 1997; and Lam et al., "Microencapsulation of Recombinant Humanized Monoclonal Antibody for Local Delivery," *Proc. Int'l. Symp. Control Rel. Bioact. Mater.*, 24:759 760, 1997, each of which is incorporated herein by reference in its entirety. In one embodiment, a pump may be used in a controlled release system (see Langer, supra; Sefton, *CRC Crit. Ref Biomed. Eng.*, 14:20, 1987; Buchwald et al., Surgery, 88:507, 1980; and Saudek et al., *N. Engl. J. Med.*, 321:574, 1989). In another embodiment, polymeric materials can be used to achieve controlled release of agents comprising anti-TNF-alpha polypeptides, or antigen-binding fragments, derivatives, or fusions thereof (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, J., *Macromol. Sci. Rev. Macromol. Chem.*, 23:61, 1983; see also Levy et al., *Science*, 228:190, 1985; During et al., *Ann. Neurol.*, 25:351, 1989; Howard et al., *J. Neurosurg.*, 7 1:105, 1989); U.S. Pat. No. 5,679,377; U.S. Pat. No. 5,916,597; U.S. Pat. No. 5,912,015; U.S. Pat. No. 5,989,463; U.S. Pat. No. 5,128,326; PCT Publication No. WO 99/15154; and PCT Publication No. WO 99/20253). In yet another embodiment, a controlled release system can be placed in proximity of the therapeutic target (e.g., an affected joint), thus requiring only a fraction of the systemic dose (see, e.g., Goodson, in Medical Applications of Controlled Release, supra, vol. 2, pp. 115 138 (1984)). Other controlled release systems are discussed in the review by Langer, *Science*, 249:1527 1533, 1990.

9. Pharmaceutical Compositions and Kits

The invention further provides a pharmaceutical composition comprising a pharmaceutically acceptable carrier and an agent of the invention, said agent comprising an anti-TNF-alpha polypeptide or an anti-TNF-alpha polypeptide-encoding nucleic acid of the invention. In preferred embodiments, the pharmaceutical composition comprises an anti-TNF-alpha polypeptide, antigen-binding fragment, derivative, or fusion thereof, where fusion is to an albumin-binding domain and/or where the polypeptide is de-immunized; and the polypeptide is combined with a pharmaceutically acceptable carrier for administration to a subject. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's complete and incomplete adjuvant), excipient, or vehicle with which the agent is administered. Such pharmaceutical carriers can be sterile liquids, such as water and oils, including those of petroleum, animal, vegetable, or synthetic origin, including, e.g., peanut oil, soybean oil, mineral oil, sesame oil and the like. Water is a common carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Additional examples of pharmaceutically acceptable carriers, excipients, and stabilizers include, but are not limited to, buffers such as phosphate, citrate, and other organic acids; antioxidants including ascorbic acid; low molecular weight polypeptides; proteins, such as serum albumin and gelatin; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™ as known in the art. The pharmaceutical composition of the present invention can also include a lubricant, a wetting agent, a sweetener, a flavoring agent, an emulsifier, a suspending agent, and a preservative, in addition to the above ingredients. These compositions can take the form of solutions, suspensions, emulsion, tablets, pills, capsules, powders, sustained-release formulations and the like.

The compositions of the invention can be formulated as neutral or salt forms. Pharmaceutically acceptable salts include, but are not limited to those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

In certain embodiments of the invention, pharmaceutical compositions are provided for use in accordance with the methods of the invention, said pharmaceutical compositions comprising a therapeutically and/or prophylactically effective amount of an agent of the invention along with a pharmaceutically acceptable carrier.

In preferred embodiments, the agent of the invention is substantially purified (i.e., substantially free from substances that limit its effect or produce undesired side-effects). In a specific embodiment, the host or subject is an animal, preferably a mammal such as non-primate (e.g., cows, pigs, horses, cats, dogs, rats etc.) and a primate (e.g., monkey such as, a cynomolgus monkey and a human). In a preferred embodiment, the host is a human.

The invention provides further kits that can be used in the above methods. In one embodiment, a kit comprises one or more agents of the invention, e.g., in one or more containers. In another embodiment, a kit further comprises one or more other prophylactic or therapeutic agents useful for the treatment of a TNF-alpha-related conditions, in one or more containers.

The invention also provides agents of the invention packaged in a hermetically sealed container such as an ampoule or sachette indicating the quantity of the agent or active agent. In one embodiment, the agent is supplied as a dry sterilized lyophilized powder or water free concentrate in a hermetically sealed container and can be reconstituted, e.g., with water or saline, to the appropriate concentration for administration to a subject. Typically, the agent is supplied as a dry sterile lyophilized powder in a hermetically sealed container at a unit dosage of at least 5 mg, more often at least 10 mg, at least 15 mg, at least 25 mg, at least 35 mg, at least 45 mg, at least 50 mg, or at least 75 mg. In an alternative embodiment, an agent of the invention is supplied in liquid form in a hermetically sealed container indicating the quantity and concentration of agent or active agent. Typically, the liquid form of the agent is supplied in a hermetically sealed container at at least 1 mg/ml, at least 2.5 mg/ml, at least 5 mg/ml, at least 8 mg/ml, at least 10 mg/ml, at least 15 mg/kg, or at least 25 mg/ml.

The compositions of the invention include bulk drug compositions useful in the manufacture of pharmaceutical compositions (e.g., impure or non-sterile compositions) as well as pharmaceutical compositions (i.e., compositions that are suitable for administration to a subject or patient). Bulk drug compositions can be used in the preparation of unit dosage forms, e.g., comprising a prophylactically or therapeutically effective amount of an agent disclosed herein or a combination of those agents and a pharmaceutically acceptable carrier.

The invention further provides a pharmaceutical pack or kit comprising one or more containers filled with one or more of the agents of the invention. Additionally, one or more other prophylactic or therapeutic agents useful for the treatment of a TNF-alpha related condition, e.g., rheumatoid arthritis, can also be included in the pharmaceutical pack or kit. The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use, or sale for human administration.

In some embodiments, prophylactic or therapeutic agents of the invention are administered subcutaneously. Subcutaneous administration allows for fast delivery of the agent, e.g., within a few minutes after subcutaneous administration. In particular embodiments, for example, an anti-TNF-alpha polypeptide of the invention is provided with a pharmaceutically acceptable carrier, wherein the carrier is suitable for subcutaneous administration. Generally, the carrier will be sterile and has an osmolality compatible with administration into the blood.

Kits and devices facilitating self-administration also are preferred in some embodiments. For example, a "pen" as used with respect to delivery of insulin or Humira, may be used to effect subcutaneous delivery of an agent of the invention. (See, e.g., McCoy E K, et al. 2010 "A Review of Insulin Pen Devices" *Postgrad Med* 122(3): 81-88; and Pearson, T L. 2010 "Practical Aspects of Insulin Pen Devices," Symposium, *J. of Diabetes Sci and Tech,* 4(3): 522-531, which each are hereby incorporated-by-reference in their entireties). The pen device for delivery of an anti-TNF-alpha agent of the invention may be disposable or reusable, and may come prefilled or designed for use with cartridges of the agent. Prefilled disposable pens on the market include those sold under ther brand names Humalog®, KwikPen®, Humulin®, Lantus®, Apidra®, Levemir®, Novolog®, FlexPen®, and the like. Refillable pens on the market include those sold under the brand names Autopen®, HumaPen®, LUXURA™, NovoPen®, and OptiClik®, and the like. Pen devices provide an alternative to vial-and-syringe approaches for self-administration of therapeutic agents by the subcutaneous route, and can offer a number of advantages including greater ease of use, greater portability and convenience, improved dosing accuracy, less pain, greater social acceptance, greater discreteness, and greater patient compliance.

In some embodiments, the pen has a dial-back feature, allowing for reversing the amount to be administered by "dialing back". In some embodiments, the pen has a memory and digital display of the last dose or a last number doses. Pens normally are kept at room temperature, and insulated storage packs may be used where pens are stored in places subjected to extremes of temperature. The pen device may be sold with or separately from pen needles. Needles may come in a variety of gauges and/or lengths. Gauges can be about 25 to about 35 gauge, such as 29 gauge, 30 gauge, 31 gauge, or 32 gauge, and about 2 mm to about 30 mm in length, e.g., about 3 mm, about 5 mm, about 10 mm, about 12.7 mm, about 15 mm, about 20 mm, or about 25 mm in length.

Generally, the ingredients of compositions of the invention are supplied either separately or mixed together in unit dosage form, for example, as a dry lyophilized powder or water-free concentrate in a hermetically sealed container such as an ampoule or sachette indicating the quantity of agent or active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

47

All references including patent applications and publications cited herein are incorporated herein by reference in their entirety and for all purposes to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

EXAMPLES

Example 1

Sequencing VL Single Domains

Eighteen VL single domains that show particularly high affinity binding to human TNF-alpha were sequenced—VL18 (SEQ ID NO:1) and VL11 (SEQ ID NO:2), as well as SEQ ID NOs:3-18. The sequences were compared in terms of the four framework regions (FR1, FR2, FR3, and FR4) and the three complementary determining regions (CDR1, CDR2, and CDR3) of each VL single domain. Two VL domains showing high affinity binding were selected for combination as dimers—VL18 (SEQ ID NO:1) and VL11 (SEQ ID NO:2). The results are illustrated in FIG. 1.

Example 2

Construction and Binding Analysis of VL-VL Dimers

Two VL domains showing high affinity binding were selected for combination as dimers—VL18 (SEQ ID NO:1) and VL11 (SEQ ID NO:2). As a spacer between the two VL domains, either a 8 amino acid GlySer linker; 13 amino acid GlySer linker; or 18 amino acid GlySer linker was used. Dimeric combinations included VL18-VL18, VL18-VL11, VL11-VL11, and VL11-VL18. VL18 and VL11 monomers were cloned into dimers conformation in pET28a (Novagen) expression vector using a two step cloning strategy. Briefly, the carboxy terminal VL was cloned first with NheI and NotI, while in the second step the other VL was inserted by Not and XhoI.

To express the anti-TNF-alpha antibody fragments, each DNA plasmid was transformed into BL21 (DE3) competent cells. Briefly, a fresh colony of each clone was grown at 37° C. overnight in SB medium supplemented with kanamycin. A 10 ml sample of cells was used to inoculate 1 L of SB medium supplemented with kanamycin. Cells were grown at 37° C. until $A_{600nm}$ reached 0.9. Antibody expression was induced by the addition of 0.5 mM IPTG and growth was continued for 6-18 hours, at 16° C. The expressed products were identified via Western Blot analysis, confirming dimer formation by comparison to the individual VL monomers. Results for the VL monomers and VL18-VL18, VL18-VL11; VL11-VL18, and VL11-VL11 dimers are illustrated in FIGS. 2A-C.

The antibody fragments were purified from the concentrated supernatants of induced cultures via their hexahistidine tail ("hexahistidine" disclosed as SEQ ID NO: 60) by Talon spin columns (Clontech) according to the manufacturer's protocol.

Relative binding activities of VL monomers and constructed dimers were measured for human and rat TNF-alpha, while BSA was used as a negative control. Briefly, a 384-well ELISA plate was coated with 80 ng of human or rat TNF-alpha and incubated overnight at 4° C. Wells were blocked for one hour at 37° C. with 3% BSA in PBS. Antibody fragments were added to the wells and incubated for 1 h at room temperature. After washing the wells with PBS, anti-HA-HRP mAb (Roche) was used for detection. Optical density at 405 nm was measured and assays were performed in triplicate. Remicade™ was used as positive control and VL 4BL (Goncalves J et al. *J Biol Chem*. (2002) 277(35):32036-45) was used as an irrelevant antibody. VL18-3L-VL11 dimer (SEQ ID NO:32) was selected for further studies. The results are illustrated in FIG. 2D.

Example 3

Construction of VL-VL Fusions with Albumin-Binding Domains

DNA fragments comprising albumin-binding domains of PEP and albumin-binding fragments or derivatives thereof, were generated using PCR and SpeI and NcoI restriction sites were added at the fragment 5' and 3' ends, respectively. The resulting PCR fragments were gel-purified, digested with the SpeI and NcoI restriction enzymes and cloned into the phagemid vector pComb3X. The amino acid sequence of the expressed peptides comprise SEQ ID NO:30 and fragments, or derivatives thereof.

The peptides corresponding to SEQ ID NO:30, and albumin-binding fragments or derivatives thereof, were fused to VL18-3L-VL11 (SEQ ID NO:32) to give antibody fusions and the fusions were tested as to whether they retain binding affinity to TNF-alpha, while also binding to human, rat, and/or mouse serum albumin. Fusion proteins were prepared with the peptide corresponding to SEQ ID NO:30 and the VL18-3L-VL11 dimer corresponding to SEQ ID NO: 32 to produce the fusion protein VL18-3L-VL11-PEP corresponding to SEQ ID NO: 33.

To express and purify the VL18-3L-VL11 dimer and the VL18-3L-VL11-3L-PEP fusion protein, pET28a plasmid containing each gene was used to transform *E. coli* Tuner (DE3) cells.

A fresh colony of each clone was grown at 37° C. overnight in SB medium supplemented with kanamycin. A 10 ml sample of cells was used to inoculate 1 L of SB medium supplemented with kanamycin. Cells were grown at 37° C. until $A_{600nm}$ reached 0.9. Antibody expression was induced by the addition of 0.1 mM isopropyl-1-thio-β-D-galactoside (IPTG) and growth was continued for 18 hours, at 16° C. After induction, bacteria were harvested by centrifugation (4,000×g, 4° C., 15 min) and resuspended in 50 ml equilibration buffer (20 mM Hepes, 1 M NaCl, 30 mM imidazole, 10% glycerol, pH 7.4) supplemented with protease inhibitors (Roche). Cells were lysed by sonication. Centrifugation (14000×g, 4° C., 30 min) was used to remove cellular debris, and the supernatant was filtered through a 0.2-µm syringe filter.

All chromatographic steps were performed at 4° C. First, antibody fragments extracts were purified by nickel chelate affinity chromatography using the C-terminal His-tag. Bound proteins were eluted with a linear imidazole gradient from 0 to 300 mM imidazole in 20 mM Hepes, 0.5 M NaCl; 10% glycerol (pH 7.4). The appropriate fractions were pooled, concentrated and then purified by size exclusion chromatography using Superdex column and Hepes buffer (20 mM Hepes, 200 mM NaCl, 5% glycerol, pH 7.4). Purified antibody fragments were analyzed by SDS-PAGE followed by Coomassie-Blue staining and western-blot with HRP-conjugated anti-HA monoclonal antibody. Protein concentration was determined by measuring the optical density at 280 nm.

Example 4

Anti-TNF-Alpha Dimeric Fusions Bind Serum Albumin

Binding of the fusions of Example 3 to albumin was tested by ELISAs. Binding ELISAs were performed as described briefly: albumin from human, rat, or mouse sera, at 10 µg/ml, was immobilized overnight in 96 well-plates at 4° C. After 2 h blocking with PBS/3% soy milk, recombinant single domain antibodies (VL18, VL11), dimers thereof (VL18-3L-VL11), and fusions thereof to albumin-binding domains (VL18-3L-VL11-PEP) were incubated for 1 hour at room temperature. After washing the wells with PBS, anti-HA-HRP mAb (Roche) was used for detection. Optical density at 405 nm was measured and assays were performed in triplicate.

The binding studies compare binding of VL18-3L-VL11-PEP fusions with unfused VL18-3L-VL11 to each of human, rat, and mouse sera albumin. The fusions show increased serum albumin binding to each of human, mouse, and rat albumin at one or more concentrations. That is, albumin-binding by VL18-3L-VL11-PEP according to the invention shows several fold improvements, e.g., by five or six fold or more, compared to unfused VL18-3L-VL11.

Competition ELISAs further demonstrate albumin binding of the fusions according to the invention. Competition ELISAs are performed as described briefly: VL18-3L-VL11-PEP fusions at increasing concentrations were pre-incubated with 10 µg of each of the different albumins for 1 h at room temperature and subsequently added to the microtiter plates coated with the corresponding albumins. Detection was performed with mouse HRP conjugated anti-HA-tag antibody and absorbance was read at 405 nm. In each instance, preincubation reduces binding.

Example 5

Anti-TNF-Alpha Dimeric Fusions Show Improved Pharmacokinetics In Vivo

Pharmokinetics of fusions of Example 3 were tested by administration to rats and mice to determine the serum half-life thereof in vivo. VL18-3L-VL11-PEP was administered at various concentrations by IP or IV injection; while unfused VL18-3L-VL11 was administered similarly to control rats. 100 mg of the fusions were injected i.p. into Wistar female rats. Plasma samples were obtained from injected rats at regular intervals of 5, 30, 60, 120, and 360 minutes, 24 hours, 48 hours, and 72 hours, and assayed for concentration of the fusion or unfused VL18-3L-VL11 by ELISA. Briefly, TNF-alpha was immobilized in 384 well-plates (80 ng/well) overnight at 4° C. After 2 h blocking with soy milk, recombinant antibody fragments were titrated in duplicates and incubated for 1 h at RT. Detection was performed with mouse HRP-conjugated anti-HA antibody (Roche) using ABTS substrate. Absorbance was measured at 450 nm in an ELISA-reader. The plasma concentration is obtained for each time point and fitted to a two-compartment elimination model. Data were normalized considering maximal concentration at the first time point (5 minutes).

Figures 3A, 3B:
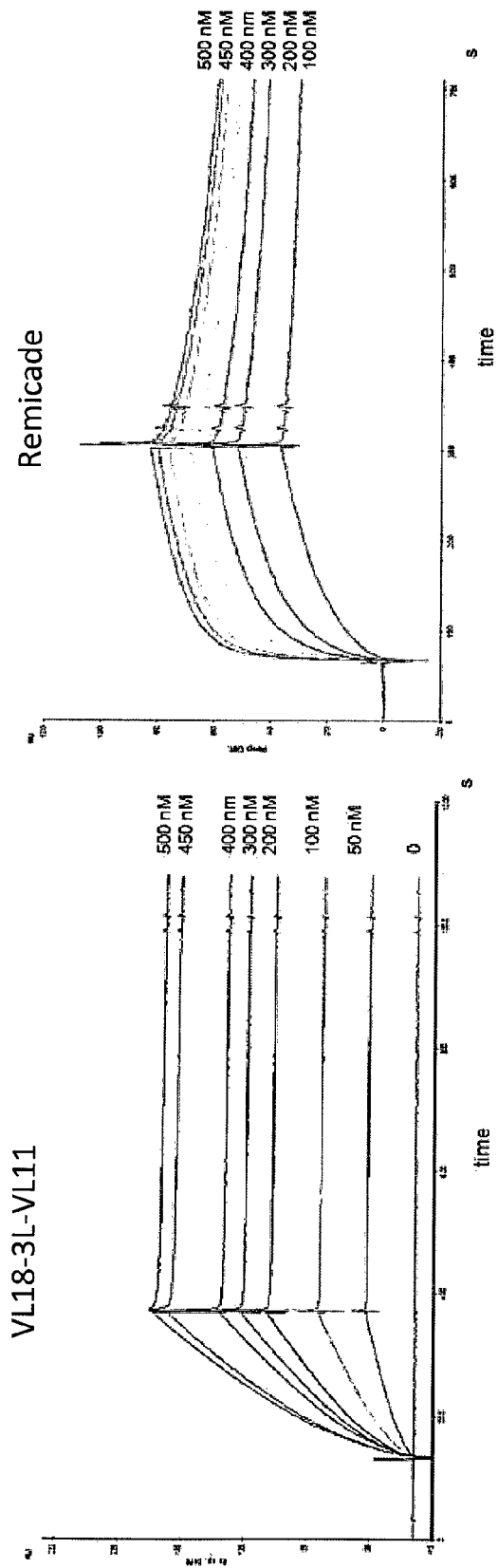
Figure 3C:
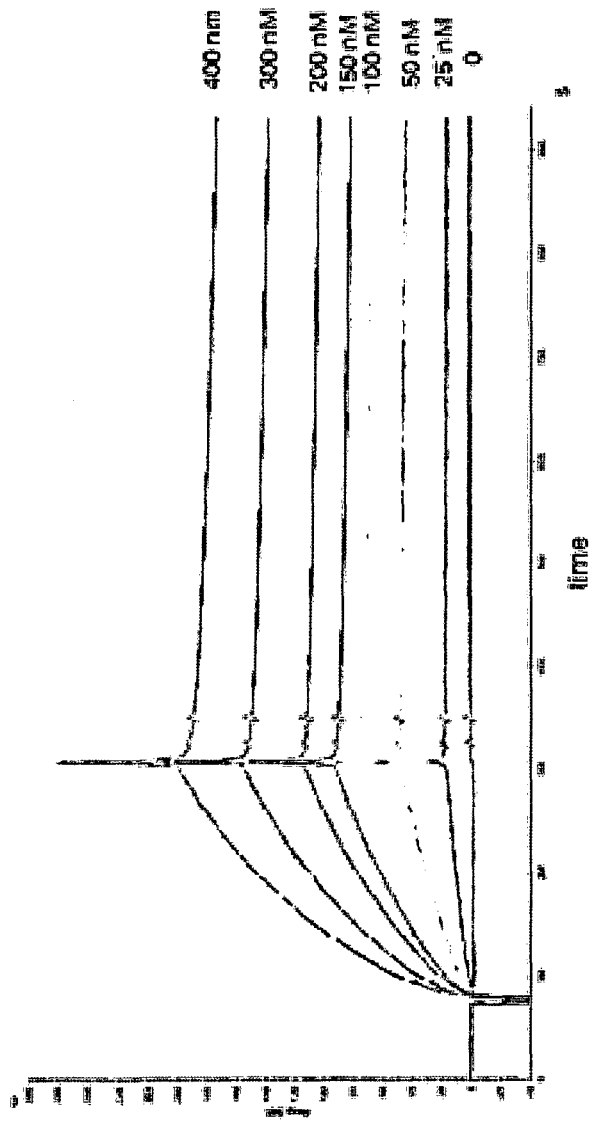
Figure 3D:
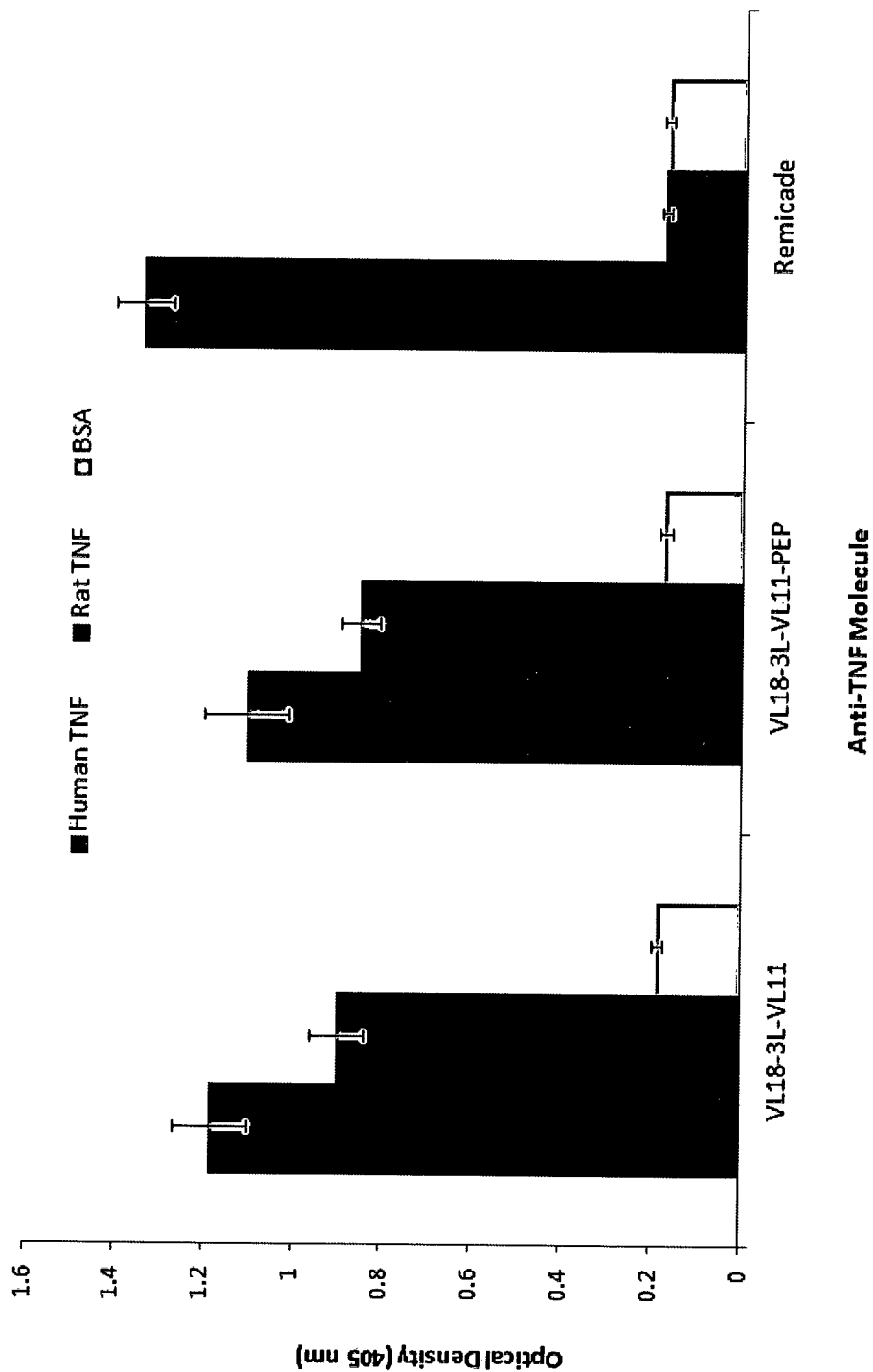
Figure 3F:
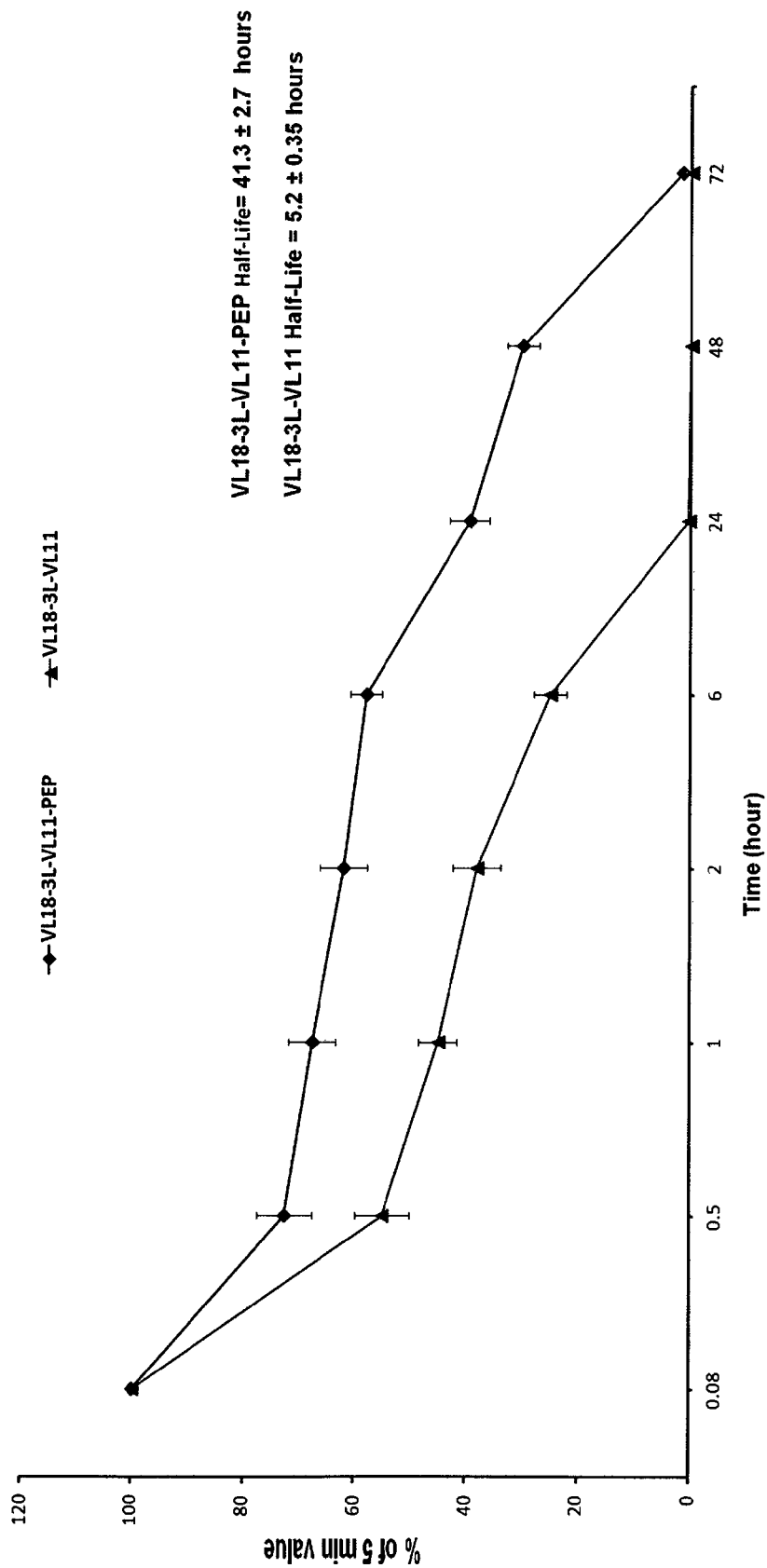

The pharmacokinetic studies compare the serum half-lives of VL18-3L-VL11-PEP fusion to unfused VL18-3L-VL11 in vivo. The fusion shows increased serum half-life at one or more concentrations. That is, in vivo serum half-life of VL18-3L-VL11-PEP fusion according to the invention shows several fold improvement, e.g., by 200-1000% (i.e., by 2 to 10 fold), compared to unfused VL18-3L-VL11. Results are illustrated in FIG. 3F.

Example 6

Anti-TNF-Alpha Dimeric Fusions Retain Antigen-Binding Specificity

Fusions of Example 3 were analyzed for binding specificity of anti-TNF-alpha antibody portions to TNF-alpha using ELISAs. Binding ELISAs were performed as described herein. Briefly, human TNF-alpha, at 80 ng/well, was immobilized overnight in 96 well-plates at 4° C. After 2 h blocking with PBS/3% soy milk, recombinant single domain antibodies (VL18, VL11), dimers thereof (VL18-3L-VL11), and fusions thereof to albumin-binding domains (VL18-3L-VL11-PEP) were incubated for 1 h at room temperature. After washing the wells with PBS, anti-HA-HRP mAb (Roche) was used for detection. Optical density at 405 nm was measured and assays were performed in triplicate.

The binding studies compare binding of VL18-3L-VL11-PEP fusions with unfused VL18-3L-VL11 to TNF-alpha. Each fusion maintains specific binding to TNF-alpha at one or more concentrations. That is, TNF-alpha binding by VL18-3L-VL11-PEP according to the invention shows approximately the same binding specificity compared to unfused VL18-3L-VL11.

Example 7a

Binding Affinities of VL18-3L-VL11 and VL18-3L-VL11-PEP

The binding affinity between the anti-TNF-alpha polypeptide VL18-3L-VL11 (a VL dimeric construct) and VL18-3L-VL11-PEP against human TNF-alpha, as well as mouse, rat, or human albumin, were obtained using a BIAcore 2000. The BIAcore system characterizes molecules in terms of their specificity, association and dissociation rates ($K_{on}$ and $K_{off}$ kinetics), and binding strength (affinity) and is based on Surface Plasmon Resonance (SRP), an optical phenomenon that facillitates detection of unlabled interactants in real time.

Human TNF-alpha, mouse, rat, or human albumin, were captured on a CM5 chip using amine coupling at about 1000 resonance units. VL18-3L-VL11 or VL18-3L-VL11-PEP at 0, 25, 50, 100, 150, 200, 300, 400, 450, and 500 nM were injected at a flow rate of 10 µl/min for 4 min. The bound protein was allowed to dissociate for 10 min before matrix regeneration using 10 mM Glycine, pH 1.5. The signal from an injection passing over an uncoupled cell was subtracted from that of an immobilized cell to generate sensorgrams of the amount of molecule bound as a function of time. Remicade™ affinity was also measured and used as a control. The running buffer, HBS, was used for all sample dilutions. BIAcore kinetic evaluation software (version 3.1) was used to determine $K_D$ from the association and dissociation rates using a one-to-one binding model. Results are illustrated in FIGS. 3A-C.

The relative binding activity and specificity of VL18-3L-VL11 and VL18-3L-VL11-PEP to human, rat, and mouse TNF-alpha also was determined. The protocol outlined above can be followed, using 100 ng of human TNF-alpha, rat TNF-alpha, and BSA; evaluated using ELISA; and absorbance read at 405 nm. Remicade™ anti-TNF product was used as a control. Represented data are means of triplicate±S.D. Results are illustrated in FIG. 3C.

A further binding study compared the relative binding affinity and specificity of VL18-3L-VL11 to 100 ng of human TNF-alpha, cynomologous TNF-alpha, mini-pig TNF-alpha, and BSA, again using ELISA and measuring optical density at 405 nm. Results are illustrated in FIG. 3E.

Affinity and binding kinetic parameters for VL18-3L-VL11, VL18-3L-VL11-PEP, along with those for VL18 and VL11 monomers and for Remicade™, are shown in Table 1 below.

TABLE 1

Affinity and binding kinetic parameters for anti-TNF VL18 and VL11 monomers and VL18-3L-VL11 dimer.

| Anti-TNF Molecule | Kon $[M^{-1}S^{-1}]$ | Koff $[S^{-1}]$ | Kd [nM] |
|---|---|---|---|
| VL18 | $1.7 \times 10^4 \pm 0.59$ | $1.2 \times 10^{-4} \pm 0.43$ | $6.9 \pm 0.62$ |
| VL11 | $0.3 \times 10^4 \pm 0.10$ | $4.8 \times 10^{-5} \pm 3.47$ | $43.6 \pm 7.6$ |
| VL18-3L-VL11 | $2.5 \times 10^4 \pm 0.85$ | $1.7 \times 10^{-5} \pm 0.21$ | $0.7 \pm 0.23$ |
| VL18-3L-VL11-PEP | $2.7 \times 10^4 \pm 0.85$ | $2.2 \times 10^{-5} \pm 0.4$ | $0.8 \pm 0.8$ |
| Remicade | $2.6 \times 10^5 \pm 0.31$ | $5.5 \times 10^{-4} \pm 0.32$ | $2.11 \pm 0.20$ |

Example 7b

Neutralization of TNF-Dependent Cytolytic Activity by VL18-3L-VL11 and VL18-3L-VL11-PEP Binding affinity of VL18-3L-VL11 for human TNF-alpha also was measured using an in vitro assay for neutralization of TNF-alpha-dependent cytolytic activity. Binding affinity of VL18-3L-VL1'-PEP also was measured in this assay.

In order to measure the anti-TNF VL18-3L-VL11 and VL18-3L-VL1'-PEP blocking effect on TNF-alpha/TNFR interaction, a murine aneuploid fibrosarcoma cell line (L929) was used as a cytotoxic TNF-mediated assay. Briefly, L929 cells were grown to 90% confluency in Dulbecco's modified Eagle's medium supplemented with 10% fetal bovine serum, penicillin (100 units/ml), streptomycin sulfate (10 µg/ml), and L-glutamine (2 mM). Cells were plated in 96-well microtiter plates at a density of 25,000 cells/well and then incubated overnight. Serial dilutions of anti-TNF-alpha antibodies to be tested were mixed with a cytotoxic concentration of TNF-alpha (final assay concentration 1 ng/ml) or in absence of this cytokine in order to measure the cell viability. Actinomycin D was added to this mixture at a final concentration of 1 µg/ml to increase the cell sensitivity. After at least 2 hrs of incubation at 37° C. with shaking, this mixture was added to the plated cells. Cells with mixture were incubated for 24 hours at 37° C. in an atmosphere of 5% $CO_2$. Cell viability was determined using the tetrazolium salt WST-1 (ROCHE) (10 µl/well) after at least 30 min of incubation by measuring the absorbance at 450 nm. Remicade™ was used as a control. An irrelevant antibody (VL 4BL) was used as negative control (C−).

Figure 4:
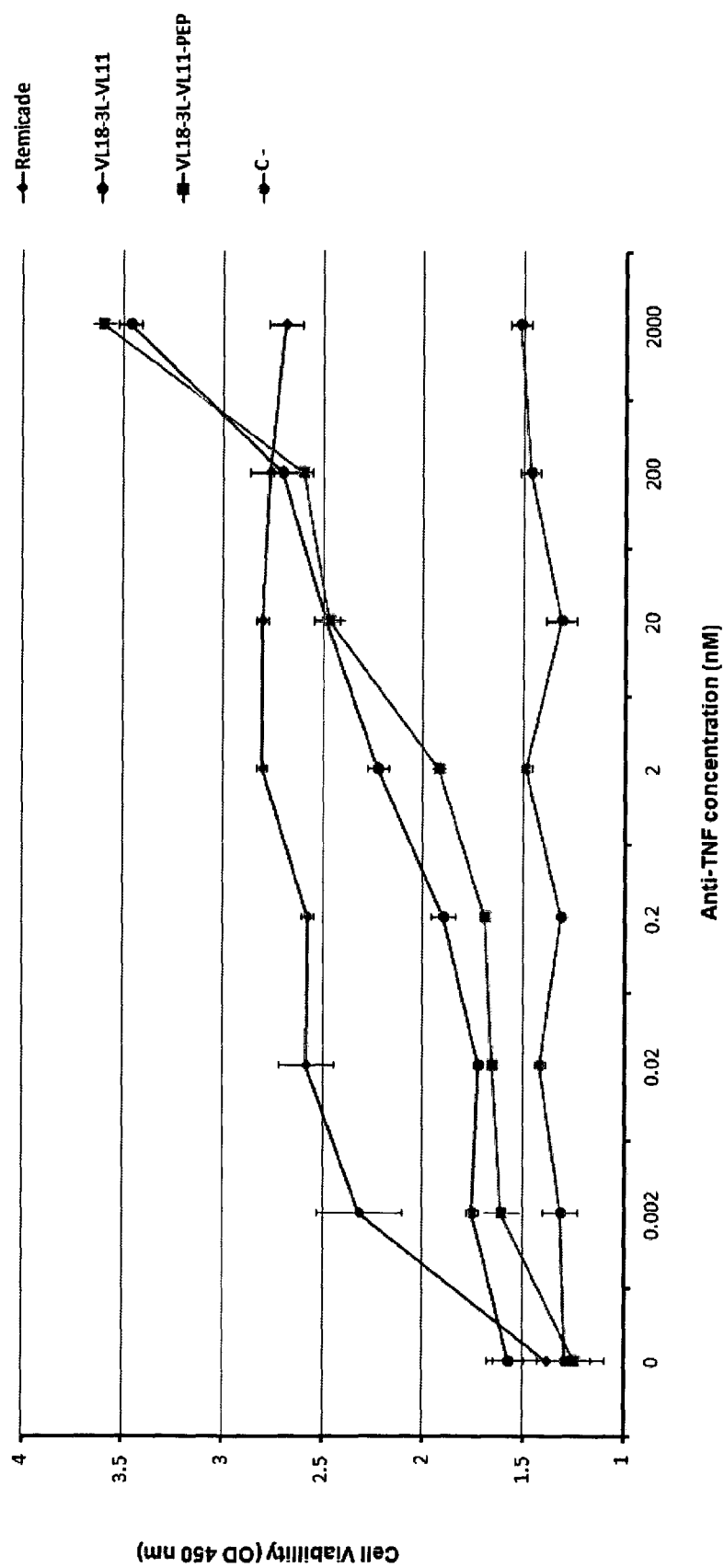
FIG. 4 illustrates results of an assay for neutralization of TNF-alpha dependent cytolytic activity using VL-VL dimers of the invention, which shows that the dimers protected L929 cells from TNF-induced cytotoxicity.

It was shown that VL18-3L-VL11 and VL18-3L-VL11-PEP protected L929 cells from TNF-α induced cytotoxicity, thus neutralizing TNF-alpha activity in doses comparable to products on the market (Remicade™). Results are illustrated in FIG. 4.

Example 8

Therapeutic Effects of VL18-3L-VL11 and VL18-3L-VL-PEP Dimers

To determine therapeutic effects of VL18-3L-VL11 and VL18-3L-VL11-PEP, an established rat-adjuvant induced arthritis model (AIA) was used. Freunds complete adjuvant (FCA) induces rheumatoid arthritis in rats. For example, an injection of FCA in the base of the tail results in chronic arthritis in the rat, involving multiple joints and promoting a widespread systemic disease, severe discomfort, and distress.

Figure 5:
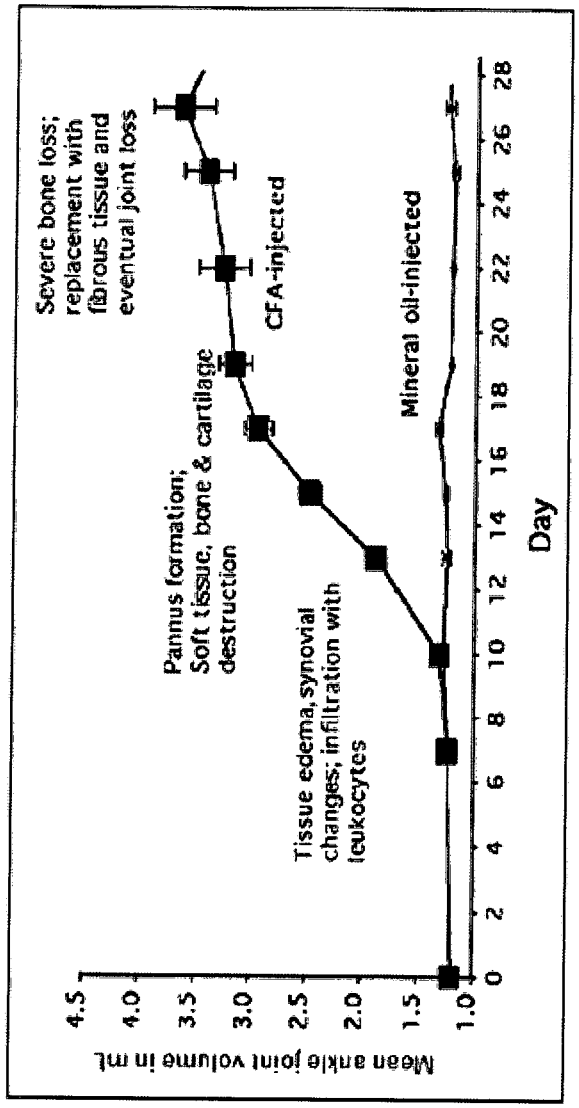
FIG. 5 illustrates disease progression induced in an adjuvant-induced arthritis model in Wistar female rats.

Wistar female rats (Charles River) with a mean bodyweight of 150-170 g, received an injection of FCA (1 mg/ml) intradermally (i.d.). The induced arthritis is assessed over 3 weeks following disease induction, based on the following: clinical scores (limb analysis), bodyweight, measurement of ankle joints, and histologically, as described below. All rats were bred and maintained under specific pathogen-free conditions at Institute of Medicine animal breeding facility according to institute guidelines. The animals were fed with standard rodent chow and water and maintained in ventilated cages. An adapted AIA model cartoon (adapted from In Vivo Models of Inflammation, Vol. I, C. S. Stevenson, L. A. Marshall, and D. W. Morgan (eds.), page 17 (2006) Birkhauser Veriag Basel, Switzerland) is illustrated in FIG. 5.

Three independent experiments were run. The first experiment (n=3) aimed to evaluate the half-life of the VL dimeric constructs, with and without fusion to PEP, under different administration routes. Administrations using IV, IP, and SC routes were used. Pharmacokinetics measurements were performed as described in Example 5. The VL18-3L-VL11 half-life average was found to be 5.1 hours. The VL18-3L-VL11-PEP half-life average was found to be 42 hours, representing an over 8 fold increase. These results inform the frequency of administration via injection.

The second experiment (n=3) aimed to determine dosage. Three test doses were administered at 50 µg, 100 µg, and 200 µg by IP injection. The dose of 100 µg proved satisfactory and was chosen for efficacy experiments.

The third experiment aimed to determine efficacy. A group of rats (n=6) were treated with 100 µg of VL18-3L-VL11 by IP injection. Other groups were treated at 2 days intervals with VL18-3L-VL11-PEP. PBS was used as a negative control (animal were injected with the vehicle only) and dexamethasone at 400 µg (daily) was used as a positive control.

Figure 6:
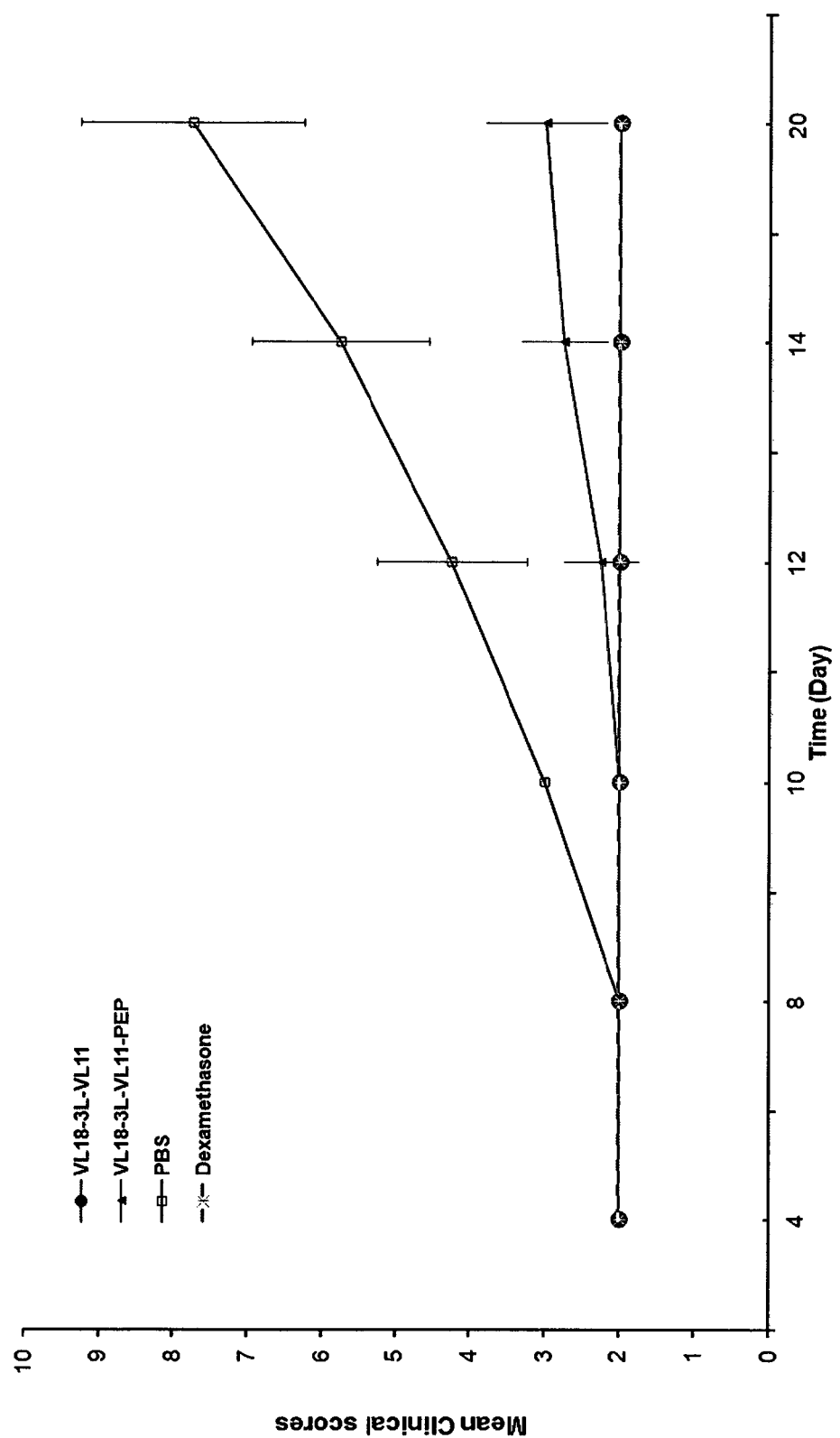
FIG. 6 illustrates therapeutic effect of VL-VL dimers of the invention in an established rat adjuvant-induced arthritis model (AIA) based on clinical assessment of four limbs.

The treatment period was for 3 weeks and animals were monitored daily for clinical symptoms of arthritis. Evaluation was based on the total score of the four limbs of each animal. The severity of the arthritis was quantified at 2-4-day intervals by a clinical score measurement from 0 to 3 as follows: 0=normal; 1=slight erythema; 2=moderate erythema; 3=strong erythema to incapacitated limb; max score=12. Results are mean valuses+/−S.D. and are illustrated in FIG. 6.

Figure 7:
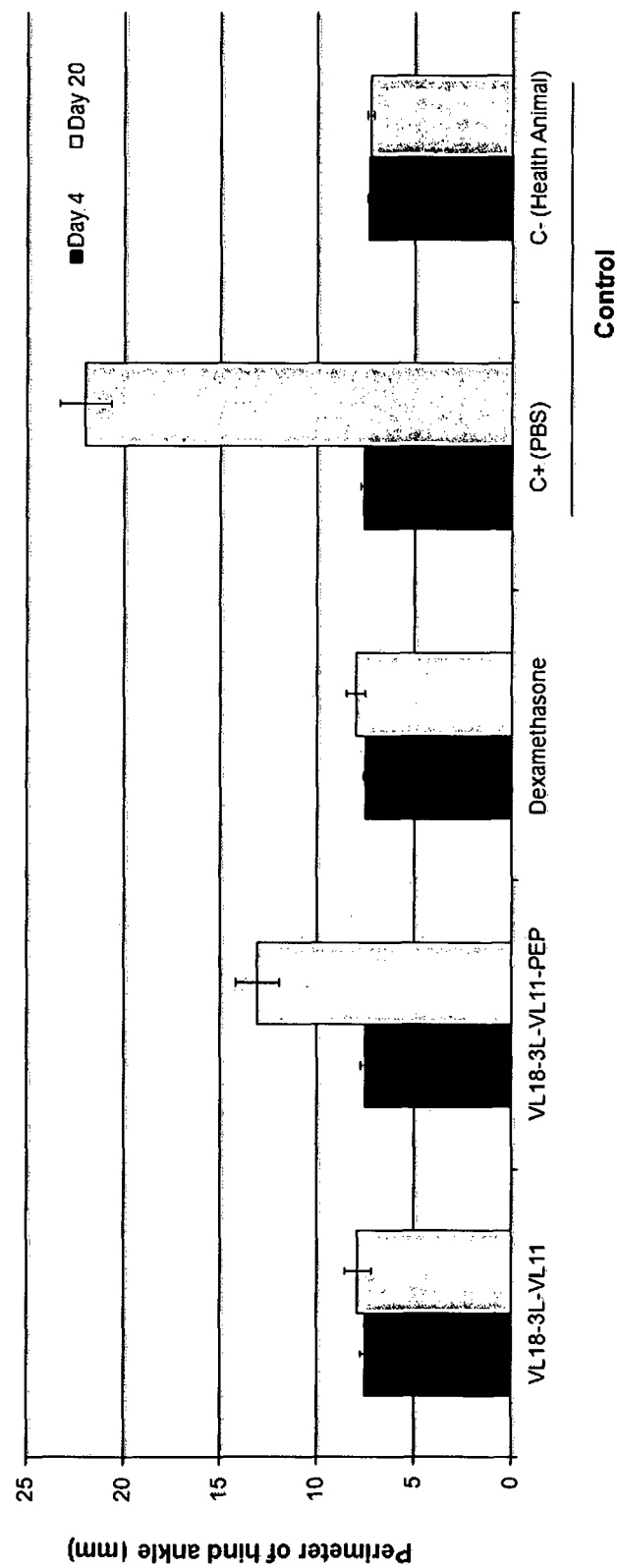
FIG. 7 illustrates therapeutic effect of VL-VL dimers of the invention in an established rat adjuvant-induced arthritis model (AIA) based on changes in hind ankle swellings.
Figures 8A, 8B, 8C, 8D, 8E:
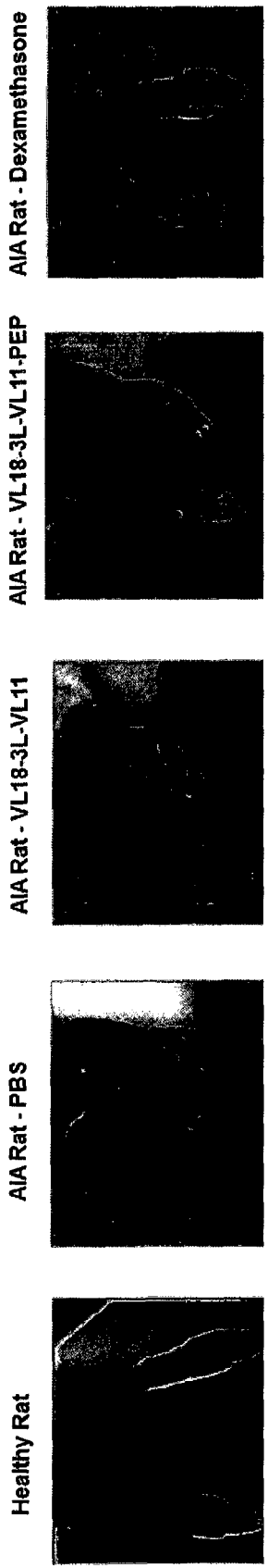
FIGS. 8A-E illustrate photographically the therapeutic effect of VL-VL dimers of the invention in an established rat adjuvant-induced arthritis model (AIA) based on changes in hind ankle swellings.
Figure 9D:
Figure 9F:
Figure 9C:
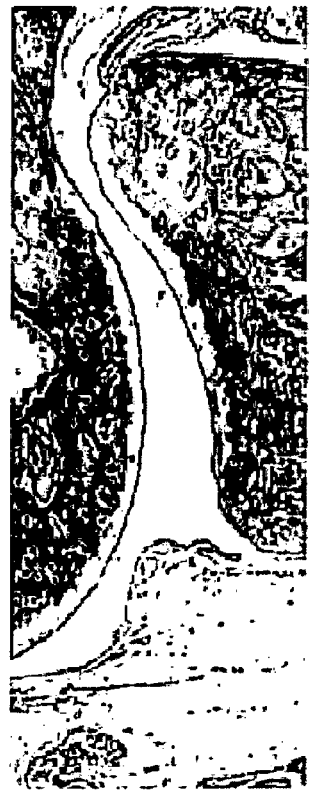
Figure 9E:
Figure 10A:
FIGS. 10A-B illustrates two recombinant VL-VL dimers of the invention: VL18-3L-VL11 (FIG. 10A), a recombinant single domain antibody fragment (sdAb) in dimeric form (monomer VL18 bound to monomer VL11), with specificity for human and rat TNF-alpha; and VL18-3L-VL11-PEP (FIG. 10B), which is the dimer molecule fused to an albumin-binding domain (PEP) that extends half-life.
Figure 10B:

As a further measure of therapeutic effect, the changes in hind ankle swelling were assessed for rats with induced arthritis during a 20-day period of treatment. Clinical severity was assessed by quantification of hind-ankle swelling, which was obtained by measurement of the perimeter of the hind ankles with a dial-guage caliper. Day 4 corresponds to the first day that clinical arthritis was observed and day 20, the final day of treatment. "PBS control" corresponds to an AIA set of animals injected with vehicle. Last set of columns corresponds to a healthy animal (C−). VL18-3L-VL11 and VL18-3L-VL11-PEP produced significant results. Results are mean values+/−S.D. and are illustrated in FIG. 7.

Hind limbs of the animals were photographed to illustrate the changes in hind ankle swelling observed on day 20 (the final day of treatment). The photographs were compared to that of a healthy rat. Photographs are illustrated in FIGS. 8A-E.

For histopathological observation, paw samples were collected at the time of sacrifice (day 20). Samples were fixed immediately in 10% neutral buffered formalin solution, after being fixed, samples also were decalcified in 10% formic acid and then dehydrated using increased ethanol concentrations (70%, 96%, and 100%). Samples were next embedded in paraffin, sectioned using Microtome (Leica R M 2145, Germany) and stained with hematoxylin and eosin for morphological examination. Images were acquired using a Leica DM 2500 (Leica microsystems, Germany) microscope equipped with a colour camera. Histograms were prepared from joints of AIA rats treated with VL18-3L-VL11, VL18-3L-VL11-PEP, PBS, or dexamethasone.

A massive influx of inflammatory cells, synovial hyperplasia, and accumulation of abundant monomorphonuclear and polymorphonuclear cells in the joint space of AIA rats given saline (PBS) were evident compared with the normal control rats. By comparison, rats treated over 20 days with 100 µg VL18-3L-VL11 or VL18-3L-VL11-PEP, like the ones treated with dexamethasone, revealed an obvious reduction in inflammation and joint destruction in the four limbs, to the extent that the synovial membranes in the joints of treated animals were almost like those from normal animals. Significant results were obtained using VL18-3L-VL11 and VL18-3L-VL11-PEP. FIGS. 9C-F illustrates results from the AIA and control rats, treated with VL18-3L-VL11, VL18-3L-VL11-PEP, PBS, or dexamethasone.

Example 9

De-Immunization of VL18-3L-VL11 and VL18-3L-VL11-PEP

An in silico assessment (Algonomics Epibase™— LONZA) against human T cell epitopes was carried out as a de-immunizing strategy of VL18-3L-VL11 and VL18-3L-VL11-PEP, to reduce $T_H$ epitope content. To recap, VL18-3L-VL11 is a recombinant single domain antibody fragment (sdAb) in dimeric form (monomer VL18 bound to monomer VL11), with specificity for human and rat TNF-alpha; VL18-3L-VL11-PEP is the VL18-3L-VL11 dimer molecule fused to an albumin binding domain (PEP) that extends half-life. See FIGS. 10A-B.

Figures 11A, 11B:
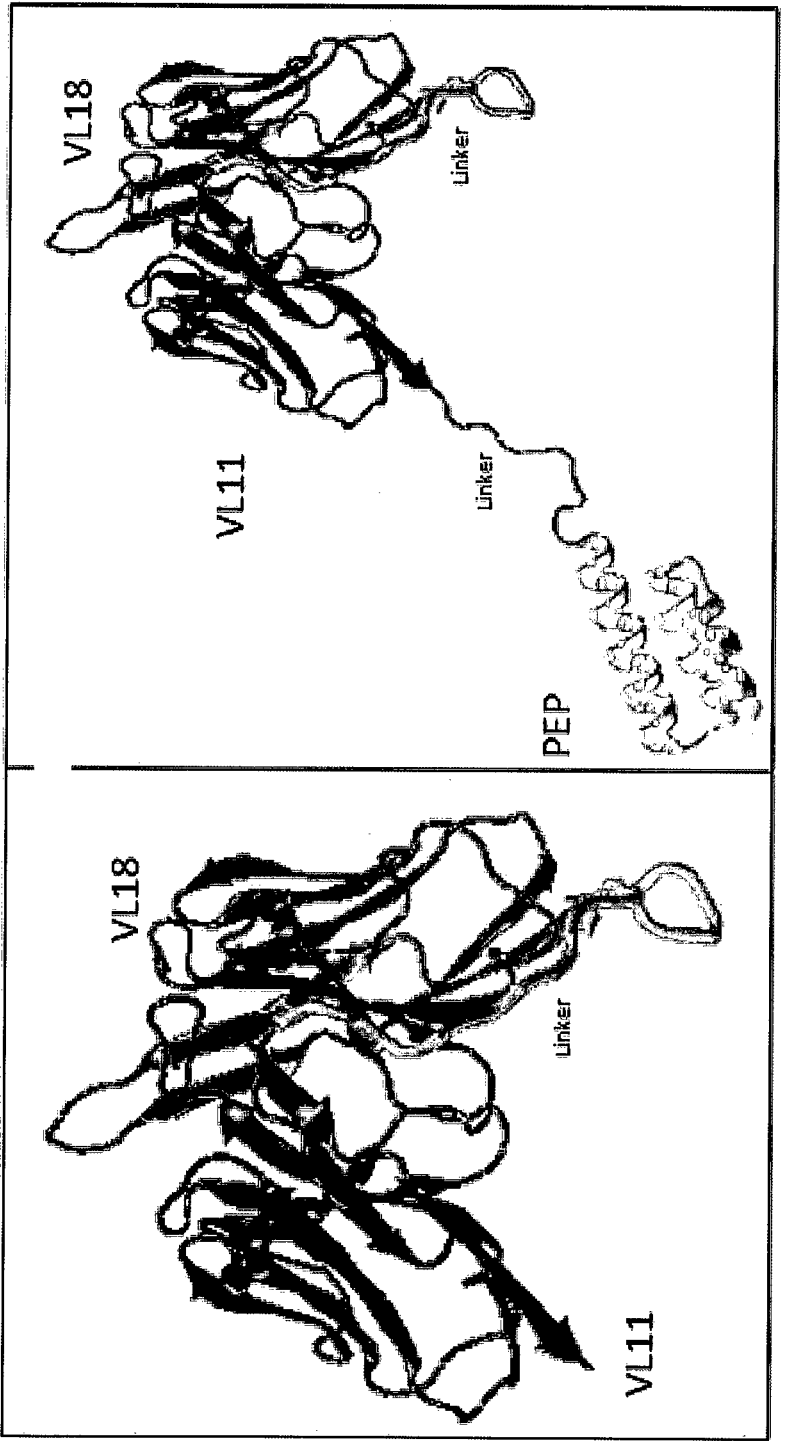
FIGS. 11A-B illustrate 3D models for the VL18-3L-VL11 and VL18-3L-VL11-PEP molecules.

3D models of VL18-3L-VL11 and VL18-3L-VL11-PEP were developed using Tripole modelling tools (LONZA). FIG. 11 illustrates 3D models for the VL18-3L-VL11 and VL18-3L-VL11-PEP molecules.

Based on the results of the profiling and positioning of putative T-cell epitopes, a list of amino acid substitutions was identified:

Proposed Amino Acid Substitutions

In the summary listing below, the double mutants are linked by a hyphen, e.g. A51V-L54R, and variant substitutions involving the same position is given within brackets, separated by a slash, e.g. (A51V-L54R/A51V-L54E). In addition, two solvent-exposed framework cysteine to serine mutations were proposed to increase stability.

In VL18: T7Q, V15P, (A51V-L54R/A51V-L54E), K63S, E79K, (C80S), T91A, L111K (9 proposed amino acid substitutions).

In VL11: T7Q, V15P, R31S, (A51V-L54R/A51V-L54E), K63S, E79K, (C80S), T91A, A100S, and E106K (11 proposed amino acid substitutions).

In Pep: E12D, T29H-K35D, and A45D (4 proposed amino acid substitutions).

Figure 13:
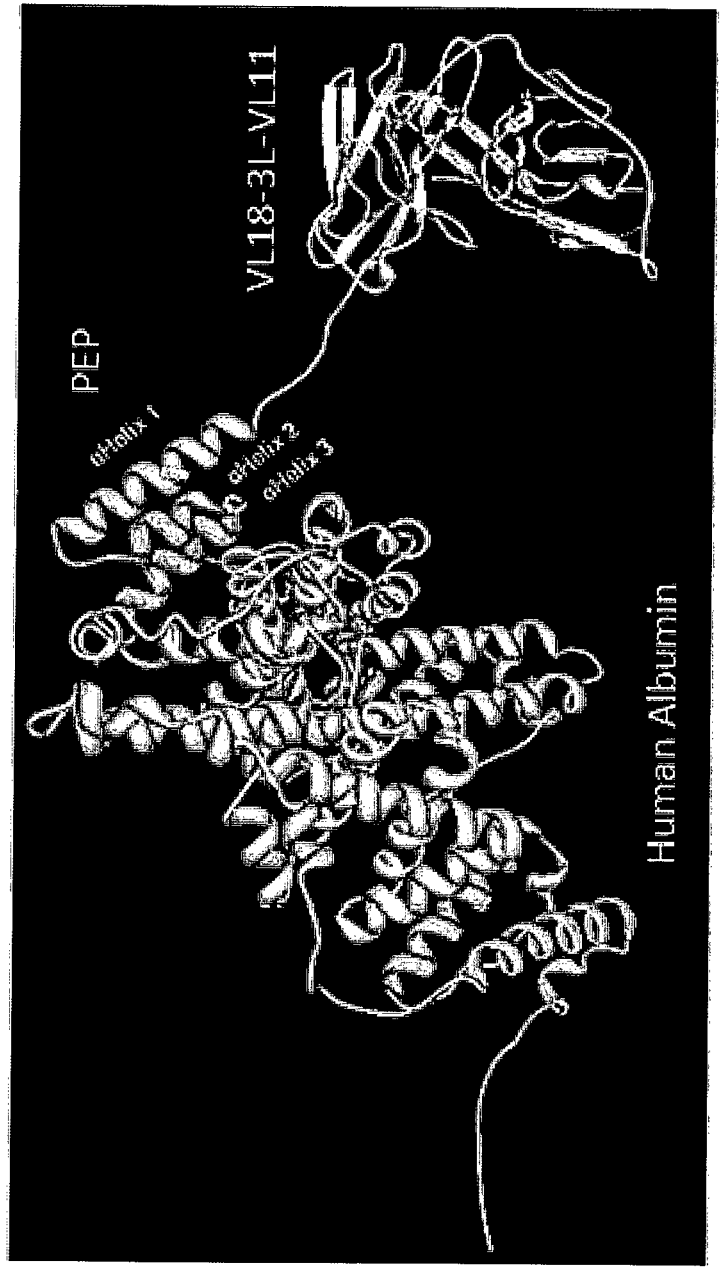
FIG. 13 illustrates the mode of binding between a VL-VL-PEP construct of the invention and human albumin.

Sequences of VL18, VL11 and PEP domains containing the substitutions are presented in FIGS. 12A-C, respectively. The figures show Kabat and Ordinal numbering for the various domains. CDRs are indicated by x. The proposed positions for substitutions are highlighted in gray. The mode of binding between VL18-3L-VL11-PEP and human albumin is illustrated in FIG. 13.

Example 10

Synthesis of De-Immunized VL18-3L-VL11/PEP Variants

As a result of the proposed amino acid substitutions described in Example 9, putative de-immunized variants of VL18-3L-VL11 and VL18-3L-VL11-PEP were synthesized, as shown below in Tables 2 and 3. A sequence encoding the HA-tag sequence (YPYDVPDYA (SEQ ID NO: 61)) was also added at the C-terminus. Genes encoding the de-immunized variants were cloned into the pET28a expression vector by NheI and XhoI digestion.

TABLE 2

Schema of experimental variants to test

| Variant identification | Domain substitutions | Number of substitutions introduced |
|---|---|---|
| VL18-3L-VL11 DI #1 | VL18: T7Q, V15P, (A51V-L54R), K63S, E79K, (C80S), T91A, L111K<br>VL11: T7Q, V15P, R31S, (A51V-L54R), K63S, E79K, (C80S), T91A, A100S, E106K | 20 aa substitutions |
| VL18-3L-VL11 DI #2 | VL18: T7Q, V15P, (A51V-L54E), K63S, E79K, (C80S), T91A, L111K<br>VL11: T7Q, V15P, R31S, (A51V-L54E), K63S, E79K, (C80S), T91A, A100S, E106K | 20 aa substitutions |
| VL18-3L-VL11 DI #3 | VL18: T7Q, V15P, (A51V-L54R), K63S, E79K, (C80S), L111K<br>VL11: T7Q, V15P, R31S, (A51V-L54R), K63S, E79K, (C80S), E106K | 17 aa substitutions<br>CDR3 x |
| VL18-3L-VL11 DI #4 | VL18: T7Q, V15P, (A51V-L54E), K63S, E79K, (C80S), L111K<br>VL11: T7Q, V15P, R31S, (A51V-L54E), K63S, E79K, (C80S), E106K | 17 aa substitutions<br>CDR3 x |
| VL18-3L-VL11 DI #5 | VL18: T7Q, V15P, K63S, E79K, (C80S), L111K<br>VL11: T7Q, V15P, R31S, K63S, E79K, (C80S), E106K | 13 aa substitutions<br>CDR2 x;<br>CDR3 x |
| VL18-3L-VL11 PEP #6 | VL18: WT<br>VL11: WT<br>PEP: WT | — |
| VL18-3L-VL11 PEP DI #7 | VL18: WT<br>VL11: WT<br>PEP: E12D, T29H-K35D, A45D | 4 aa substitutions |
| VL18-3L-VL11 DI #3-PEP DI #8 | VL18: T7Q, V15P, (A51V-L54R), K63S, E79K, (C80S), T91A, L111K<br>VL11: T7Q, V15P, R31S, (A51V-L54R), K63S, E79K, (C80S), T91A, A100S, E106K<br>PEP: E12D, T29H-K35D, A45D | 21 aa substitutions<br>CDR3 x |
| VL18-3L-VL11 DI #5-PEP DI #9 | VL18: T7Q, V15P, K63S, E79K, L111K<br>VL11: T7Q, V15P, R31S, K63S, E79K, (C80S), E106K<br>PEP: E12D, T29H-K35D, A45D | 17 aa substitutions<br>CDR2 x;<br>CDR3 x |

TABLE 3

Schema of experimental variants to test.

| Domain | Regions | Substitutions | 1 | 2 | 3 | 4 | 5 | 6 | 7 | 8 | 9 |
|---|---|---|---|---|---|---|---|---|---|---|---|
| VL18 | FwR1 | T7Q | X | X | X | X | X |   |   | X | X |
|   |   | V15P | X | X | X | X | X |   |   | X | X |
|   | CDR2 | A51V-L54E |   |   | X |   | X |   |   |   |   |
|   |   | A51V-L54R | X |   |   |   |   |   |   | X |   |
|   | FwR3 | K63S | X | X | X | X | X |   |   | X | X |
|   |   | E79K | X | X | X | X | X |   |   | X | X |
|   | CDR3 | T91A | X | X |   |   |   |   |   |   |   |
|   | FwR4 | L111K | X | X | X | X | X |   |   | X | X |
| VL11 | FwR1 | T7Q | X | X | X | X | X |   |   | X | X |
|   |   | V15P | X | X | X | X | X |   |   | X | X |
|   | CDR1 | R31S | X | X | X | X | X |   |   | X | X |
|   | CDR2 | A51V-L54E |   |   | X |   | X |   |   |   |   |
|   |   | A51V-L54R | X |   |   |   |   |   |   | X |   |
|   | FwR3 | K63S | X | X | X | X | X |   |   | X | X |
|   |   | E79K | X | X | X | X | X |   |   | X | X |

TABLE 3-continued

Schema of experimental variants to test.

| Domain | Regions | Substitutions | 1 | 2 | 3 | 4 | 5 | 6 | 7 | 8 | 9 |
|---|---|---|---|---|---|---|---|---|---|---|---|
|   | CDR3 | T91A | X | X |   |   |   |   |   |   |   |
|   |   | A100S | X | X |   |   |   |   |   |   |   |
|   | FwR4 | E106K | X | X | X | X | X |   |   | X | X |
| PEP |   | E12D |   |   |   |   |   |   | X | X | X |
|   |   | T29H-K35D |   |   |   |   |   |   | X | X | X |
|   |   | A45D |   |   |   |   |   |   | X | X | X |
| Extra |   | C80S | X | X | X | X | X |   |   | X | X |
|   |   | C210S | X | X | X | X | X |   |   | X | X |

Variant #6 is the wiltd-type VL18-3L-VL11-PEP and variant #7 is the wild-type VL18-3L-VL11 fused to the de-immunized Pep.

The de-immunized variants were tested in expression studies, antigen cross-reactivity, affinity measurements, and efficacy studies in the cytotoxicity assay with L929 cell line as described in the Examples above. Results for a representative number of variants are presented below in Table 4.

TABLE 4

Schema of results obtained for tested variants.

| Variant # | Expression Yields (mg/L) | Antigen Cross-Reactivity | Affinity (Biacore) | Efficacy Cell Assay | Efficacy RA rat model |
|---|---|---|---|---|---|
| VL18-3L-VL11 | 6-8 | Human and rat TNF | 0.7 nM (human TNF) | High | High |
| VL18-3L-VL11 DI #1 | 6-8 | Human and rat TNF | ND | Low | — |
| VL18-3L-VL11 DI #2 | <0.2 | ND | ND | — | — |
| VL18-3L-VL11 DI #3 | 6-8 | Human and rat TNF | 0.7 nM (human TNF) | High | High |
| VL18-3L-VL11 DI #4 | <0.2 | ND | ND | — | — |
| VL18-3L-VL11 DI #5 | 6-8 | Human and rat TNF | 0.8 nM (human TNF) | High | High |
| VL18-3L-VL11 PEP #6 | 12-15 | Human and rat TNF (VL18-3L-VL11) Human, rat, and mouse Albumin (Pep) | 0.8 nM (human TNF) 4.7 nM (human albumin) 0.4 nM (rat albumin) 42.1 (mouse albumin) | High | High |
| VL18-3L-VL11 PEP DI #7 | 12-15 | Human and rat TNF (VL18-3L-VL11) Human, rat, and mouse Albumin (Pep DI) | 0.7 nM (human TNF) 61.8 nM (human albumin) 28.1 nM (rat albumin) NC (mouse albumin) | High | High |
| VL18-3L-VL11 DI3-PEP DI #8 | 6-8 | Human and rat TNF (VL18-3L-VL11-DI3) Human, rat, and mouse Albumin (Pep DI) | 0.6 nM (human TNF) 88.5 nM (human albumin) 22.4 nM (rat albumin) NC (mouse albumin) | High | High |

TABLE 4-continued

Schema of results obtained for tested variants.

| Variant # | Expression Yields (mg/L) | Antigen Cross-Reactivity | Affinity (Biacore) | Efficacy Cell Assay | Efficacy RA rat model |
|---|---|---|---|---|---|
| VL18-3L-VL11 DI5-PEP DI #9 | 12-15 | Human and rat TNF (VL18-3L-VL11DI5) Human, rat, and mouse Albumin (Pep DI) | 0.4 nM (human TNF) 92 nM (human albumin) 32 nM (rat albumin) NC (mouse albumin) | High | High |

ND - Values could not be determined due to the low affinity of the interaction

Example 11

Large Scale Expression of De-Immunized VL Dimers and Fusions Thereof

An expression construct designed to express a recombinant anti-TNF-alpha polypeptide of the invention (without His Tag) in bacteria was used to transform *E. coli* Tuner(DE3), *E. coli* BLR (DE3), and/or DL21 (DE3) to generate clones for expression screening. Induction experiments (0.1 mM IPTG, 18 hrs) were performed on three colonies. SDS-PAGE or immunoblot were run to compare protein expression (total and soluble) and the best expresser banked and then utilized for production first at the 15 L scale followed by a scale-up production at 100 L. Growth and induction were performed as follows. Briefly, cells from a fresh culture were grown at 37° C. in SB medium plus a selection agent to an OD between 0.7 and 0.9, the temperature was dropped to 18° C., and the culture induced with 0.1 mM IPTG. After an overnight exposure, the cell paste was harvested by centrifugation and stored at −20° C. until purification. Either an SDS-PAGE or a Western-immunoblot (using an antigen specific antibody) was performed on an analytical sample to confirm protein expression. Experiments were conducted in conjunction with Paragon (USA).

Figure 14:
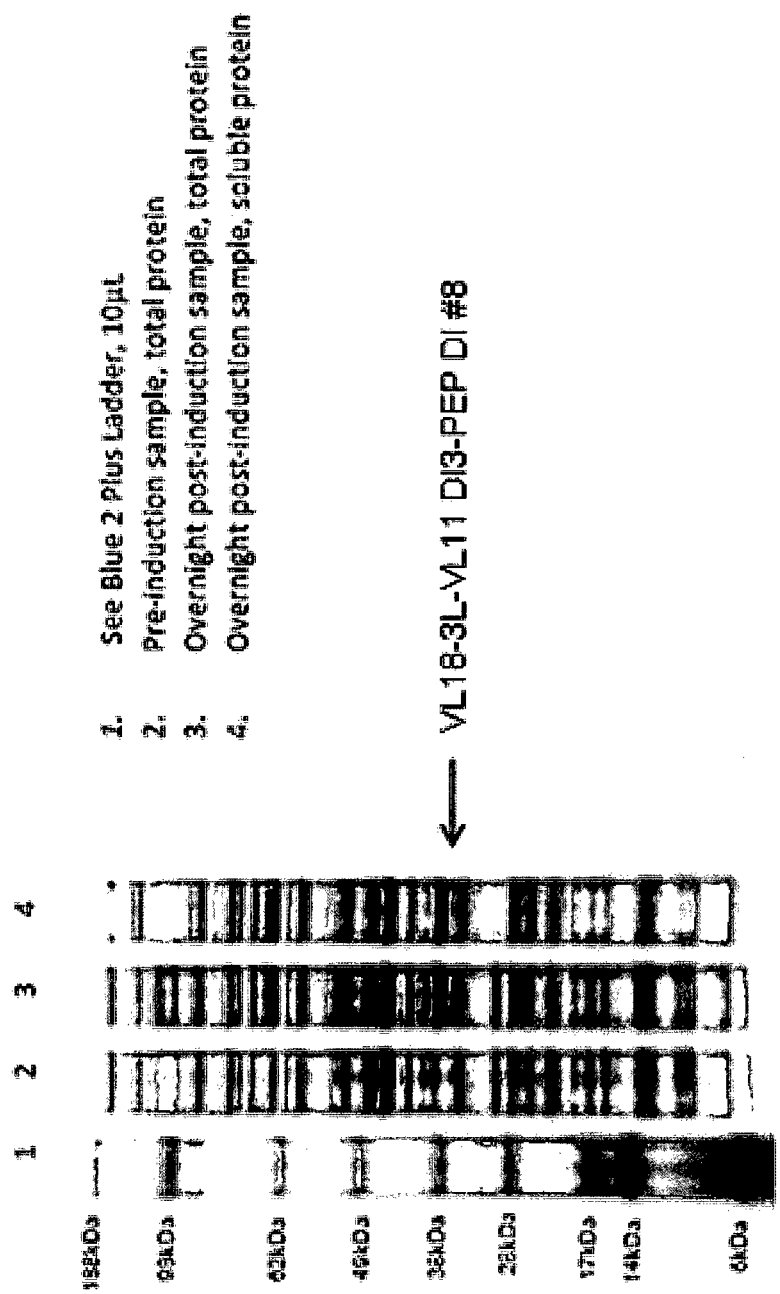
FIG. 14 illustrates results of Coomassie Blue SDS-PAGE expression analysis of a recombinant de-immunized VL-VL dimer of the invention (VL18-3L-VL11 DI3-PEP DI #8). The gel position of the expressed dimer is indicated by the arrow. Lanes 1-4 represent the following: Lane 1: See Blue 2 Plus Ladder, 10 μL; Lane 2: Pre-induction sample, total protein; Lane 3: overnight post-induction sample, total protein; and Lane 4: overnight post-induction sample, soluble protein.

Results of Coomassie Blue SDS-PAGE expression analysis of the recombinant dimer VL18-3L-VL11 DI3-PEP DI #8 are illustrated in FIG. 14. The position in the gel of the expressed dimer is indicated by the arrow. Expression yields for anti-TNF-alpha polypeptides of the invention and for de-immunized variants thereof are provided in Tables 5 and 6 below.

TABLE 5

Anti-TNF antibody fragments expressions yields.

| Clone # | Induction time | Yield (mg/L) |
|---|---|---|
| VL18 | ON/18° C. | 3-6 |
| VL11 | ON/18° C. | 3-6 |
| VL18-3L-VL18 | ON/18° C. | 6-8 |
| VL18-3L-VL11 | ON/18° C. | 6-8 |
| VL11-3L-VL11 | ON/18ᵃ C. | 6-8 |
| VL11-3L-VL18 | ON/18° C. | 6-8 |

TABLE 6

Anti-TNF de-immunized variants expressions yields

| Clone # | Induction time | Yield (mg/L) |
|---|---|---|
| VL18-3L-VL11 | ON/18° C. | 6-8 |
| VL18-3L-VL11 DI #1 | ON/18° C. | 6-8 |
| VL18-3L-VL11 DI #2 | ON/18° C. | <0.2 |
| VL18-3L-VL11 DI #3 | ON/18° C. | 6-8 |
| VL18-3L-VL11 DI #4 | ON/18ᵃ C. | <0.2 |
| VL18-3L-VL11 DI #5 | ON/18° C. | 6-8 |
| VL18-3L-VL11 PEP | ON/18° C. | 12-15 |
| VL18-3L-VL11 PEP DI | ON/18° C. | 12-15 |
| VL18-3L-VL11-DI3-PEP DI | ON/18ᵃ C. | 6-8 |
| VL18-3L-VL11-DI5-PEP DI | ON/18° C. | 6-8 |

Example 12

Purification of De-Immunized VL Dimers and Fusions Thereof

The recombinantly expressed anti-TNF-alpha polypeptides of Example 11 were purified using Protein L and/or human albumin affinity chromatography standard procedures. Briefly, cell paste was resuspended in PBS buffer supplemented with anti-proteases using a polytron at medium speed. Suspension was lysed using a homogenizer, and soluble material clarified by centrifugation. Clarified lysate was loaded onto a chromatography column containing Protein L and/or human albumin resin. The resin was washed to remove contaminating proteins and endotoxin, and the bound polypeptide eluted using 100 mM Glycine (pH=3). Fractions containing the polypeptide of interest were pooled and processed for residual endotoxin removal (ActiClean Etox).

Figure 15A:
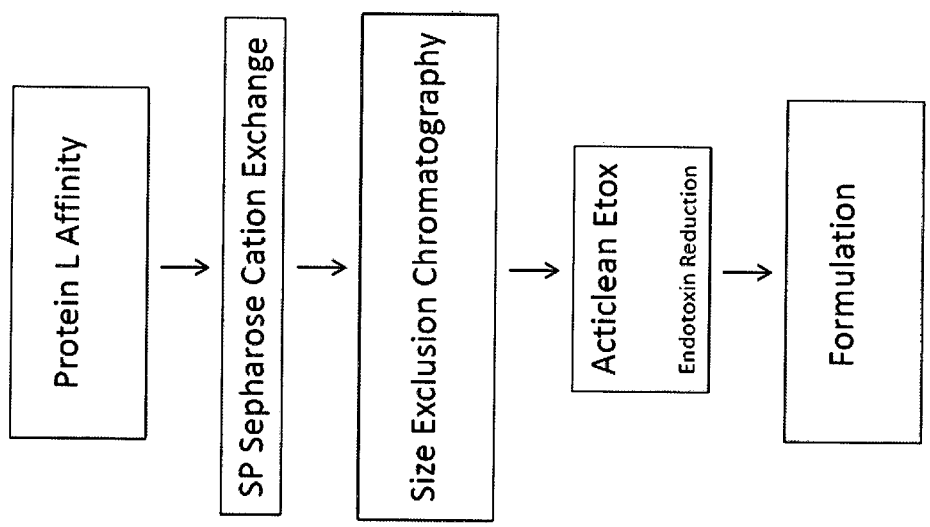
FIGS. 15A-E illustrate downstream process development for de-immunized VL-VL dimers of the invention.
Figure 15C:
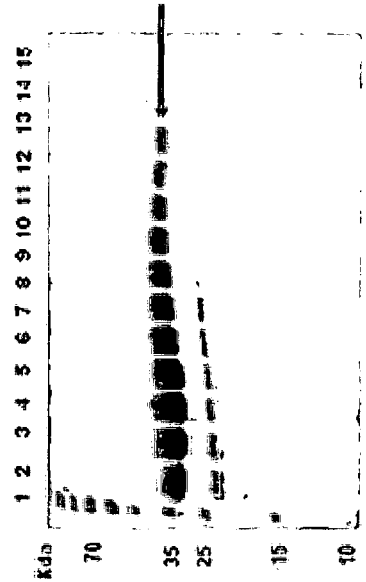
Figure 15B:
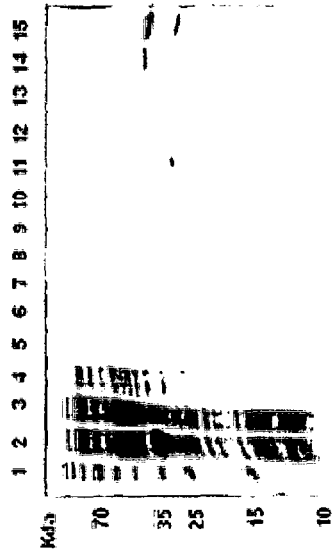
Figure 15D:
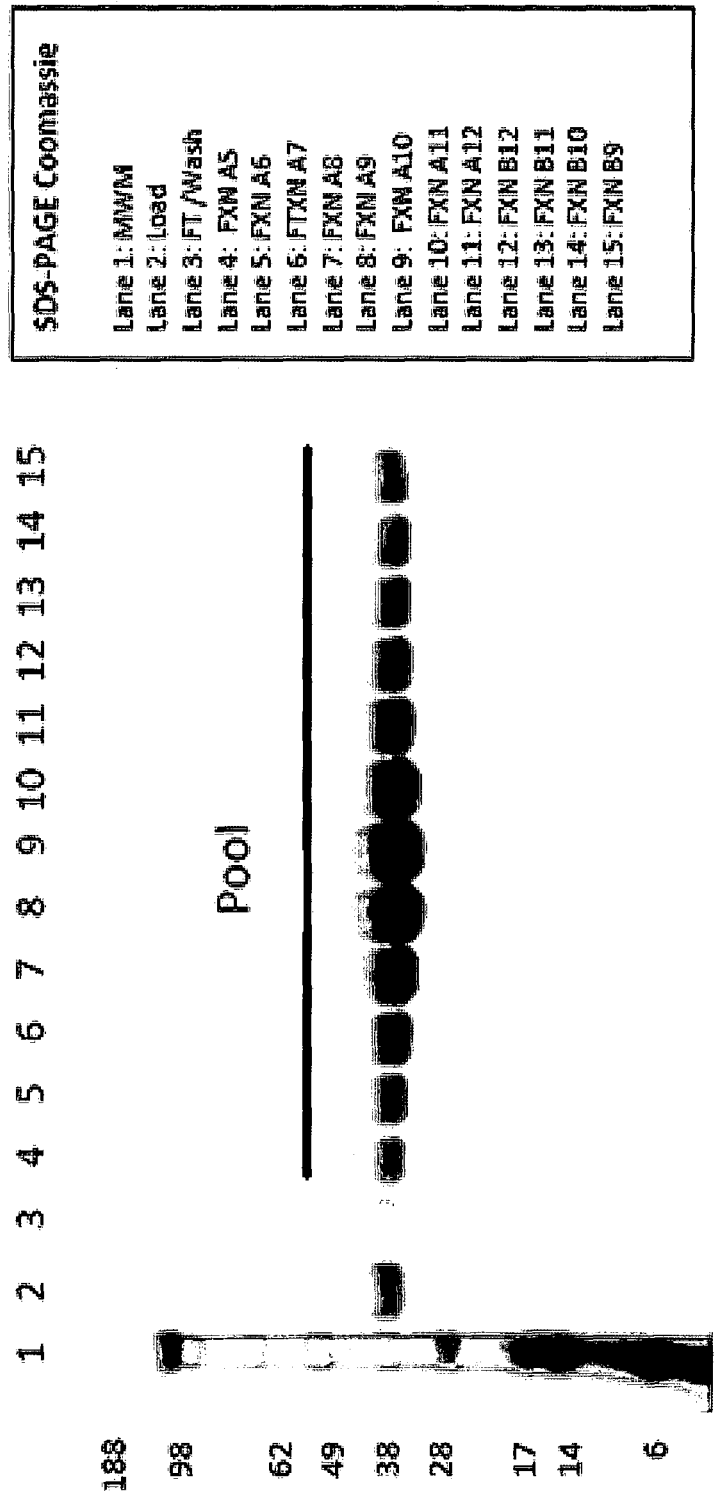
Figure 15E:
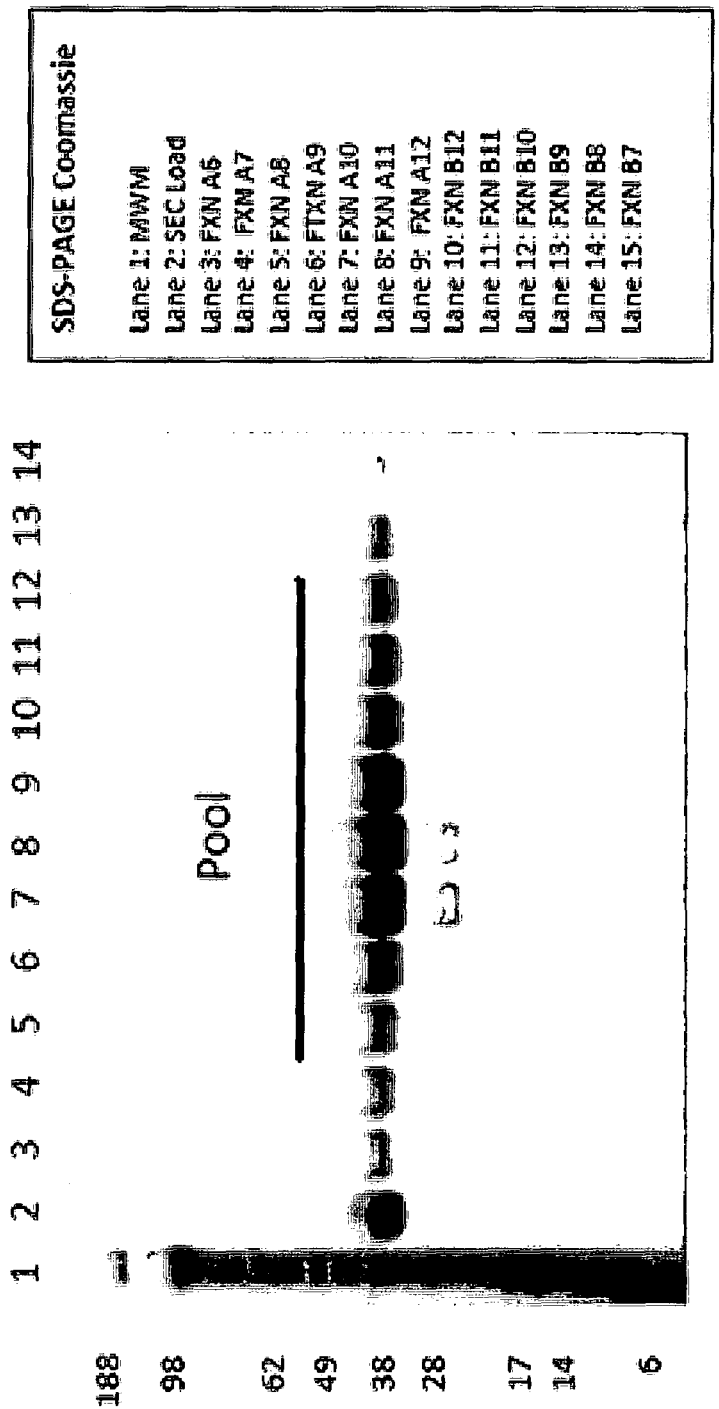

Additional polishing steps may be performed to meet desired purity specifications, with the type of polishing step implemented (e.g. IEX, SEC) to be determined following analysis of the contaminants. Steps included SP Sepharose cation exchange; size exclusion chromatography, and endotoxin reduction, followed by formulation. The downstream process development for the de-immunized dimer VL18-3L-VL11 DI3-PEP DI #8 is illustrated in FIGS. 15A-E. A schematic representation of the downstream process development is illustrated in FIG. 15A. Results of Coomassie Blue SDS-PAGE expression analysis following Protein L Affinity purification of the de-immunized dimer VL18-3L-VL11 DI3-PEP DI #8 is illustrated in FIGS. 15B-C. The results of Coomassie Blue SDS-PAGE expression analysis following SP Sheparose cation exchange chromatography of the de-immunized dimer VL18-3L-VL11 DI3-PEP DI #8 is illustrated in FIG. 15D. The results of Coomassie Blue SDS-PAGE expression analysis following size exclusion chromatography of the de-immunized dimer VL18-3L-VL11 DI3-PEP DI #8 is illustrated in FIG. 15E.

The final purified polypeptide was dialyzed into PBS buffer, concentrated to ~5 mg/ml, and stored frozen at −80° C. All steps of the purification were monitored by SDS-PAGE-Coomassie and A280 absorbance. Purified polypeptides were accompanied with a specifications sheet documenting purity (SDS-PAGE-coomassie), yield (Bradford assay or A280), endotoxin (PTS EndoSafe assay) and identity (Western blot-antibody). Experiments were conducted in conjunction with Paragon (USA).

Example 13a

Therapeutic Effects of De-Immunized VL18-3L-VL11/PEP Variants

To determine therapeutic effects of de-immunized VL18-3L-VL11 and VL18-3L-VL11-PEP variants, an established rat-adjuvant induced arthritis model (AIA) was used, as described above. Wistar female rats (Charles River) received an injection of Freund's complete adjuvant (FCA) (1 mg/ml) intradermally (i.d.). The rats were treated with 100 µg VL18-3L-VL11 and VL18-3L-VL11-PEP, as well as two de-immunized variants of each (VL18-3L-VL11 DI #3 and DI #5; VL18-3L-VL11-DI #3-PEP DI and VL18-3L-VL11-DI #5-PEP DI). VL18-3L-VL11 and the two de-immunized variants were administered daily. VL18-3L-VL11-PEP and the two PEP fusion de-immunized variants were administered at 2 day intervals. Dexamethasone and PBS were used again as controls.

Figure 16:
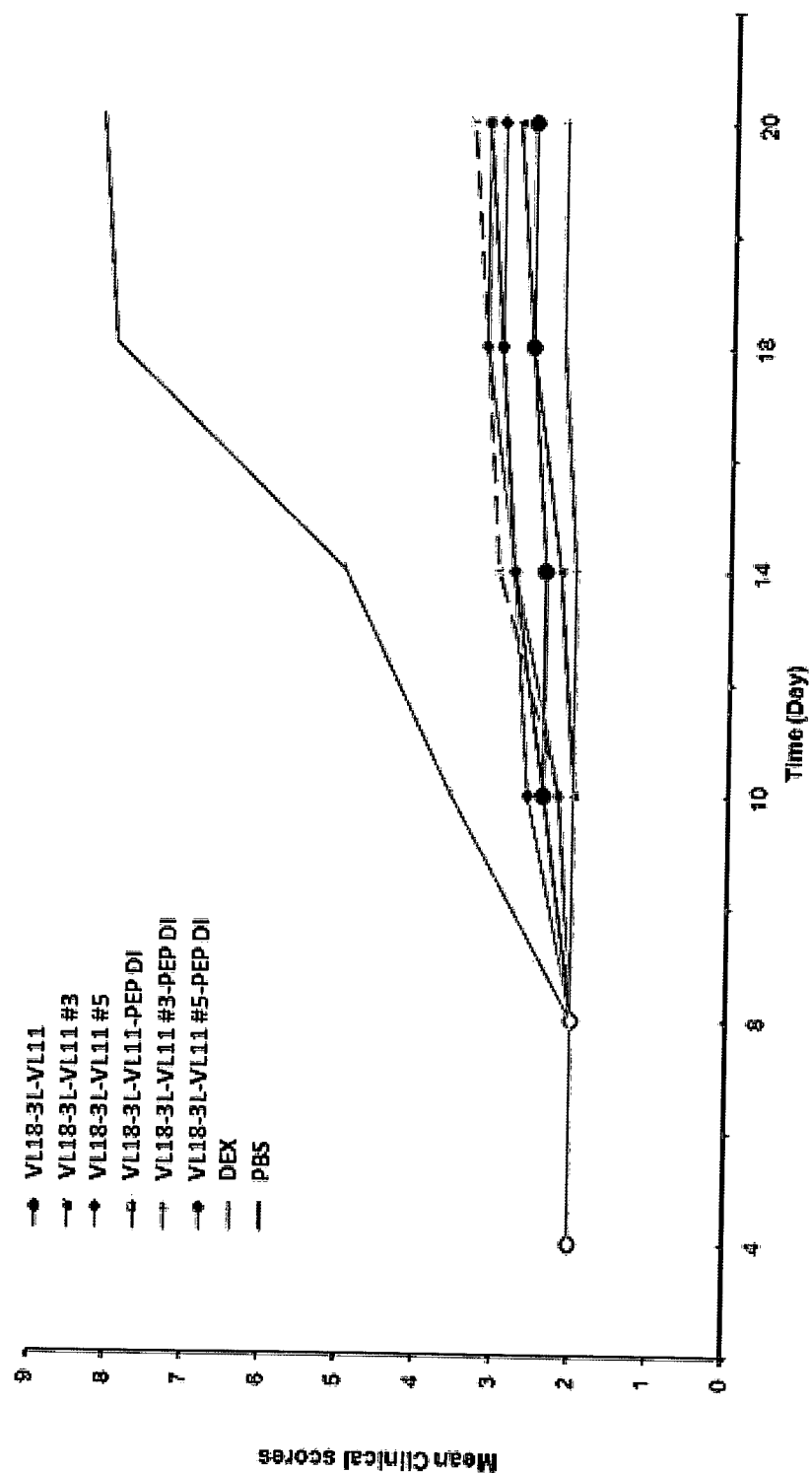
FIG. 16 illustrates therapeutic effect of de-immunized VL-VL dimer of the invention in an established rat adjuvant induced arthritis model (AIA).
Figures 17G, 17H, 17I:
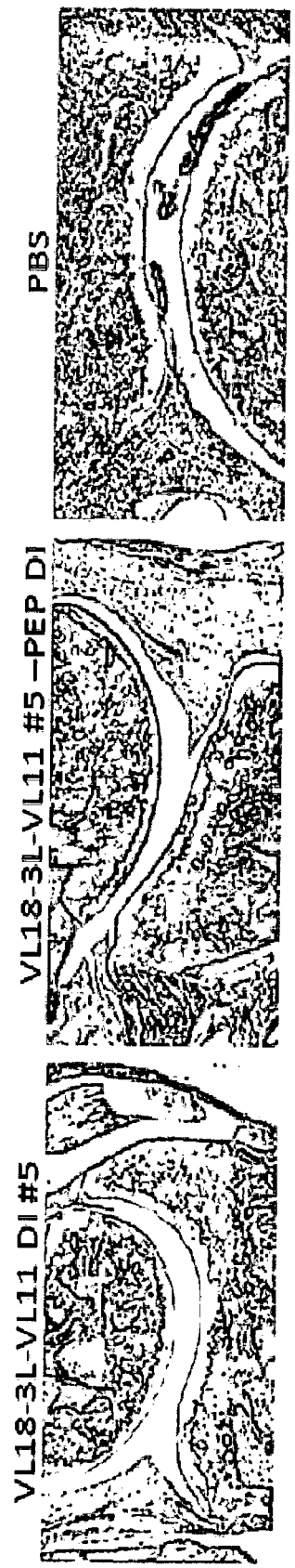

As described above, the severity of arthritis was assessed after disease induction based on clinical scores (limb analysis), ankle joint measurement, and histological analysis, providing arthritis severity scores in rats (n=6) during a 20-day period of treatment. As compared to the negative control (PBS), rats treated with de-immunized VL18-3L-VL11 and VL18-3L-VL11-PEP variants, like the ones treated with the wild-type VL-18-3L-VL11/PEP and dexamethasone, revealed an obvious reduction in inflammation and joint destruction in the four limbs. Results are illustrated in FIG. 16.

For histopathological observation, paw samples were collected at the time of sacrifice (day 20). Samples were fixed immediately in 10% neutral buffered formalin solution, after being fixed, samples also were decalcified in 10% formic acid and then dehydrated using increased ethanol concentrations (70%, 96%, and 100%). Samples were next embedded in paraffin, sectioned using Microtome (Leica RM 2145, Germany) and stained with hematoxylin and eosin for morphological examination. Images were acquired using a Leica DM 2500 (Leica microsystems, Germany) microscope equipped with a colour camera. Histograms were prepared from joints of AIA rats treated with VL18-3L-VL11, VL18-3L-PEP, or PBS or dexamethasone. Results are illustrated in FIGS. 17A-I.

Example 13b

Therapeutic Effects of De-Immunized VL18-3L-VL11/PEP Variants in Prevention of Chronic Polyarthriths To determine efficacy effects of de-immunized VL18-3L-VL11-PEP variants in preventing the development of arthritis, a transgenic mouse (Tg197) model is used. The Tg197 model of arthritis is a humanized TNF transgenic mouse model with human TNF deregulated expression resulting in the spontaneous development of arthritis pathology closely resembling that of the human rheumatoid arthritis (Keffer et al. 1991).

The experimental study with Tg197 involves: 4 groups of 8 mice, including a negative control, a positive control (Remicade™) and test treated groups (VL18-3L-VL11-PEP variants) Another 4 mice are sacrificed at the beginning of the study to serve as controls for histopathology. A 7 week prophylactic treatment is performed from week 3 to week 10. Administration of the anti-TNF-α antibodies, and fusions thereof with de-immunized PEP, are made twice weekly at a final dose of 10 mg/kg by intraperitoneal injection. During the 7 week treatment period clinical scores are recorded by observing macroscopic changes in joint morphology for each animal. At 10 weeks of age, all animals are sacrificed and joints and sera are collected. Sera are stored at −70° C. and ankle joints in formalin Ankle joint sections are embedded in paraffin, sectioned and then subsequently used for histopathological evaluation of disease progression.

Example 14a

Pharmacokinetics of De-Immunized VL Dimers and Fusions Thereof

To determine in vivo the plasma-time course and tissue distribution of anti-TNF-alpha polypeptides according to the invention, a pharmacokinetic study is performed in rats. Rats are administered a single subcutaneous or intravenous (SC/IV) dose of $^{14}C$-labeled anti-TNF-alpha polypeptide. The radiolabeled polypeptide is prepared at the start date or one day prior to the start date; the radiochemical concentration is analyzed pre- and post-dose; and stability is evaluated over the dosing interval by radiochemical HPLC analysis. The study design is as outlined in Table 7 below:

TABLE 7

| | STUDY DESIGN: | | | | |
|---|---|---|---|---|---|
| Group & Route | No. Animals & Sex | Dose Volume (mL/kg) | Dose Conc. (mg/kg) | Dose Radioactivity (µCi/kg) | Samples Collected |
| 1 SC/IV | 6M (2 cohorts of 3) | TBD | TBD | ~100 | Blood, Plasma |
| 2 SC/IV | 6M | TBD | TBD | ~100 | Tissues, Residual Carcasses |

The rats are observed twice daily for mortality and signs of ill health or adverse reaction to the treatment. For Group 1, samples are collected from cohort bleeds as follows: about 0.5 mL of blood or plasma is collected from three animals per time point, including pre-dose, and 1, 2, 4, 8, 12, 24, 48, 72, 96, 120 and 168 hours post-dose. For Group 2, samples are collected as follows: tissues are collected from one animal per time point, at 1, 4, 8, 24, 72 and 168 hours post-dose. Tissues included are: adrenal gland, bladder (urinary), bone, bone marrow, brain, eyes (both), fat (brown), fat (white), heart, kidneys, large intestine/cecum, liver, lung, lymph nodes (mesenteric), muscle, pancreas, prostate, salivary glands, skin, small intestine, spleen, stomach, testes, thymus, thyroid, and residual carcass.

Radioactivity levels in plasma, tissues, and residual carcasses is measured in accordance with known procedures.

Aliquots of tissue homogenates are oxidized or solubilized before analysis, while other samples are analyzed directly by mixing aliquots with scintillation fluid. Total recovery of dosed radioactivity and recovery at each interval is determined for samples from tissues and carcasses. Tissue distribution is analyzed via individual tissues obtained at necropsy. A pharmacokinetic plasma curve is generated to provide in vivo plasma-time course and tissue distribution of anti-TNF-alpha polypeptides of the invention.

Example 14b

Biodistribution of De-Immunized VL Fusions with PEP Variants

To determine in vivo the plasma-time course and tissue distribution of fusions with PEP variants according to the invention, a preliminary biodistribution assay was performed in rats, using $^{99m}Tc(CO_3)$-labelling, as follows:

Preparation of $^{99m}Tc(I)$ Tricarbonyl Precursor

Into a vial of IsoLin Kit (Covidien), $^{99m}TcO_4^-$/saline (2 ml, ~25 mCi) was added. The mixture was heated for 30 minutes and the pH of the resultant solution was adjusted to 7.4. The radiochemical purity of $[^{99m}Tc(CO)_3(H_2O)_3]^+$ was checked by RP-HPLC and instant thin-layer chromatography (ITLC) using 6 N HCl (5%) in MeOH as eluent ($R_f$≈1).
Labeling of fac-$[^{99m}Tc(CO)_3]$-Constructs The constructs were buffered with 50 mM NaH2PO4, 300 mM NaCl pH 6.0 and concentrated to ~0.5 mg/ml. Compounds fac-[99mTc(CO)3]-VL18-3L-VL11, fac-[99m Tc(CO) 3]-VL18-3L-VL11-PEP, and fac-[99mTc(CO)3]-His6-VL18-3L-VL11-DI#3-PEP #8 ("His6" disclosed as SEQ ID NO: 60) were obtained in 0.125 mg/mL final concentration, by reacting the constructs with fac-[99mTc(CO) 3(H2O)3]+. Briefly, a solution of fac-[99mTc(CO)3(H2O) 3]+ containing 2% of SDS surfactant was added to a microcentrifuge tube containing the constructs. The mixture reacted at 37° C. for 1 hour and the radiochemical purity of the 99mTc-radiolabeled construct was checked by ITLC (Rf=0; radiochemical yield ~80-95%). Unreacted free "99mTc(CO) 3" was removed by desalting using a Sephadex G-25 column eluted with 50 mM NaH2PO4, 300 mM NaCl pH 6.0.
Partition Coefficient Determination The partition coefficient was evaluated by the "shake-flask" method. The radioactive constructs were added to a mixture of octanol (1 mL) and 0.1 M PBS pH 7.4 (1 mL), which had been previously saturated with each other by stirring. This mixture was vortexed and centrifuged (3000 rpm, 10 min) to allow phase separation.

Aliquots of both octanol and PBS were counted in a γ-counter. The partition coefficient ($P_{o/w}$) was calculated by dividing the counts in the octanol phase by those in the buffer, and the results were expressed as log $P_{o/w}$±SD.
In Vitro Stability Determination The $^{99m}$Tc-radiolabeled constructs were stored in buffer solution at 37° C. for 24 h. After incubation, the solutions were analyzed by ITLC. No release of $[^{99m}Tc(CO)_3(H_2O)_3]^+$ was observed.
Biodistribution Studies In vivo evaluation studies of the radiolabeled constructs were performed in Wistar female rats (Charles River) at 15 min, 1 h, 3 h, 6 h, and 24 h. All animal experiments were performed in accordance with the guidelines of the institutional animal ethics committee. Animals were injected intraperitoneally under light isofluorane anaesthesia with the radiolabeled compounds (~1 mCi; ~300 µL; ~16-20 µg of $^{99m}Tc(CO)_3$-labeled constructs) and sacrificed by excess anaesthesia.

Figure 18A:
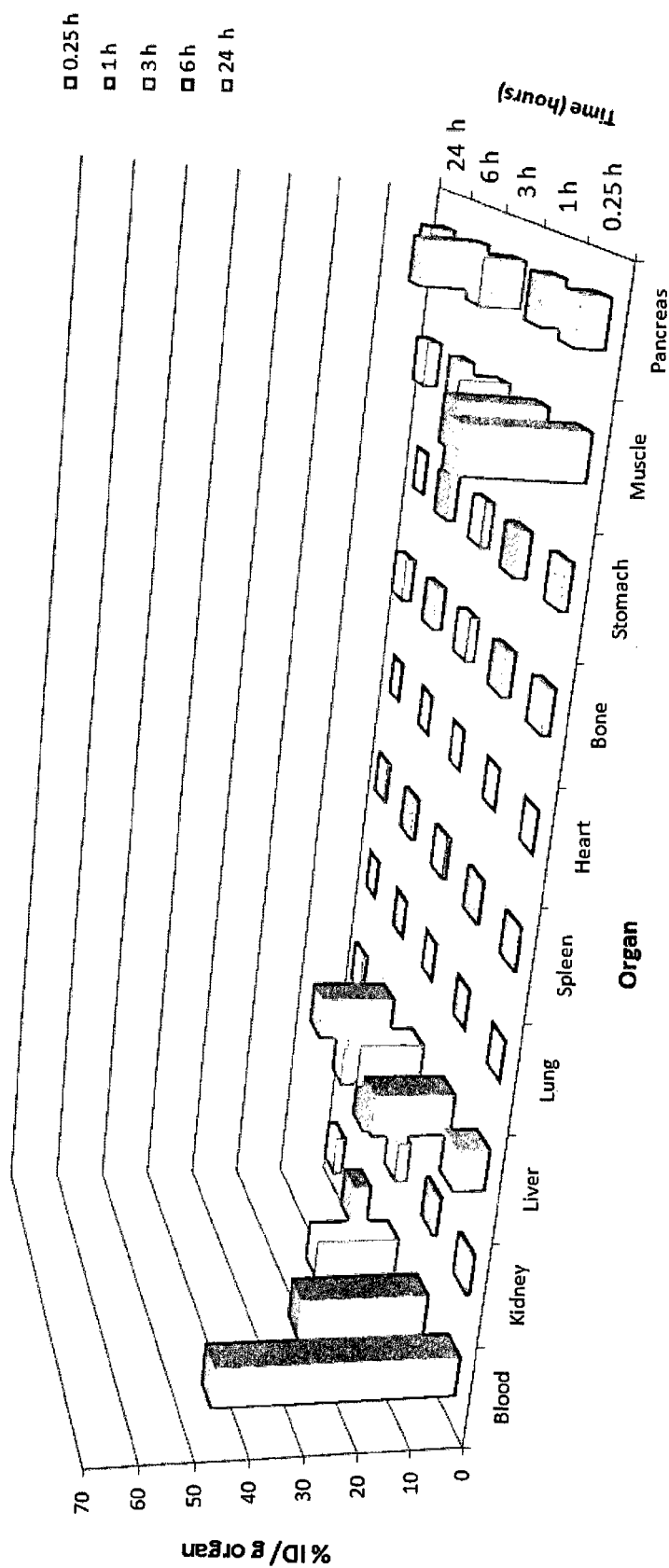
FIGS. 18A-B illustrate biodistribution data for fac-$[^{99m}Tc(CO)_3]$-VL18-3L-VL11 (FIG. 18A) and fac-$[^{99m}Tc(CO)_3]$-VL18-3L-VL11-PEP (FIG. 18B) in relevant organs, expressed as % ID/Organ for 15 min, 1 h, 3 h, 6 h, and 24 h after i.p. administration in Wistar rats (n=3).
Figure 18B:
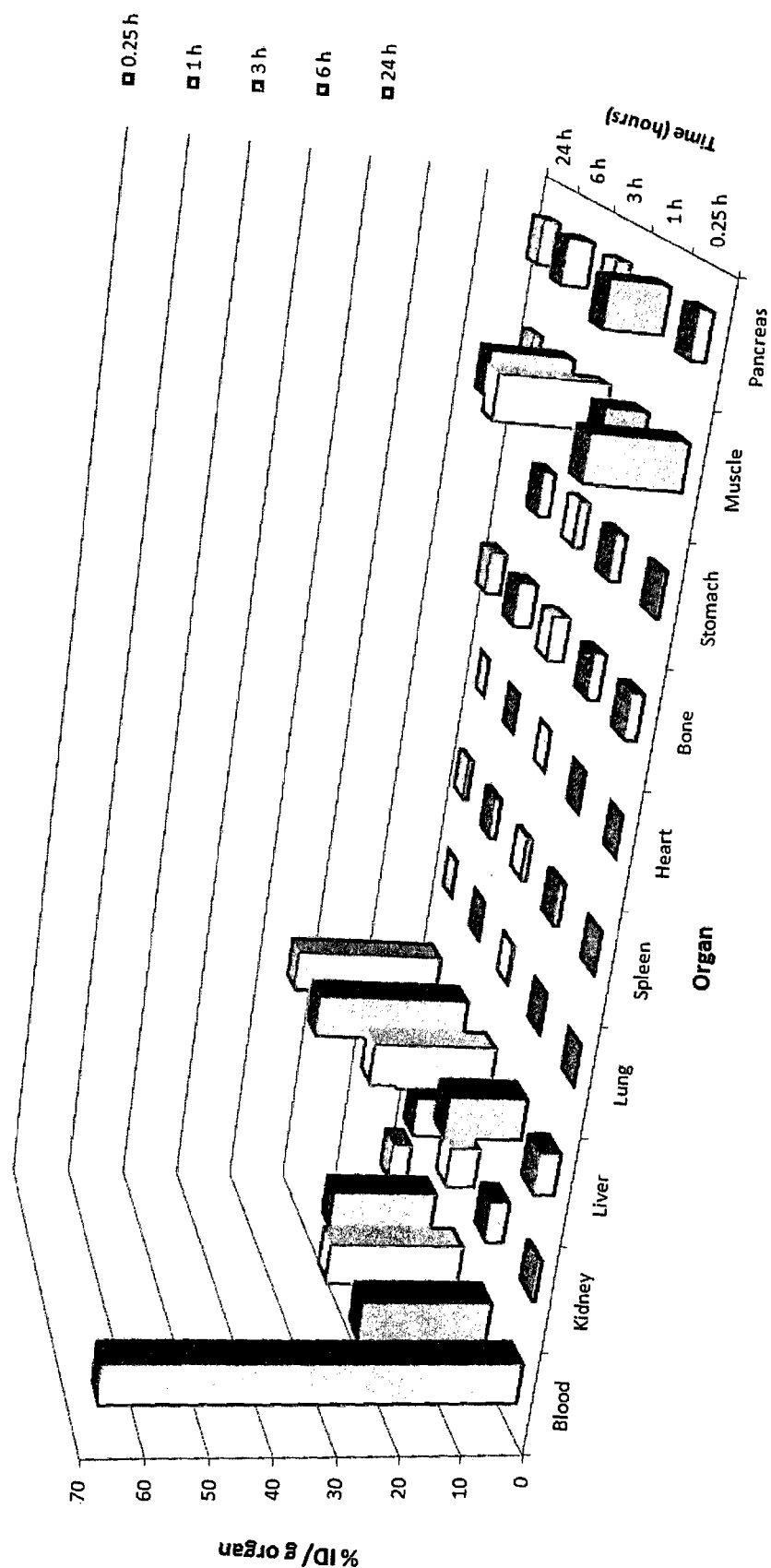

The radioactivity in the sacrificed animals was measured using a dose calibrator (Curiemeter IGC-3, Aloka, Tokyo, Japan or Carpintec CRC-15W, Ramsey, USA). The difference between the radioactivity in the injected animals and that in the killed animals was assumed to be due to excretion. Tissues of interest were dissected, rinsed to remove excess blood, weighed, and their radioactivity measured using a γ-counter (LB2111, Berthold, Germany). The uptake for most relevant organs, including each of blood, bone, and muscle tissues, was estimated assuming that these organs constitute 6, 10, and 40% of the total body weight of the animal, respectively. Results were expressed as % ID/Organ for 15 min, 1 h, 3 h, 6 h, and 24 h after i.p. administration in Wistar rats (n=3). Urine also was collected and pooled together at the time the animals were killed. Results are illustrated in FIGS. 18A-B for fac-[$^{99m}$Tc(CO)$_3$]-VL18-3L-VL11 (FIG. 18A) and fac-[$^{99m}$ Tc(CO)$_3$]-VL18-3L-VL11-PEP (FIG. 18B).

Example 15

Toxicity Study of De-Immunized VL Dimers and Fusions Thereof

To determine toxicity of the anti-TNF-alpha polypeptides of the invention, the study design outlined in Table 8 below is implemented in rats.

TABLE 8

| STUDY DESIGN: | | |
|---|---|---|
| | Dose Escalation Study | |
| Phase A | Males | Females |
| Dose Level 1 | 2 | 2 |
| Dose Level 2 | 2 | 2 |
| Dose Level 3 | 2 | 2 |
| Dose Level 4 | 2 | 2 |
| | MTD Study | |
| Phase B | Males | Females |
| Control | 5 | 5 |
| High Dose | 5 | 5 |

In Phase A, all doses are administered on day 1 to determine the maximum tolerated dose (MTD); animals are dosed once at each designated level. In Phase B, animals are dosed once on day 1 at a dose based on Phase A. Administration is by subcutaneous or intravenous injection.

Animals in Phase A are observed twice daily for mortality and/or moribundity for 4 days at each level. Animals in Phase B are observed twice daily for 7 days. Also, body weight is measured for each animal at each observation time point. For Phase B animals, clinical pathology analyses are performed including: hematology, coagulation, clinical chemistry, and urinalysis evaluations on surviving animals at termination of the study, and tissues are saved from non-surviving animals. The following organs also are weighed following termination of Phase B animals: adrenals, brain, heart, kidneys, liver, spleen, thyroid with parathyroid, thymus. Standard statistical analysis is used.

Example 16

Acute Toxicity Study of De-Immunized VL Dimers and Fusions Thereof

To determine toxicity of the anti-TNF-alpha polypeptides of the invention, the study design outlined in Table 9 below is implemented in rats.

TABLE 9

STUDY DESIGN:

|  | Males | Females |
|---|---|---|
| Vehicle Control | 1 | 1 |
| Low Dose | 1 | 1 |
| Mid Dose | 1 | 1 |
| High Dose | 1 | 1 |

Doses are administered by subcutaneous injection once on day 1 of the study, and the animals are observed twice daily for mortality and moribundity. Electrocardiograms also are obtained for all animals prior to the initiation of the study, as well as pre- and post-dose on study days 1 and 14. Detailed clinical observations and body weights also are measured daily during the course of the study. Clinical pathology analyses also are conducted, including hematology, coagulation, clinical chemistry, and urinalysis evaluations on surviving animals at termination of the study (day 15).

Example 17

4-Week Toxicity Study of De-Immunized VL Dimers and Fusions Thereof

To further assess the toxicity of the anti-TNF-alpha polypeptides of the invention, the study design outlined in Table 10 below is implemented in rats.

TABLE 10

STUDY DESIGN:

|  | Main Study | | Recovery | | Toxicokinetics | |
|---|---|---|---|---|---|---|
|  | Males** | Females* | Males | Females | Males | Females |
| Vehicle Control | 15 | 15* | 5 | 5 | — | — |
| Low Dose | 15 | 15 | — | — | 6 | 6 |
| Mid Dose | 15 | 15 | — | — | 6 | 6 |
| High Dose | 15 | 15 | 5 | 5 | 6 | 6 |

**Six animals per sex per group will be designated for neurobehavioral evaluations and four animals per sex per group will be designated for respiratory evaluations Six animals per sex per group are designated for neurobehavioral evaluations and four animals per sex per group are designated for respiratory evaluations.

Doses are administered by subcutaneous or intravenous injection weekly (days 1, 8, 15, 22, and 29 of the study), and the animals are observed twice daily for mortality and moribundity. Detailed clinical observations and body weights also are measured weekly during the course of the study. Six animals of the main study per sex per group undergo neurobehavioral evaluations prior to dosing, at the estimated time of peak effect on day 1, and 24 hours following the first dose.

Four main study animals per sex per group are subjected to respiratory evaluations. The animals are placed in a plethysmograph chamber at least 2 hours prior to dosing on day 1. After at least 60 minutes, respiratory monitoring is initiated to establish baseline data. The animals are temporarily removed from the plethysmograph chambers for dosing after at least 1 hour of baseline recording. Immediately following dosing, the animals are returned to the plethysmograph chamber and continue to be monitored for a period of at least 4 hours. Food and water are not available during respiratory recording sessions. Respiratory endpoints measured include respiratory rate, tidal volume, and minute volume.

Clinical pathology analyses also are conducted, including hematology, coagulation, clinical chemistry, and urinalysis evaluations on surviving main study animals once at the terminal or recovery necropsy. Ophthalmology examination also is conducted in all animals before the study and in surviving main study animals at termination and recovery.

Toxicokinetics are measured based on blood (0.5 mL) collected on days 1 and 29 (from cohorts of 3 animals/sex; 2 cohorts bled three times to equal six time points and 216 total samples). Blood samples collected from the main study animals also are pre-tested for immunogenicity and immunophenotyping, and tested once again at the terminal or recovery necropsy (280 total samples). All main study (day 31) and recovery (day 57) animals are subjected to necropsy. Animals from the toxicokinetics study are euthanized and discarded. Weights are obtained for the following organs: adrenals, brain, heart, kidneys, liver, lungs, ovaries with oviducts, pituitary, prostate, salivary glands, seminal vesicles, spleen, thyroid with parathyroid, thymus, testes, and uterus.

Tissues are analyzed by microscopic pathology for all animals in the vehicle control and high dose groups and all found-dead animals. A full set of standard tissues (approximately 65), including target organs, are analyzed by microscopic pathology in low and mid dose groups and all recovery animals. Any gross lesions also are analyzed by microscopic pathology for any animal exhibiting same.

Data are analyzed by standard statistical analysis. Group pair-wise comparisons also are used for continuous endpoints; the Cochran Mantel Haenszel Test is used for categorical neurobehavioral endpoints only; repeated measures analysis of covariance is used with respiratory endpoints only. Toxicokinetic analysis include standard parameters such as AUC, $t_{1/2}$, tmax, and Cmax.

Example 18

Cardiovascular Safety of De-Immunized VL Dimers and Fusions Thereof

To determine toxicity and cardiovascular safety of the anti-TNF-alpha polypeptides of the invention, the study design outlined in Table 11 below is implemented in monkeys.

TABLE 11

STUDY DESIGN:

|  | Main Study | | Recovery | |
|---|---|---|---|---|
|  | Males* | Females* | Males | Females |
| Placebo | 5 | 5 | 2 | 2 |
| Low Dose | 5 | 5 | — | — |
| Mid Dose | 5 | 5 | — | — |
| High Dose | 5 | 5 | 2 | 2 |

*Two animals/sex/group designated for cardiovascular evaluation

Two animals per sex per group are designated for cardiovascular evaluation. Doses are administered by subcutaneous or intravenous injection weekly (days 1, 8, 15, 22, and 29 of the study), and the animals are observed twice daily for mortality and moribundity. Detailed clinical observations and body weights also are measured weekly during the course of the study. Animals designated for cardiovascular evaluation are observed via remote camera on day 1. Physical examinations of the animals are conducted by a veterinarian on all animals prior to initiation of the study. Ophthalmology examination also is conducted in all animals before the study and in surviving main study animals at termination and recovery.

For cardiovascular evaluations, two main study animals per sex per group are surgically implanted with a pressure transducer equipped telemetry transmitter. The transmitter assembly is secured internally, the fluid-filled catheter placed into an appropriate artery, and ECG leads placed to allow for collection of cardiovascular (hemodynamic and electrocardiographic) data. For those animals designated for cardiovascular evaluations, data are collected while the animals are allowed free movement in the home cage. The animals are monitored continuously for at least 2 hours prior to, and approximately 20 hours subsequent to, the first administration. The following parameters are monitored: systolic, diastolic and mean arterial blood pressures; heart rate; electrocardiogram (RR, PR, QRS, QT, and QTc); and body temperature.

All animals are subjected to electrocardiogram testing before the study and all surviving animals pre-dose and post-dose on Day 1, pre-dose and post-dose prior to the terminal necropsy, and prior to the recovery necropsy. For those animals designated for cardiovascular evaluations, representative ECG tracings are printed from the raw data telemetry record and these animals have additional ECG tracings printed at the expected time of peak effect on day 1 and at the end of the cardiovascular monitoring period. All traces are reviewed by a board certified veterinary cardiologist who performs a qualitative evaluation of the electrocardiograms.

Clinical pathology analyses also are conducted, including hematology, coagulation, clinical chemistry, and urinalysis evaluations on all animals prior to surgery, pre-test, and all surviving animals prior to the terminal or recovery necropsies. Toxicokinetics are measured based on blood collected on days 1 and 29 at six time points from each animal not designated for cardiovascular evaluation (384 total samples). Blood samples collected from all animals not designated for cardiovascular evaluation also are pre-tested for immunogenicity and immunophenotyping, and tested again at the terminal and recovery necropsies (72 total samples). All animals not designated for cardiovascular evaluation are subjected to necropsy on day 31 or 57.

Weights are obtained for the following organs: adrenals, brain, heart, kidneys, liver, lungs, ovaries with oviducts, pituitary, prostate, salivary glands, spleen, thyroid with parathyroid, thymus, testes, and uterus. Tissues are analyzed by microscopic pathology for all animals not designated for cardiovascular evaluation. A full set of standard tissues (approximately 70) are analyzed and any gross lesions also are analyzed by microscopic pathology for any animal exhibiting same.

Data are analyzed by standard statistical analysis. Repeated measures analysis of covariance is used with telemetry data only. Toxicokinetic analysis include standard parameters such as AUC, $t_{1/2}$, tmax, and Cmax.

Example 19

26-Week Toxicity Study of De-Immunized VL Dimers and Fusions Thereof

To further assess the toxicity of the anti-TNF-alpha polypeptides of the invention, the study design outlined in Table 12 below is implemented in rats.

TABLE 12

| STUDY DESIGN: | | | | |
|---|---|---|---|---|
| | Main Study | | Toxicokinetics | |
| | Males | Females | Males | Females |
| Vehicle Control | 15 | 15 | — | — |
| Low Dose | 15 | 15 | 6 | 6 |
| Mid Dose | 15 | 15 | 6 | 6 |
| High Dose | 15 | 15 | 6 | 6 |

Doses are administered by subcutaneous or intravenous injection weekly (27 total doses; final dose on day 183 of the study), and the animals are observed twice daily for mortality and moribundity. Detailed clinical observations and body weights also are measured weekly during the course of the study. Ophthalmology examination also is conducted in all animals before the study and in surviving main study animals at termination.

Clinical pathology analyses also are conducted, including hematology, coagulation, clinical chemistry, and urinalysis evaluations on surviving main study animals once at the terminal necropsy.

Toxicokinetics are measured based on blood (0.5 mL) collected on days 1 and 183 (from cohorts of 3 animals/sex; 2 cohorts bled three times to equal six time points and 216 total samples). Blood samples collected from the main study animals also are pre-tested for immunogenicity and immunophenotyping, and tested once again at the terminal necropsy (240 total samples). All main study animals (on day 185) are subjected to necropsy. Animals from the toxicokinetics study are euthanized and discarded. Weights are obtained for the following organs: adrenals, brain, heart, kidneys, liver, lungs, ovaries with oviducts, pituitary, prostate, salivary glands, seminal vesicles, spleen, thyroid with parathyroid, thymus, testes, and uterus.

Tissues are analyzed by microscopic pathology for all animals in the vehicle control and high dose groups and all found-dead animals. A full set of standard tissues (approximately 65), including target organs, are analyzed by microscopic pathology in low and mid dose groups. Any gross lesions also are analyzed by microscopic pathology for any animal exhibiting same.

Data are analyzed by standard statistical analysis. Toxicokinetic analysis include standard parameters such as AUC, $t_{1/2}$, tmax, and Cmax.

Example 20

Clinical Development of De-Immunized VL Dimers and Fusions Thereof

A preliminary Phase 1/2 clinical development plan for the anti-TNF-alpha polypeptides of the invention involves three stages, as outlined below.

Stage 1 involves a Phase 1a single ascending dose (SAD) study performed in normal volunteers (6 and 2), using 40 subjects and over 28 days, to determine safety and pharmacokinetics (PK). The Phase 1a study is designed as a single-center, sequential-cohort, double-blind, placebo-controlled, SAD study in 40 healthy volunteers aged 18-55 years, inclusive. Healthy adult volunteers are selected who have had no prior exposure to therapeutic antibodies (investigational or other). The study evaluates the safety and tolerability, and characterizes the PK and pharmacodynamics (PD), of the anti-TNF-alpha polypeptides of the invention, following successively higher single doses. Dose selection is based on extrapolation from a pharmacologically active dose.

Eligible adult subjects are assigned sequentially to 1 of 5 cohorts, at successively higher single doses. Eight subjects per cohort are randomized in a 3:1 manner to receive active drug or matching placebo. Subjects are confined in a Phase 1 unit for 12 hours prior to dosing, during dosing, and for 24 hours after dosing (Study Days 1-2) for observation and PK/PD sampling. Subjects return on Study Day 8 (7 days after dosing) and Study Day 29 for additional safety evaluations and at more frequent intervals for PK sampling. The safety and available PK data from all subjects are reviewed after all subjects in a cohort have completed the Study Day 8 evaluation. Since PD can be assessed in normal volunteers, the study can confirm the PK/PD simulation derived from data from rat and single dose monkey studies.

Stage 2 involves a Phase 1b multiple ascending dose (MAD) study designed as a multi-center, sequential-cohort, double-blind, placebo-controlled study in 40 to 50 subjects with moderate to severe rheumatoid arthritis (based on the American College or Rheumatology Criteria of 1987 and 2010 Classification Systems). The study evaluates the safety and tolerability, and characterizes the PK, PD, and preliminary clinical efficacy (based on ACR20/DAS28 at Week 14) of the anti-TNF-alpha polypeptides of the invention in subjects with rheumatoid arthritis following 4 doses administered subcutaneously.

Eligible adult subjects, who continue to receive methotrexate at a weekly stable dose, are assigned sequentially to 1 of up to 5 cohorts, at successively higher multiple doses. Eight to ten (8-10) subjects per cohort are randomized in a 3:1 (or 4:1) manner to receive active drug or matching placebo on Study Days 1, 29/Week4, 57/Week 8, and 85/Week 12. Subjects return at specified time points for safety and PK evaluations, and at Weeks 6 and 14 for efficacy evaluations. The safety and PK data from all subjects are reviewed after all cohort subjects complete the Week 6 evaluation. Eligible subjects meet the following criteria: (i) diagnosis of rheumatoid arthritis within 3 months; and (ii) treatment for at least 12 weeks with methotrexate prior to randomization, but do not have any of the following characteristics: (i) an autoimmune disease other than rheumatoid arthritis; (ii) a history of acute inflammatory joint disease other than rheumatoid arthritis; (iii) latent or active tuberculosis; (iv) a fever or persistent chronic or active recurring infection requiring treatment with antibiotics, antivirals, or antifungals within 4 weeks prior to the screening visit, or history of frequent recurrent infections; (v) immunization with any live (attenuated) vaccine within 3 months prior to the randomization visit (e.g., varicella-zoster vaccine, oral polio, rabies); (vi) tuberculosis vaccination within 12 months prior to screening; or (vii) prior therapy with a TNF inhibitor or any other biologic agents within 3 months prior to inclusion.

Stage 3 involves an initial Phase 2 study designed as a multi-center, randomized, double-blind, placebo-controlled, parallel arm study of 3 dose regimens of the anti-TNF-alpha polypeptides of the invention, administered subcutaneously, in approximately 200 subjects with moderate to severe rheumatoid arthritis (ACR 1987 and 2010 Classification Systems). The study evaluates the safety, tolerability, PD, and preliminary efficacy (based on ACR20 and/or DAS28 at Weeks 14 and 26) of the anti-TNF-alpha polypeptides of the invention at 3 dose regimens over 6 months, identifying safe and therapeutic doses for Phase 3 trials.

Eligible adult subjects, who continue to receive methotrexate at a weekly stable dose, are randomized in a 3:1 manner to receive 1 of 3 dose regimens of an anti-TNF-alpha polypeptide of the invention or placebo. DMARDs other than stable dosages of methotrexate are stopped at least 4 weeks, and 12 weeks for biologics, prior to randomization. Subjects receive methotrexate weekly for at least 12 weeks (stable dosage for at least 4 weeks) before enrollment. Stable dosages of non-steroidal anti-inflammatory drugs (NSAIDs) are permitted.

Approximately 200 eligible subjects are randomized to receive active drug or matching placebo every 4 weeks for 7 doses. Subjects return at specified time points for safety and PK evaluations, and at Weeks 14 and 26 for efficacy evaluations. The last study visit will be at Week 28. Eligible subjects meet the same criteria as outlined above, except that there is a diagnosis of rheumatoid arthritis of 3 months duration.

Example 21

Immunogenicity Analysis of De-Immunized VL18-3L-VL11-PEP Variants

Immunogenicity analysis of de-immunized VL18-3L-VL11-PEP variants is performed with Epibase IV platform (Algonomics/LONZA). Algonomics Epibase IV™ evaluates immunogenicity potential of antibody therapeutics by directly measuring T-cell responses in a naïve donor population representative. It identifies T-cell epitopes on proteins and allows direct comparison of immunogenicity profiles of protein leads. Combined with the Algonomics Epibase™ in silico tool, Algonomics Epibase IV™ cellular assays facilitate the selection of best leads. Characterization and comparison of T-cell responses raised by de-immunized VL18-3L-VL11-DI #3-PEP DI and VL18-3L-VL11-DI #5-PEP DI variants is performed in a fifty (50) donor population using DC: CD4 assays. Evaluation of VL18-3L-VL11 fused to wild-type and de-immunized PEP are also performed and used as control.

The invention claimed is:

1. A polypeptide comprising
a first antibody single domain that binds TNF-alpha, said first domain comprising a first light chain variable domain (VL),
wherein said first light chain variable domain comprises the amino acid sequence of SEQ ID NO:1 (VL18), or a TNF-alpha-binding fragment or a de-immunized derivative thereof, said de-immunized derivative formed by elimination of at least one $T_H$ epitope in said first light chain variable domain; and
a second antibody single domain—that binds TNF-alpha, said second domain comprising a second light chain variable domain or a TNF-alpha-binding fragment or a de-immunized derivative thereof, said de-immunized derivative formed by elimination of at least one $T_H$ epitope in said second light chain variable domain;
wherein said first and said second single domains together form a dimer.

2. The polypeptide according to claim 1 wherein said first and/or second variable domain antagonizes binding of human TNF-alpha to a TNF-alpha receptor.

3. The polypeptide according to claim 2 wherein said first and/or second variable domain further cross-reacts with at least one other mammalian TNF-alpha, wherein said mammal is not a primate;
  wherein said mammal is a rat or a mouse; or
  wherein said first and/or second variable domain cross-reacts with TNF-alpha of at least two other mammals, said at least two other mammals being a rodent and a non-rodent species.

4. The polypeptide according to claim 1 wherein said de-immunized derivative of said first variable domain comprising the amino acid sequence of SEQ ID NO:1 (VL18) is formed by at least one amino acid substitution selected from the group consisting of T7Q, V15P, (A51V-L54R/A51V-L54E), K63S, E79K, C80S, T91A, and L111K, said substitutions referring to amino acid positions in SEQ ID NO:1; or
  wherein said de-immunized derivative of said first variable domain comprises the amino acid sequence selected from the group consisting of SEQ ID NOs:19-23 (five VL18 variants), and a TNF-alpha-binding fragment thereof; and/or
  wherein said de-immunized derivative of said second variable domain comprises the amino acid sequence of SEQ ID NO:2 (VL11) de-immunized by at least one amino acid substitution selected from the group consisting of T7Q, V15P, R31S, (A51V-L54R /A51V-L54E), K63S, E79K, C80S, T91A, A100S, and E106K, said substitutions referring to amino acid positions in SEQ ID NO:2; or
  wherein said de-immunized derivative of said second variable domain comprises the amino acid sequence selected from the group consisting of SEQ ID NOs: 24-28 (five VL11 variants), and a TNF-alpha-binding fragment thereof.

5. The polypeptide according to claim 1, further comprising an albumin-binding domain, or a de-immunized derivative thereof, linked to said first variable domain or to said second variable domain,
  wherein said de-immunized derivative of said albumin-binding domain is formed by eliminating at least one $T_H$ epitope in said albumin-binding domain.

6. The polypeptide according to claim 5 wherein said albumin-binding domain, or said de-immunized derivative thereof, is linked to said polypeptide as a fusion; or is linked to said polypeptide as a fusion via a linker;
  and/or
  wherein said albumin-binding domain enhances the serum half-life of said polypeptide by five-fold.

7. The polypeptide according to claim 6 wherein said albumin-binding domain comprises the amino acid sequence of SEQ ID NO:30 (PEP), or an albumin-binding fragment or a de-immunized derivative thereof,
  wherein said de-immunized derivative is formed by eliminating at least one $T_H$ epitope.

8. The polypeptide according to claim 7 wherein said de-immunized derivative of said albumin-binding domain is formed by at least one amino acid substitution selected from the group consisting of E12D, T29H-K35D, and A45D, said substitutions referring to amino acid positions in SEQ ID NO:30; or
  wherein said de-immunized derivative of said albumin-binding domain comprises the amino acid sequence of SEQ ID NO:31.

9. The polypeptide according to claim 6, wherein said linker is a peptide linker comprising the amino acid sequence of SEQ ID NO:29 (3L); and/or
  wherein said albumin-binding domain is an albumin-binding domain isolated from *S. zooepidemicus* Z5.

10. The polypeptide according to claim 5 wherein said polypeptide comprises the amino acid sequence of SEQ ID NO: 33 (VL18-3L-VL11-PEP) or a TNF-alpha-binding fragment or a de-immunized derivative thereof,
  wherein said de-immunized derivative is formed by eliminating at least one $T_H$ epitope.

11. The polypeptide according to claim 10 wherein said polypeptide comprises the amino acid sequence of SEQ ID NO:33 (VL18-3L-VL11-PEP).

12. A pharmaceutical composition comprising an effective amount of the polypeptide according to claim 11 and a pharmaceutically acceptable carrier.

13. The polypeptide according to claim 10, wherein said de-immunized derivative of the amino acid sequence of SEQ ID NO: 33 (VL18-3L-VL11-PEP) comprises the amino acid sequence selected from the group consisting of SEQ ID NOs: 34 and 40-44 (VL18-3L-VL11-PEP variants), or a TNF-alpha-binding fragment thereof.

14. A method for treating and/or delaying a TNF-alpha-related condition in a subject suffering therefrom and/or predisposed thereto, said method comprising:
  administering to said subject an effective amount of the polypeptide according to claim 1.

15. The method of claim 14 wherein said TNF-alpha-related condition is an inflammatory disorder or rheumatoid arthritis; and/or
  wherein said polypeptide is administered no more than twice a month or no more than once a month.

16. A pharmaceutical composition comprising an effective amount of the polypeptide according to claim 1 and a pharmaceutically acceptable carrier.

17. A method of making the polypeptide according to claim 1 comprising:
  (i) providing a host cell comprising a vector encoding said polypeptide;
  (ii) culturing said cell under conditions allowing expression of said polypeptide; and
  (iii) recovering said polypeptide from said culture.

18. The polypeptide according to claim 1, wherein said second variable domain comprises the amino acid sequence selected from the group consisting of SEQ ID NOs:1-18, or a TNF-alpha-binding fragment or a de-immunized derivative thereof, wherein said de-immunized derivative is formed by eliminating at least one $T_H$ epitope.

19. The polypeptide according to claim 18 wherein said second variable domain comprises the amino acid sequence of SEQ ID NO:2 (VL11), or a TNF-alpha-binding fragment or a de-immunized derivative thereof, wherein said de-immunized derivative is formed by eliminating at least one $T_H$ epitope; or
  wherein said dimer comprises the amino acid sequence of SEQ ID NO:32 (VL18-3L-VL11), or a TNF-alpha-binding fragment or a de-immunized derivative thereof, wherein said de-immunized derivative is formed by eliminating at least one $T_H$ epitope.

20. The polypeptide according to claim 19 wherein said de-immunized derivative of said dimer comprises the amino acid sequence selected from the group consisting of SEQ ID NOs: 35-39 (VL18-3L-VL11 variants), or a TNF-alpha-binding fragment thereof.

21. The polypeptide according to claim 19, wherein said first variable domain comprises the amino acid sequence of SEQ ID NO:1 (VL18) and said second variable domain comprises the amino acid sequence of SEQ ID NO:2 (VL11).

22. The polypeptide according to claim 21, wherein said dimer comprises the amino acid sequence of SEQ ID NO:32 (VL18-3L-VL11).

23. The polypeptide according to claim 1, wherein said first variable domain comprises the amino acid sequence of SEQ ID NO:1 (VL18).

24. A nucleic acid comprising a nucleotide sequence encoding a polypeptide comprising
- a first antibody single domain that binds TNF-alpha, said first domain comprising a first light chain variable domain (VL),
- wherein said first light chain variable domain comprises the amino acid sequence of SEQ ID NO:1 (VL18), or a TNF-alpha-binding fragment or a de-immunized derivative thereof, said de-immunized derivative formed by elimination of at least one $T_H$ epitope in said first light chain variable domain; and
- a second antibody single domain that binds TNF-alpha, said second domain comprising a second light chain variable domain or a TNF-alpha-binding fragment or a de-immunized derivative thereof, said de-immunized derivative formed b elimination of at least one $T_H$ epitope in said second light chain variable domain;
- wherein said first and said second single domains together form a dimer; or a vector comprising the nucleic acid; or a host cell comprising the vector.

* * * * *